(12) United States Patent
Jin et al.

(10) Patent No.: US 10,793,549 B2
(45) Date of Patent: Oct. 6, 2020

(54) SULFURYL-SUBSTITUTED BENZOHETEROCYCLIC DERIVATIVE, PREPARATION METHOD AND MEDICAL USE THEREOF

(71) Applicants: SHANGHAI HAIYAN PHARMACEUTICAL TECHNOLOGY CO., LTD., Shanghai (CN); YANGTZE RIVER PHARMACEUTICAL GROUP CO., LTD., Jiangsu (CN)

(72) Inventors: Yunzhou Jin, Shanghai (CN); Xiang Chen, Shanghai (CN); Pengfei Cheng, Shanghai (CN); Ping Bu, Shanghai (CN); Leitao Zhang, Shanghai (CN); Chong Wen, Shanghai (CN); Yingtao Liu, Shanghai (CN); Fusheng Zhou, Shanghai (CN); Ming Weng, Shanghai (CN); Jiong Lan, Shanghai (CN)

(73) Assignees: SHANGHAI HAIYAN PHARMACEUTICAL TECHNOLOGY CO., LTD. (CN); YANGTZE RIVER PHARMACEUTICAL GROUP CO., LTD. (CN)

( * ) Notice: Subject to any disclaimer, the term of this patent is extended or adjusted under 35 U.S.C. 154(b) by 0 days.

(21) Appl. No.: 16/306,373

(22) PCT Filed: Nov. 10, 2017

(86) PCT No.: PCT/CN2017/110461
§ 371 (c)(1),
(2) Date: Nov. 30, 2018

(87) PCT Pub. No.: WO2018/086590
PCT Pub. Date: May 17, 2018

(65) Prior Publication Data
US 2019/0300506 A1   Oct. 3, 2019

(30) Foreign Application Priority Data
Nov. 11, 2016   (CN) .......................... 2016 1 0994878

(51) Int. Cl.
C07D 401/14 (2006.01)
C07D 209/04 (2006.01)
C07D 209/56 (2006.01)
C07D 247/00 (2006.01)
C07D 401/02 (2006.01)
C07D 401/12 (2006.01)
C07D 487/00 (2006.01)
A61P 37/06 (2006.01)
A61P 35/00 (2006.01)
A61K 31/4045 (2006.01)
A61K 31/416 (2006.01)
A61K 31/44 (2006.01)

(52) U.S. Cl.
CPC ........ *C07D 401/14* (2013.01); *A61K 31/4045* (2013.01); *A61K 31/416* (2013.01); *A61K 31/44* (2013.01); *A61P 35/00* (2018.01); *A61P 37/06* (2018.01); *C07D 209/04* (2013.01); *C07D 209/56* (2013.01); *C07D 247/00* (2013.01); *C07D 401/02* (2013.01); *C07D 401/12* (2013.01); *C07D 487/00* (2013.01)

(58) Field of Classification Search
CPC .. C07D 401/14; C07D 209/04; C07D 209/56; C07D 247/00; C07D 401/02; C07D 401/12; C07D 487/00; A61P 37/06; A61P 35/00; A61K 31/4045; A61K 31/416; A61K 31/44

See application file for complete search history.

(56) References Cited

U.S. PATENT DOCUMENTS 8,598,167 B1 * 12/2013 Kuntz .................. C07D 405/14
514/234.5

FOREIGN PATENT DOCUMENTS

CN   102970869   3/2013
WO   2012075080  6/2012

OTHER PUBLICATIONS

International Search Report for PCT/CN2017/110461, dated Feb. 9, 2018, 4 pages.

* cited by examiner

Primary Examiner — Timothy R Rozof
(74) Attorney, Agent, or Firm — Adsero IP

(57) ABSTRACT

The present invention relates to a sulfuryl-substituted benzoheterocyclic derivative, a preparation method and medical use thereof. Particularly, disclosed is a compound of formula (I) or a pharmaceutically acceptable salt, stereoisomer, solvate, or prodrug thereof, and a preparation method and application thereof. The definition of each group in the formula can be found in the specification and the claims.

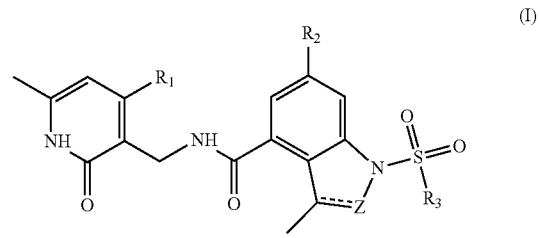

18 Claims, No Drawings

SULFURYL-SUBSTITUTED BENZOHETEROCYCLIC DERIVATIVE, PREPARATION METHOD AND MEDICAL USE THEREOF

CROSS-REFERENCE TO RELATED APPLICATION

This application claims priority to and is a 35 U.S.C. § 371 national phase application of PCT/CN2017/110461 (WO 2018/086590 A1), filed on Nov. 10, 2017 entitled "SULFONYL-SUBSTITUTED BENZOHETEROCYCLIC DERIVATIVE, PREPARATION METHOD AND MEDICAL USE THEREOF", which application claims priority to and the benefit of Chinese Application CN 201610994878.0 filed Nov. 11, 2016; the disclosures of which are incorporated herein by reference in their entirety.

TECHNICAL FIELD

The present disclosure belongs to the field of medical technology. In particular, the present disclosure particularly relates to a sulfuryl-substituted benzoheterocyclic derivative, its preparation method and use as an EZH2 inhibitor, and pharmaceutical compositions prepared therefrom.

BACKGROUND

The histone-lysine-N-methyltransferase EZH2 is involved in DNA methylation and, ultimately transcription repression; EZH2 catalyzes and transfers a methyl group to histone H3 at lysine 27 by the cofactor S-adenosyl-L-methionine. This methylation promotes the formation of heterochromatin, which triggers gene silencing.

EZH2 is a functional enzymatic part of PRC2, which controls and regulates development and differentiation through epigenetic maintenance of genes, thus ensuring the healthy development of the embryo. The mutation or overexpression of EZH2 is associated with the formation of many cancers. The EZH2 controlling gene controls the development of the tumor, the inhibition of EZH2 activity will slow the growth of the tumor. As a target inhibitor, EZH2 can regulate a variety of cancers including breast cancer, prostate cancer, melanoma and bladder cancer.

The PCT applications WO2011140324A1 and WO2012075080A1 disclose indole compounds as EZH2 inhibitors for the treatment of cancer. The PCT application WO2012118812A2 discloses bicyclic heterocyclic compounds as EZH2 inhibitors for the treatment of cancer.

Therefore, the inhibition of EZH2 activity will effectively reduce cell proliferation and invasion, thereby providing a beneficial treatment for EZH2-mediated diseases or conditions. The compounds of the present disclosure provide solutions for the treatment of diseases or EZH2-mediated tumor as EZH2 inhibitors.

SUMMARY

The object of the present disclosure is to provide a structurally novel compound which can act as EZH2 inhibitors.

According to a first aspect of the present disclosure, a compound represented by formula (I), or a pharmaceutically acceptable salt, stereoisomer, solvate or prodrug thereof is provided:

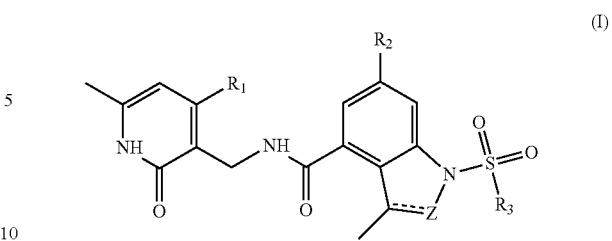

wherein,

Z is =CH—, —CH$_2$— or =N—;

"-----" is a single bond or double bond;

$R^1$ is a halogen (preferably fluorine, chlorine, bromine), $C_{1-8}$ alkyl (preferably $C_{1-6}$ alkyl, more preferably $C_{1-3}$ alkyl), halogenated $C_{1-8}$ alkoxy (preferably halogenated $C_{1-6}$ alkoxy, more preferably halogenated $C_{1-3}$ alkoxy), $C_{1-8}$ alkoxy (preferably $C_{1-6}$ alkoxy, more preferably $C_{1-3}$ alkoxy), $NR_{a0}R_{b0}$;

$R_2$ is a hydrogen, halogen (preferably fluorine, chlorine, bromine), CN, $C_{6-10}$ aryl (preferably phenyl), 4 to 6 membered saturated or partially unsaturated single heterocycle, 5 to 6 membered single heteroaryl ring;

$R_3$ is a $C_{1-8}$ alkyl (preferably $C_{1-6}$ alkyl, more preferably $C_{1-3}$ alkyl), $C_{2-8}$ alkynyl (preferably $C_{2-6}$ alkynyl, more preferably $C_{2-3}$ alkynyl), $C_{6-10}$ aryl (preferably phenyl), $C_{3-8}$ cycloalkyl (preferably $C_{3-6}$ cycloalkyl), 4 to 6 membered saturated or partially unsaturated single heterocycle or $NR_{a0}R_{b0}$;

the alkyl, cycloalkyl, alkoxy, aryl, 4 to 6 membered saturated or partially unsaturated single heterocycle, 5 to 6 membered single heteroaryl ring is unsubstituted or substituted by 1, 2 or 3 substituents selected from the group consisting of acetyl, hydroxy, hydroxymethyl, hydroxyethyl, carboxyl, —C(O)OC$_{1-6}$ alkyl, CN, 4 to 6 membered saturated single heterocycle, $NR_{a1}R_{b1}$, halogen, $C_{1-8}$ alkyl (preferably $C_{1-6}$ alkyl, more preferably $C_{1-3}$ alkyl), $C_{1-8}$ alkoxy (preferably $C_{1-6}$ alkoxy, more preferably $C_{1-3}$ alkoxy), halogenated $C_{1-8}$ alkyl (preferably halogenated $C_{1-6}$ alkyl, more preferably halogenated $C_{1-3}$ alkyl), $C_{2-8}$ alkenyl (preferably $C_{2-6}$ alkenyl, more preferably $C_{2-3}$ alkenyl) and —CH$_2$—L$_1$; L$_1$ is 4 to 6 membered saturated single heterocycle or $NR_{a1}R_{b1}$;

$R_{a0}$, $R_{b0}$, $R_{a1}$, $R_{b1}$ are each independently hydrogen or $C_{1-8}$ alkyl (preferably $C_{1-6}$ alkyl, more preferably $C_{1-3}$ alkyl).

In another preferred embodiment, the aryl in $R_2$ is unsubstituted or substituted by 1, 2 or 3 groups selected from the group consisting of halogen (preferably fluorine, chlorine), CN, $C_{1-3}$ alkyl, halogenated $C_{1-3}$ alkyl, $C_{1-3}$ alkoxy, $NR_{a1}R_{b1}$, 4 to 6 membered saturated single heterocycle (preferably azetidine, piperidine, piperazine, morpholine or tetrahydropyran), —CH$_2$-L$_2$ and —O(CH$_2$)$_n$NR$_{a1}$R$_{b1}$; wherein L$_2$ is 4 to 6 membered saturated single heterocycle (preferably azetidine, piperidine, piperazine, morpholine or tetrahydropyran) or $NR_{a1}R_{b1}$; $R_{a1}$, $R_{b1}$ are each independently hydrogen or $C_{1-3}$ alkyl; n is 1, 2 or 3.

In another preferred embodiment, the 4 to 6 membered saturated or partially unsaturated single heterocycle in $R_2$ is unsubstituted or substituted by 1, 2 or 3 groups selected from the group consisting of acetyl, hydroxy, hydroxymethyl, hydroxyethyl, carboxyl, —C(O)OC$_{1-6}$ alkyl, halogen (preferably fluorine, chlorine), halogenated $C_{1-3}$ alkyl, $C_{1-3}$ alkyl, CN, and $NR_{a1}R_{b1}$; wherein $R_{a1}$, $R_{b1}$ are each independently hydrogen or $C_{1-3}$ alkyl.

In another preferred embodiment, the 5 to 6 membered single heteroaryl ring in $R_2$ is unsubstituted or substituted by 1, 2 or 3 groups selected from the group consisting of halogen (preferably fluorine, chlorine), $C_{1-3}$ alkyl, CN, halogenated $C_{1-3}$ alkyl, $C_{1-3}$ alkoxy $NR_{a1}R_{b1}$, 4 to 6 membered saturated single heterocycle (preferably azetidine, piperidine, piperazine, morpholine, tetrahydropyrrole or tetrahydropyran) and —CH$_2$-L$_2$; wherein L$_2$ is 4 to 6 membered saturated single heterocycle (preferably azetidine, piperidine, piperazine, morpholine, tetrahydropyrrole or tetrahydropyran) or $NR_{a1}R_{b1}$; $R_{a1}$, $R_{b1}$ are each independently hydrogen or $C_{1-3}$ alkyl.

In another preferred embodiment, the 4 to 6 membered saturated single heterocycle in $R_3$ is unsubstituted or substituted by 1, 2 or 3 groups selected from the group consisting of acetyl, hydroxy, hydroxymethyl, hydroxyethyl, carboxyl, —C(O)OC$_{1-6}$ alkyl, $C_{1-3}$ alkyl, halogen (preferably fluorine or chlorine), CN, and —CH$_2$-L$_3$; wherein L$_3$ is 4 to 6 membered saturated single heterocycle (preferably azetidine, piperidine, piperazine, morpholine or tetrahydropyran).

In another preferred embodiment, the phenyl in $R_3$ is unsubstituted or substituted by 1, 2 or 3 groups selected from the group consisting of $C_{1-3}$ alkyl, halogen (preferably fluorine or chlorine), CN, and —CH$_2$-L$_3$; wherein L$_3$ is 4 to 6 membered saturated single heterocycle (preferably azetidine, piperidine, piperazine, morpholine or tetrahydropyran).

In another preferred embodiment, Z is =CH—; "---------" is a double bond.

In another preferred embodiment, Z is —CH$_2$—; "---------" is a single bond.

In another preferred embodiment, Z is =N—; "---------" is a double bond.

In another preferred embodiment, $R_1$ is fluorine, chlorine, methyl, ethyl, propyl, methoxy, ethoxy, isopropoxy, trifluoro substituted ethoxy, difluoro substituted methoxy, NHCH$_3$.

In another preferred embodiment, $R_2$ is hydrogen, halogen (preferably fluorine, chlorine, bromine) or CN.

In another preferred embodiment, $R_2$ is $C_{6-10}$ aryl (preferably phenyl); the aryl is unsubstituted or substituted by 1, 2 or 3 groups selected from the group consisting of halogen (preferably fluorine, chlorine), CN, $C_{1-3}$ alkyl, halogenated $C_{1-3}$ alkyl, $C_{1-3}$ alkoxy, $NR_{a1}R_{b1}$, 4 to 6 membered saturated single heterocycle (preferably azetidine, piperidine, piperazine, morpholine or tetrahydropyran), —CH$_2$-L$_2$ and —O(CH$_2$)$_n$NR$_{a1}$R$_{b1}$; wherein L$_2$ is 4 to 6 membered saturated single heterocycle (preferably azetidine, piperidine, piperazine, morpholine or tetrahydropyran) or $NR_{a1}R_{b1}$; wherein n is 1, 2 or 3;

the 4 to 6 membered saturated single heterocycle is unsubstituted or substituted by 1, 2 or 3 groups selected from the group consisting of halogen (preferably fluorine, chlorine), halogenated $C_{1-3}$ alkyl, $C_{1-3}$ alkyl, CN, and $NR_{a1}R_{b1}$; wherein $R_{a1}$, $R_{b1}$ are each independently hydrogen or $C_{1-3}$ alkyl.

In another preferred embodiment, $R_2$ is 4 to 6 membered saturated or partially unsaturated single heterocycle (preferably 4 to 6 membered saturated single heterocycle, more preferably azetidine, piperidine, piperazine, tetrahydropyridine, morpholine, tetrahydropyrrole or tetrahydropyran); the 4 to 6 membered saturated or partially unsaturated single heterocycle is unsubstituted or substituted by 1, 2 or 3 groups selected from the group consisting of halogen (preferably fluorine, chlorine), halogenated $C_{1-3}$ alkyl, $C_{1-3}$ alkyl, CN, and $NR_{a1}R_{b1}$; wherein $R_{a1}$, $R_{b1}$ are each independently hydrogen or $C_{1-3}$ alkyl.

In another preferred embodiment, $R_2$ is 5 to 6 membered single heteroaryl ring (preferably pyridine, pyrimidine, pyrazol); the 5 to 6 membered single heteroaryl ring is unsubstituted or substituted by 1, 2 or 3 groups selected from the group consisting of halogen (preferably fluorine, chlorine), $C_{1-3}$ alkyl, CN, halogenated $C_{1-3}$ alkyl, $C_{1-3}$ alkoxy, $NR_{a1}R_{b1}$, 4 to 6 membered saturated single heterocycle (preferably azetidine, piperidine, piperazine, morpholine, tetrahydropyrrole or tetrahydropyran) and —CH$_2$-L$_2$; wherein L$_2$ is 4 to 6 membered saturated single heterocycle (preferably azetidine, piperidine, piperazine, morpholine, tetrahydropyrrole or tetrahydropyran) or $NR_{a1}R_{b1}$; $R_{a1}$, $R_{b1}$ are each independently hydrogen or $C_{1-3}$ alkyl;

the 4 to 6 membered saturated single heterocycle is unsubstituted or substituted by 1, 2 or 3 groups selected from the group consisting of halogen (preferably fluorine, chlorine), halogenated $C_{1-3}$ alkyl, $C_{1-3}$ alkyl, CN, and $NR_{a1}R_{b1}$.

In another preferred embodiment, $R_2$ is 5 to 6 membered single heteroaryl ring (preferably pyridine, pyrimidine, pyrazol); the 5 to 6 membered single heteroaryl ring is unsubstituted or substituted by 1, 2 or 3 groups selected from the group consisting of halogen (preferably fluorine, chlorine), CN, $C_{1-3}$ alkyl, $NR_{a1}R_{b1}$, 4 to 6 membered saturated single heterocycle (preferably azetidine, piperidine, piperazine, morpholine, tetrahydropyrrole or tetrahydropyran) and —CH$_2$-L$_2$; wherein L$_2$ is 4 to 6 membered saturated single heterocycle (preferably azetidine, piperidine, piperazine, morpholine, tetrahydropyrrole or tetrahydropyran) or $NR_{a1}R_{b1}$; $R_{a1}$, Rb1 are each independently hydrogen or $C_{1-3}$ alkyl;

the 4 to 6 membered saturated single heterocycle is unsubstituted or substituted by 1, 2 or 3 groups selected from the group consisting of halogen (preferably fluorine, chlorine), halogenated $C_{1-3}$ alkyl, and $C_{1-3}$ alkyl.

In another preferred embodiment, $R_2$ is hydrogen, fluorine, chlorine, bromine, CN; or $R_2$ is the following structure:

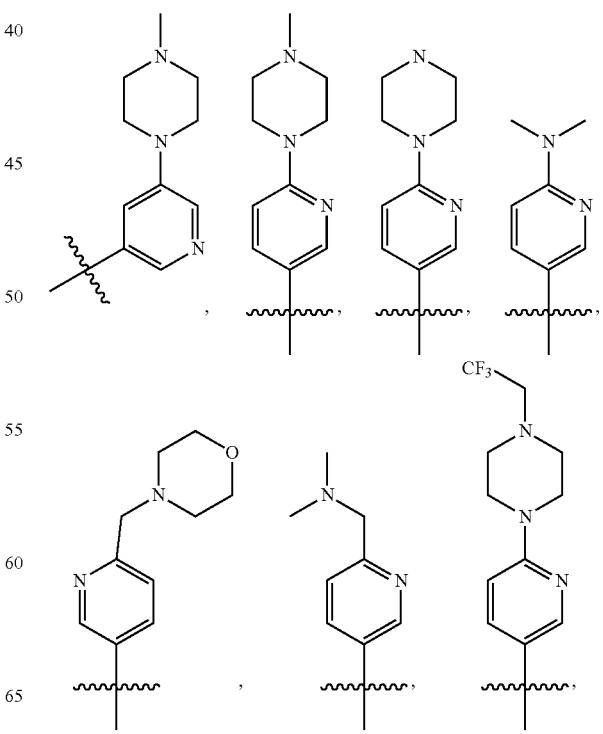

-continued
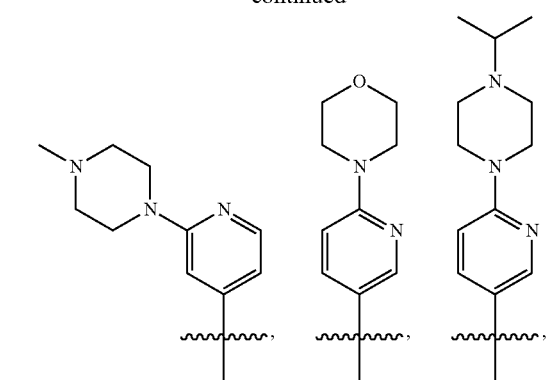
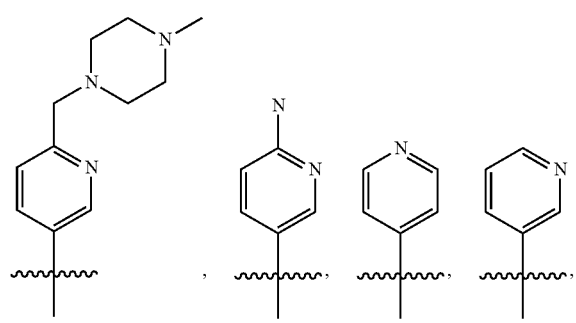
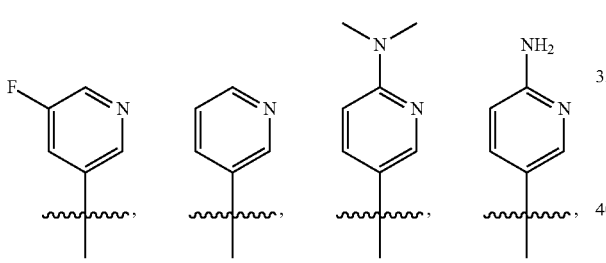
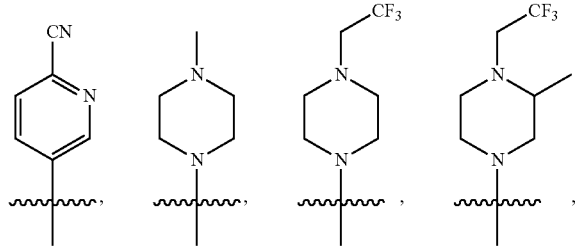
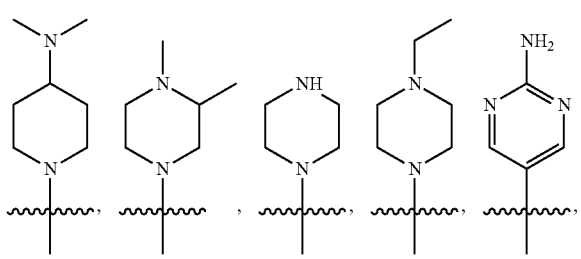
-continued
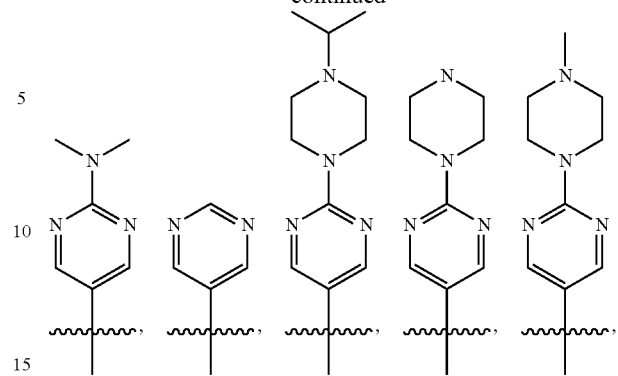
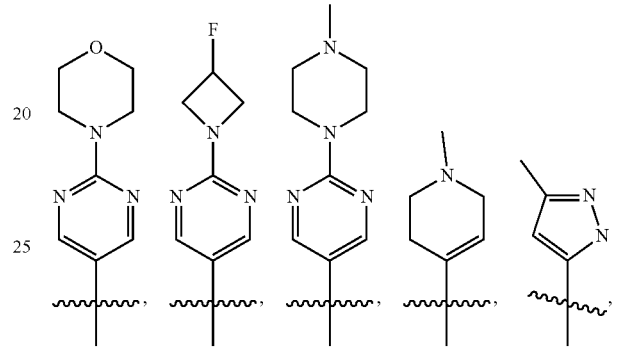
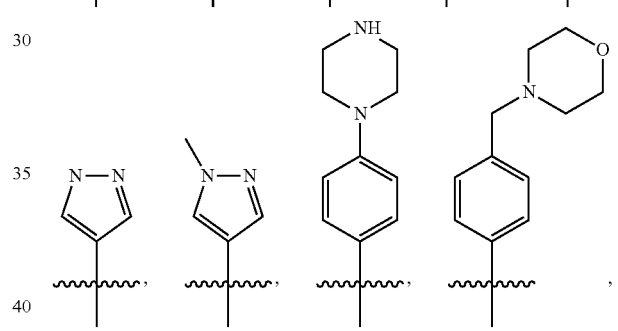
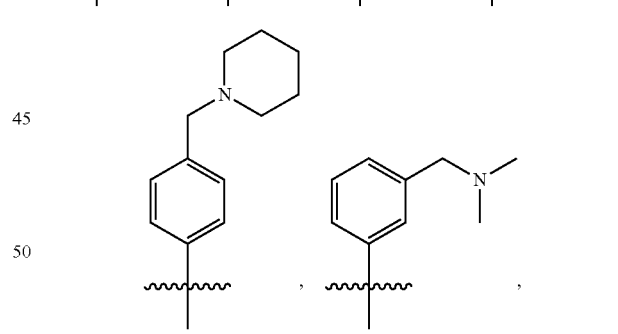

-continued

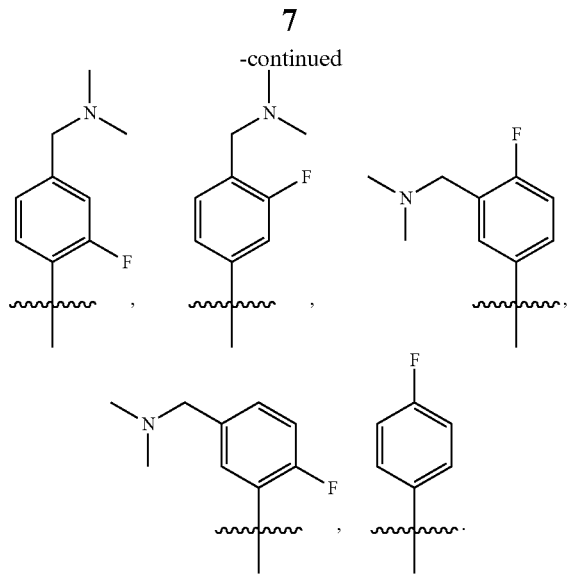

In another preferred embodiment, $R_3$ is $C_{1-8}$ alkyl (preferably $C_{1-6}$ alkyl, more preferably $C_{1-3}$ alkyl), $C_{1-8}$ alkyl substituted by $C_{1-8}$ alkoxy (preferably $C_{1-6}$ alkyl substituted by $C_{1-6}$ alkoxy, more preferably $C_{1-3}$ alkyl substituted by $C_{1-3}$ alkoxy), $C_{2-8}$ alkynyl (preferably $C_{2-6}$ alkynyl, more preferably $C_{2-3}$ alkynyl), 4 to 6 membered saturated single heterocycle (preferably azetidine, piperidine, piperazine, morpholine or tetrahydropyran), phenyl, $C_{3-8}$ cycloalkyl (preferably $C_{3-6}$ cycloalkyl), $NR^{a0}R_{b0}$; wherein $R_{a0}$, $R_{b0}$ are each independently hydrogen or $C_{1-8}$ alkyl (preferably $C_{1-6}$ alkyl, more preferably $C_{1-3}$ alkyl);

the phenyl, 4 to 6 membered saturated single heterocycle is unsubstituted or substituted by 1, 2 or 3 groups selected from the group consisting of $C_{1-3}$ alkyl, halogen (preferably fluorine or chlorine), CN, and —$CH_2$-$L_3$; wherein $L_3$ is 4 to 6 membered saturated single heterocycle (preferably azetidine, piperidine, piperazine, morpholine or tetrahydropyran).

In another preferred embodiment, $R_3$ is $C_{3-8}$ cycloalkyl substituted by $C_{2-8}$ alkenyl (preferably $C_{3-6}$ cycloalkyl substituted by $C_{2-6}$ alkenyl, more preferably $C_{3-6}$ cycloalkyl substituted by $C_{2-3}$ alkenyl, more preferably cyclopropyl substituted by allyl).

In another preferred embodiment, the compound of formula (I) is the structure represented by formula (II):

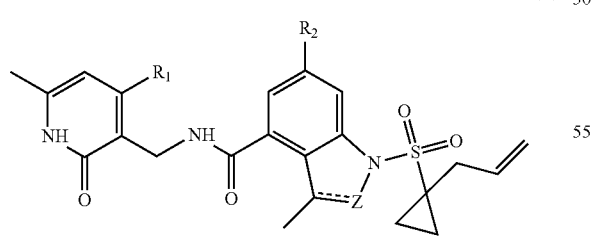

(II)

wherein $R_1$, $R_2$, Z are as previously defined.

In another preferred embodiment, in formula (II), Z is =CH—; "--------" is a double bond.

In another preferred embodiment, in formula (II), Z is —$CH_2$—; "--------" is a single bond.

In another preferred embodiment, in formula (II), Z is =N—; "--------" is a double bond.

In another preferred embodiment, Z is =CH—; "--------" is a double bond; $R_1$ is fluorine, chlorine, methyl, methoxy, isopropoxy.

In another preferred embodiment, Z is —$CH_2$—; "--------" is a single bond; $R_1$ is methyl, methoxy.

In another preferred embodiment, the compound is selected from the following Table A:

TABLE A

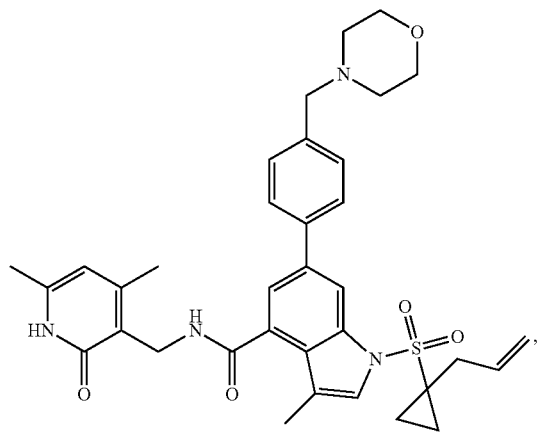 [SMILES: C=CCC1(S(=O)(=O)n2cc(C)c3c(C(=O)NCc4c(C)cc(C)[nH]c4=O)cc(-c4ccc(CN5CCOCC5)cc4)cc32)CC1]

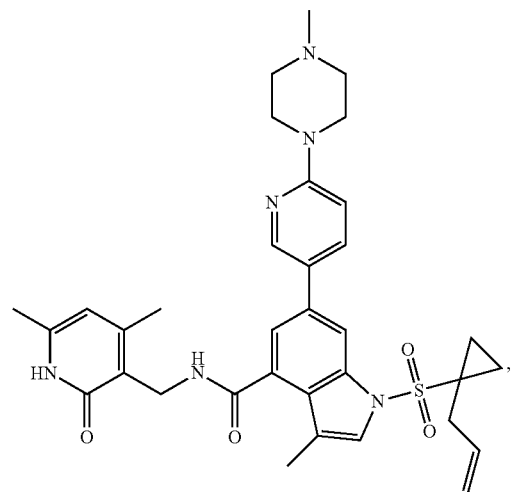 [SMILES: C=CCC1(S(=O)(=O)n2cc(C)c3c(C(=O)NCc4c(C)cc(C)[nH]c4=O)cc(-c4ccc(N5CCN(C)CC5)nc4)cc32)CC1]

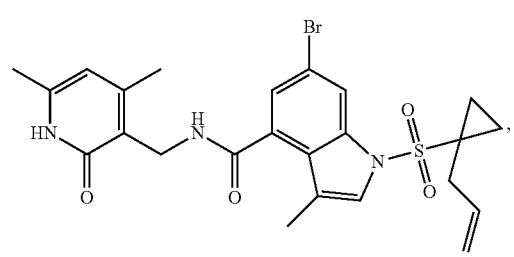 [SMILES: C=CCC1(S(=O)(=O)n2cc(C)c3c(C(=O)NCc4c(C)cc(C)[nH]c4=O)cc(Br)cc32)CC1]

TABLE A-continued
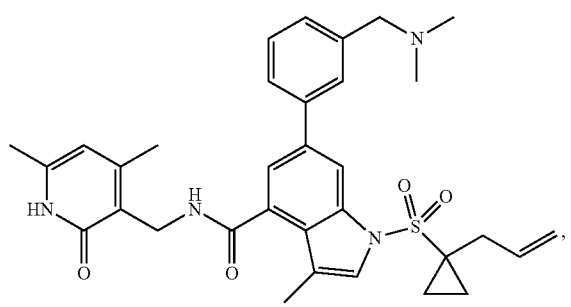 [SMILES: C=CCC1(S(=O)(=O)n2cc(C)c3c(C(=O)NCc4c(C)cc(C)[nH]c4=O)cc(-c4cccc(CN(C)C)c4)cc32)CC1]
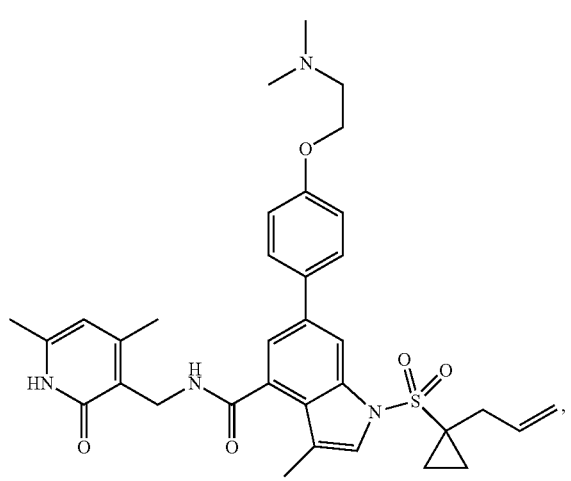 [SMILES: C=CCC1(S(=O)(=O)n2cc(C)c3c(C(=O)NCc4c(C)cc(C)[nH]c4=O)cc(-c4ccc(OCCN(C)C)cc4)cc32)CC1]
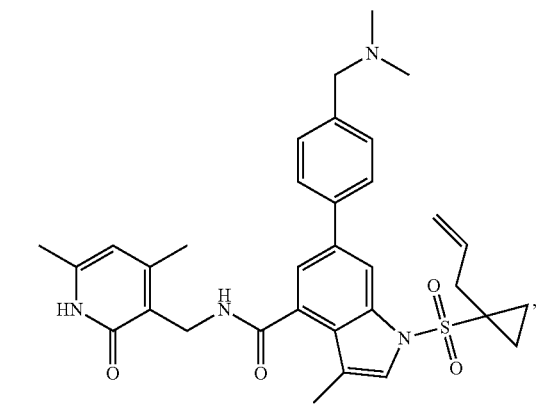 [SMILES: C=CCC1(S(=O)(=O)n2cc(C)c3c(C(=O)NCc4c(C)cc(C)[nH]c4=O)cc(-c4ccc(CN(C)C)cc4)cc32)CC1]
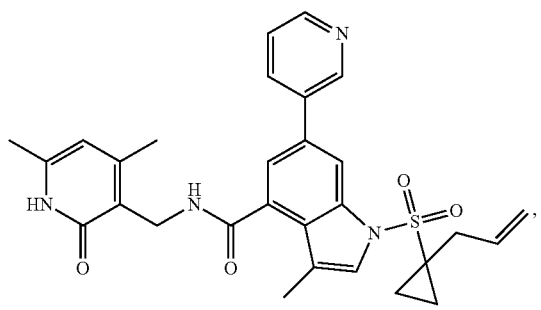 [SMILES: C=CCC1(S(=O)(=O)n2cc(C)c3c(C(=O)NCc4c(C)cc(C)[nH]c4=O)cc(-c4cccnc4)cc32)CC1]
TABLE A-continued
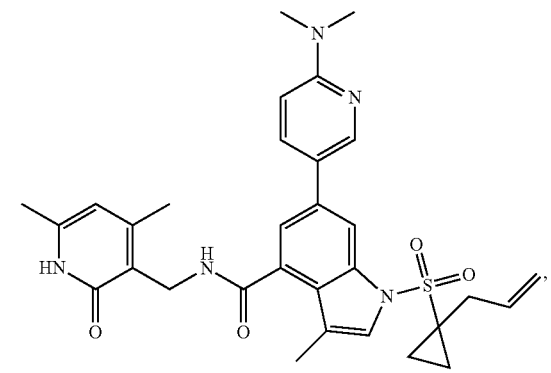 [SMILES: C=CCC1(S(=O)(=O)n2cc(C)c3c(C(=O)NCc4c(C)cc(C)[nH]c4=O)cc(-c4ccc(N(C)C)nc4)cc32)CC1]
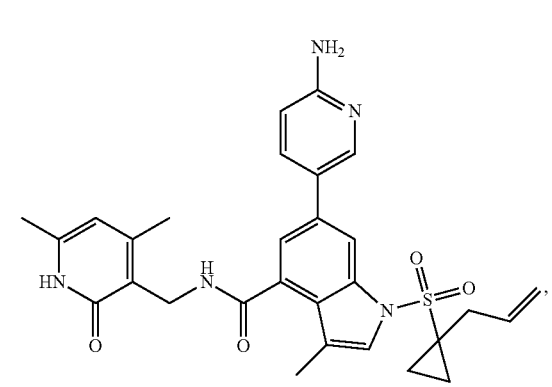 [SMILES: C=CCC1(S(=O)(=O)n2cc(C)c3c(C(=O)NCc4c(C)cc(C)[nH]c4=O)cc(-c4ccc(N)nc4)cc32)CC1]
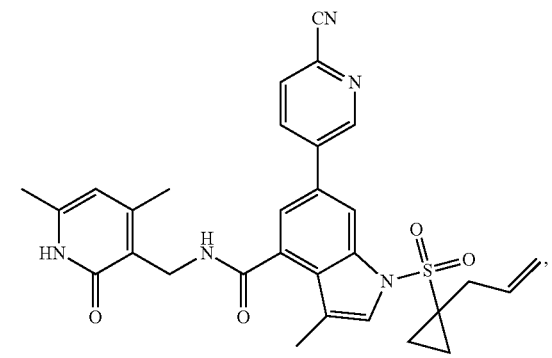 [SMILES: C=CCC1(S(=O)(=O)n2cc(C)c3c(C(=O)NCc4c(C)cc(C)[nH]c4=O)cc(-c4ccc(C#N)nc4)cc32)CC1]
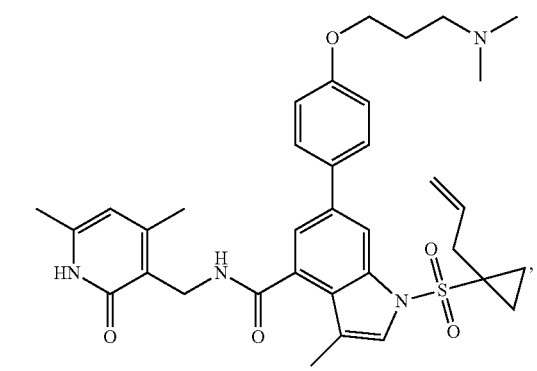 [SMILES: C=CCC1(S(=O)(=O)n2cc(C)c3c(C(=O)NCc4c(C)cc(C)[nH]c4=O)cc(-c4ccc(OCCCN(C)C)cc4)cc32)CC1]

TABLE A-continued
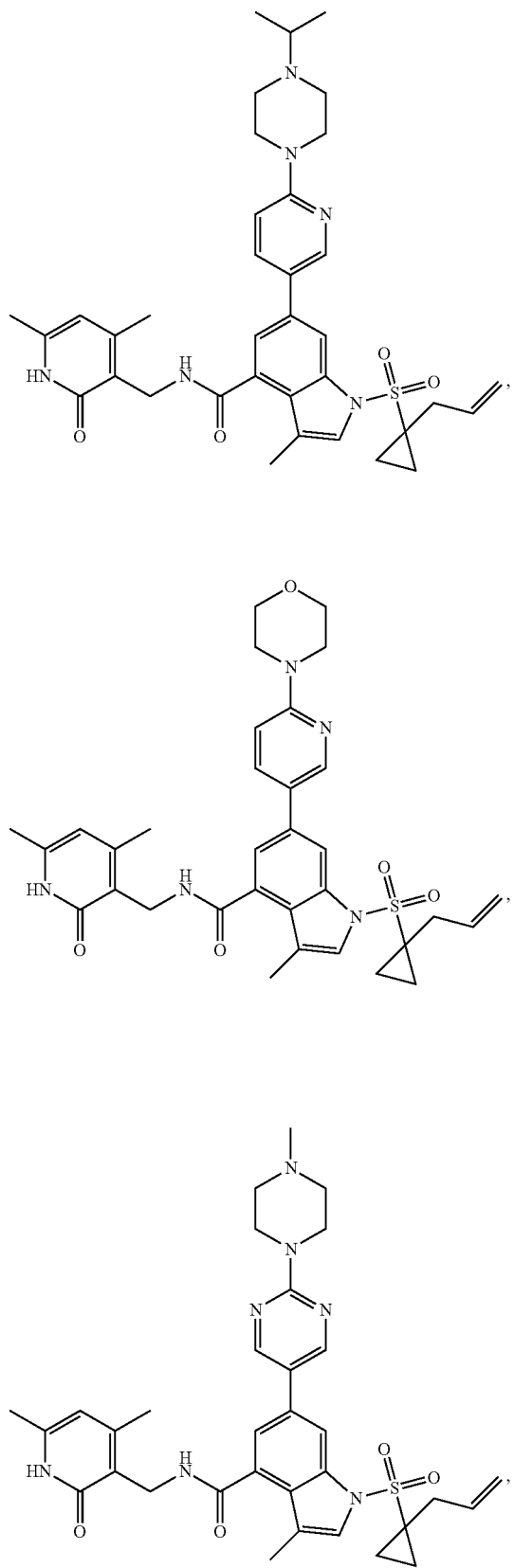
TABLE A-continued
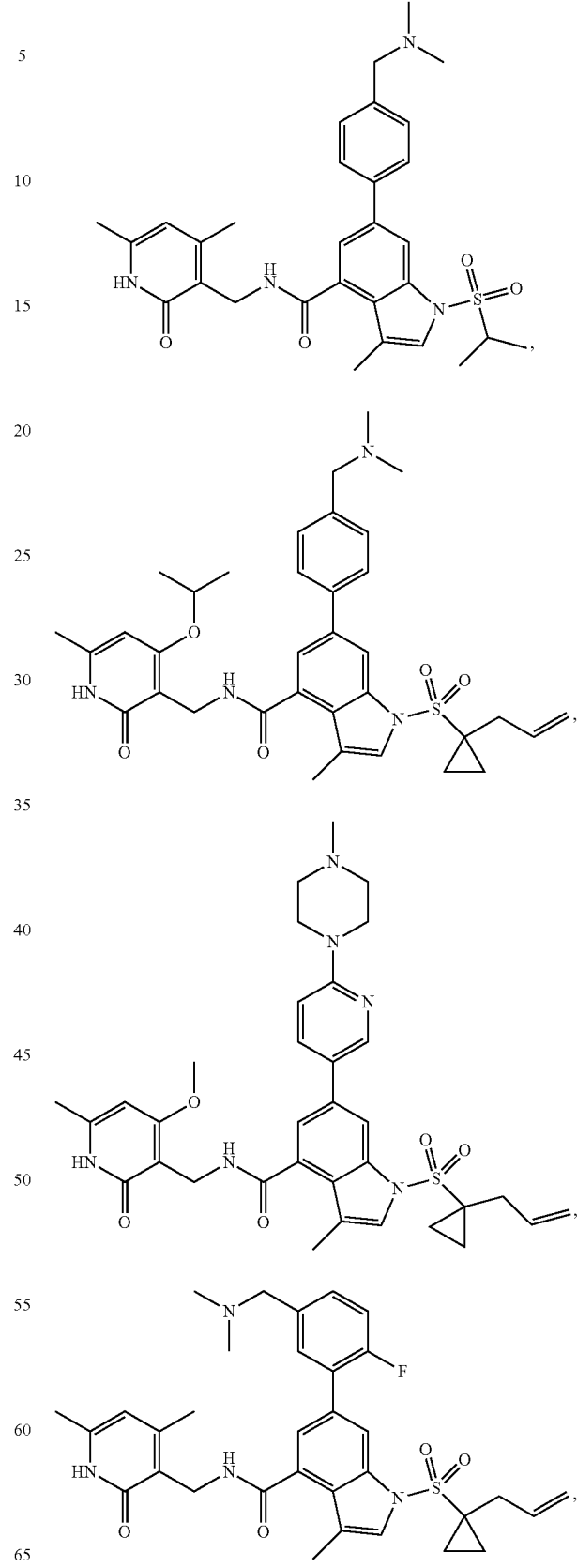

TABLE A-continued
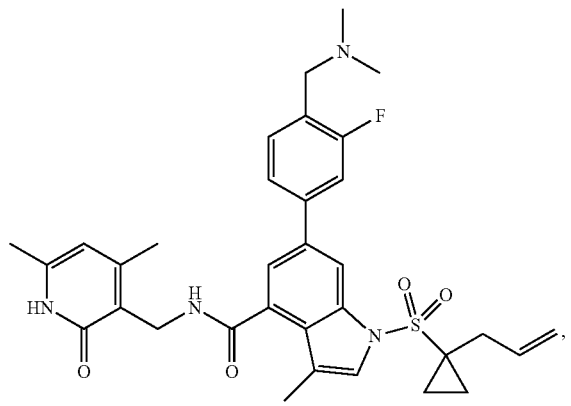 [SMILES: C=CCC1(S(=O)(=O)n2cc(C)c3c(C(=O)NCc4c(C)cc(C)[nH]c4=O)cc(-c4ccc(CN(C)C)c(F)c4)cc32)CC1]
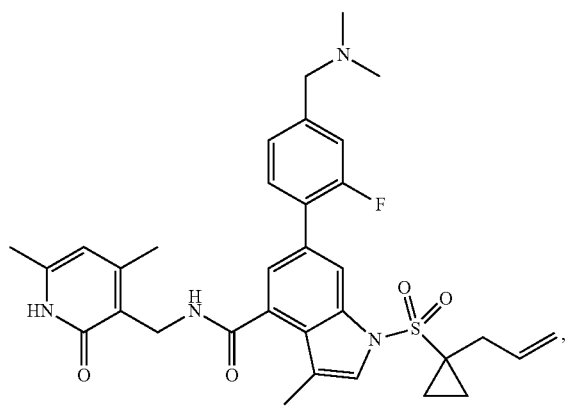 [SMILES: C=CCC1(S(=O)(=O)n2cc(C)c3c(C(=O)NCc4c(C)cc(C)[nH]c4=O)cc(-c4ccc(CN(C)C)cc4F)cc32)CC1]
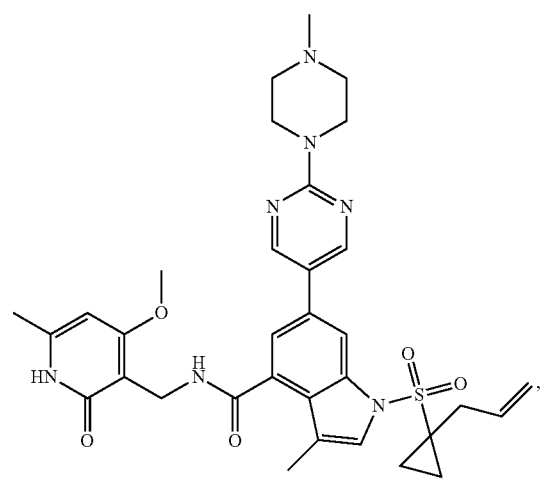
TABLE A-continued
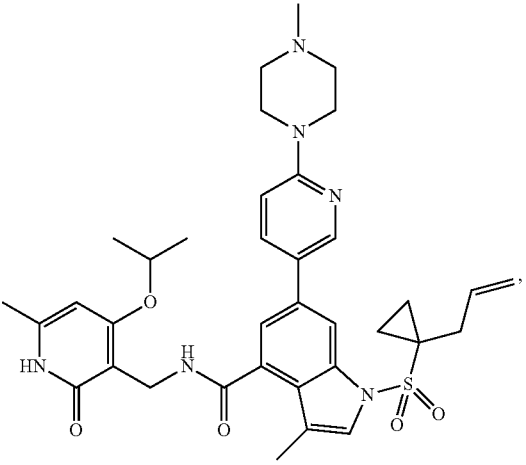 [SMILES: C=CCC1(S(=O)(=O)n2cc(C)c3c(C(=O)NCc4c(OC(C)C)cc(C)[nH]c4=O)cc(-c4ccc(N5CCN(C)CC5)nc4)cc32)CC1]
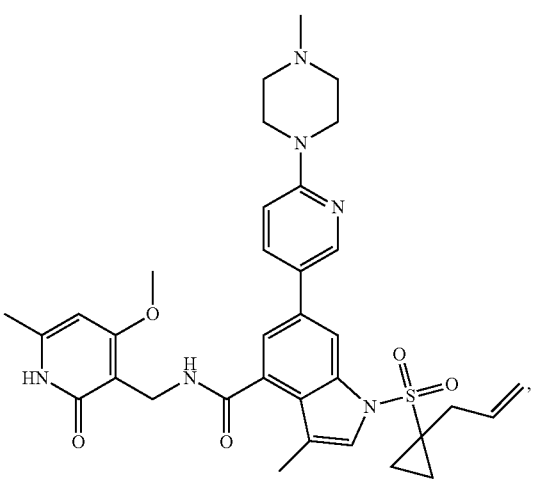 [SMILES: C=CCC1(S(=O)(=O)n2cc(C)c3c(C(=O)NCc4c(OC)cc(C)[nH]c4=O)cc(-c4ccc(N5CCN(C)CC5)nc4)cc32)CC1]
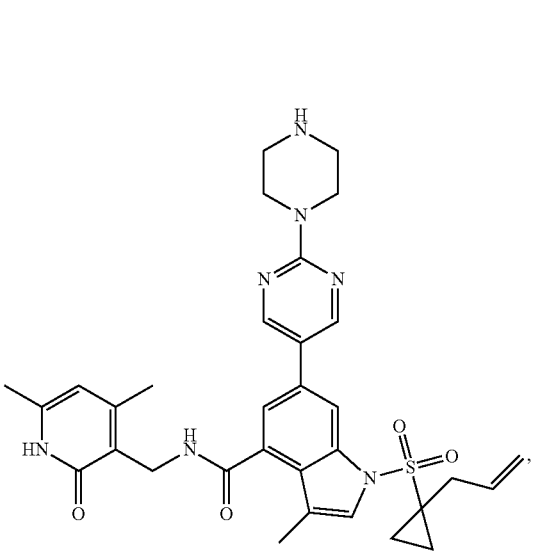 [SMILES: C=CCC1(S(=O)(=O)n2cc(C)c3c(C(=O)NCc4c(C)cc(C)[nH]c4=O)cc(-c4cnc(N5CCNCC5)nc4)cc32)CC1]

TABLE A-continued
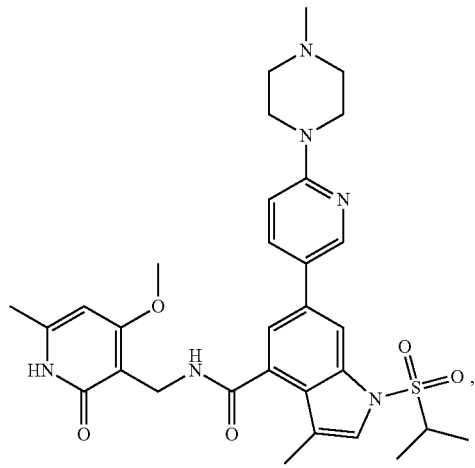 [SMILES: COc1cc(C)[nH]c(=O)c1CNC(=O)c1cc(-c2ccc(N3CCN(C)CC3)nc2)cc2c1c(C)cn2S(=O)(=O)C(C)C]
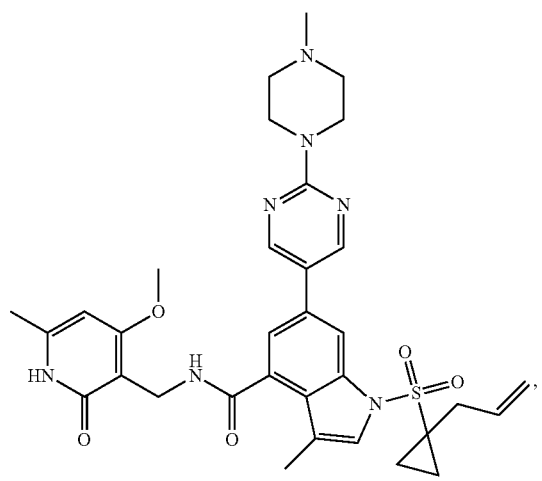 [SMILES: C=CCC1(S(=O)(=O)n2cc(C)c3c(C(=O)NCc4c(OC)cc(C)[nH]c4=O)cc(-c4cnc(N5CCN(C)CC5)nc4)cc32)CC1]
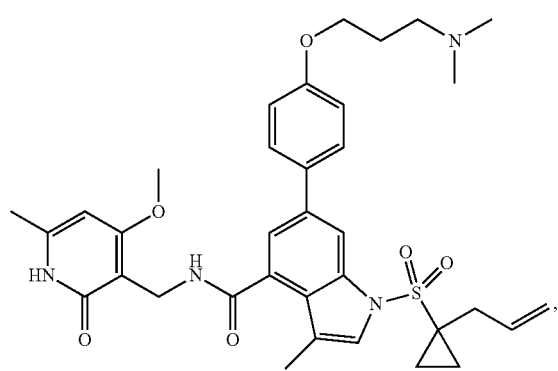 [SMILES: C=CCC1(S(=O)(=O)n2cc(C)c3c(C(=O)NCc4c(OC)cc(C)[nH]c4=O)cc(-c4ccc(OCCCN(C)C)cc4)cc32)CC1]
TABLE A-continued
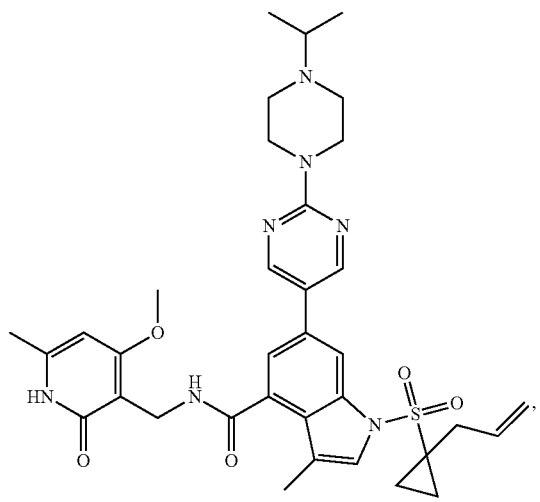 [SMILES: C=CCC1(S(=O)(=O)n2cc(C)c3c(C(=O)NCc4c(OC)cc(C)[nH]c4=O)cc(-c4cnc(N5CCN(C(C)C)CC5)nc4)cc32)CC1]

TABLE A-continued
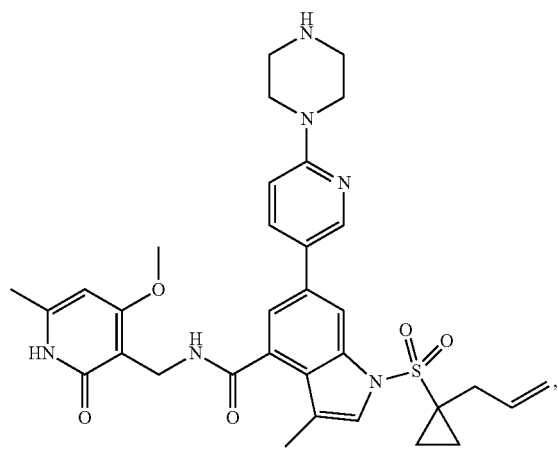 [SMILES: C=CCC1(S(=O)(=O)n2cc(C)c3c(C(=O)NCc4c(OC)cc(C)[nH]c4=O)cc(-c4ccc(N5CCNCC5)nc4)cc32)CC1]
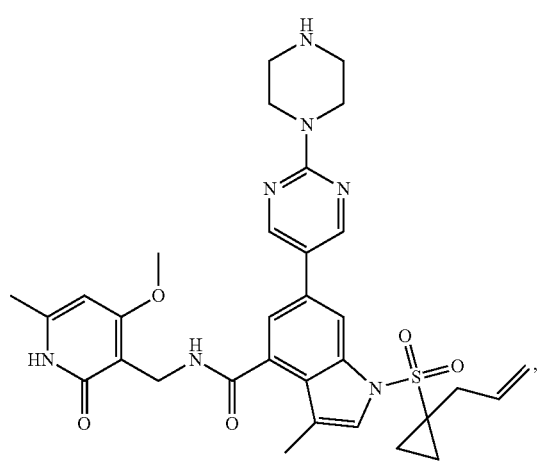 [SMILES: C=CCC1(S(=O)(=O)n2cc(C)c3c(C(=O)NCc4c(OC)cc(C)[nH]c4=O)cc(-c4cnc(N5CCNCC5)nc4)cc32)CC1]
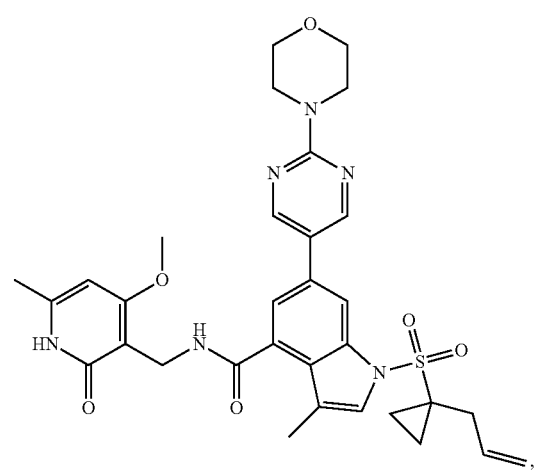 [SMILES: C=CCC1(S(=O)(=O)n2cc(C)c3c(C(=O)NCc4c(OC)cc(C)[nH]c4=O)cc(-c4cnc(N5CCOCC5)nc4)cc32)CC1]
TABLE A-continued
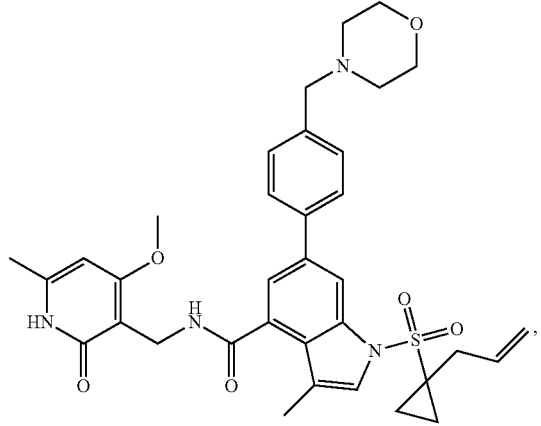 [SMILES: C=CCC1(S(=O)(=O)n2cc(C)c3c(C(=O)NCc4c(OC)cc(C)[nH]c4=O)cc(-c4ccc(CN5CCOCC5)cc4)cc32)CC1]
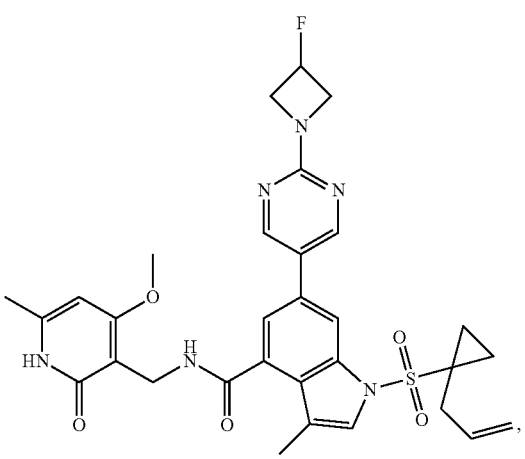 [SMILES: C=CCC1(S(=O)(=O)n2cc(C)c3c(C(=O)NCc4c(OC)cc(C)[nH]c4=O)cc(-c4cnc(N5CC(F)C5)nc4)cc32)CC1]
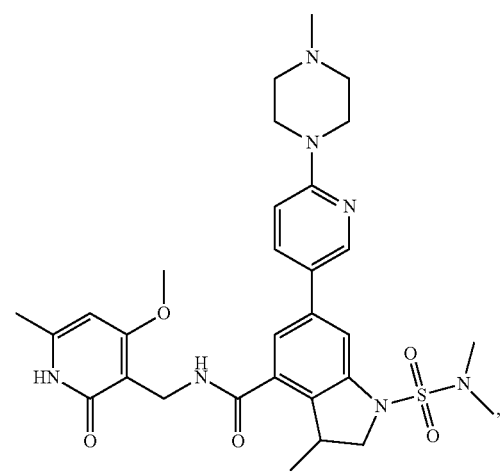

TABLE A-continued
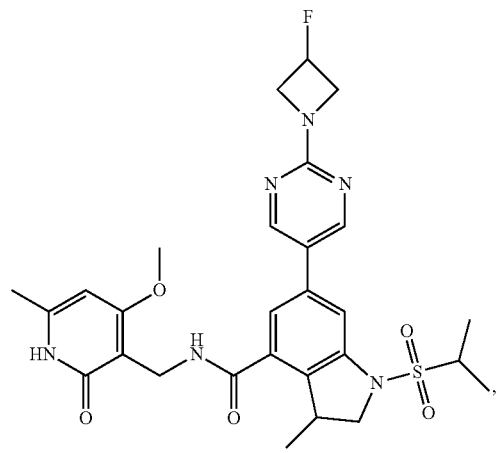 [SMILES: COc1cc(C)[nH]c(=O)c1CNC(=O)c1cc(-c2cnc(N3CC(F)C3)nc2)cc2c1C(C)CN2S(=O)(=O)C(C)C]
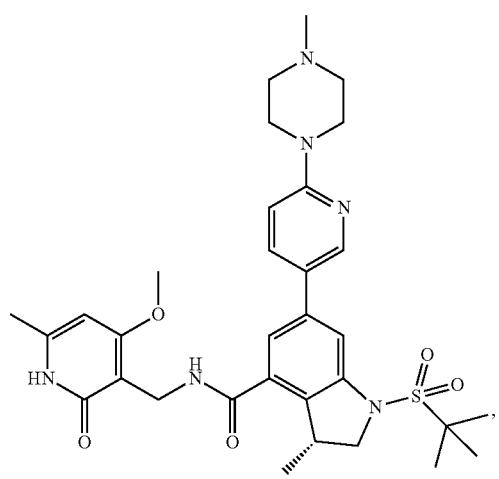 [SMILES: COc1cc(C)[nH]c(=O)c1CNC(=O)c1cc(-c2ccc(N3CCN(C)CC3)nc2)cc2c1[C@@H](C)CN2S(=O)(=O)C(C)(C)C]
TABLE A-continued
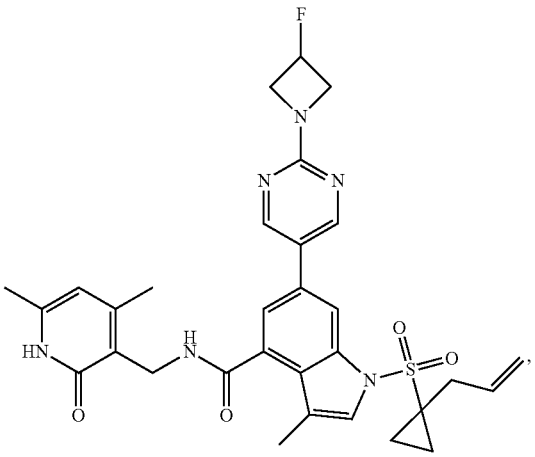 [SMILES: C=CCC1(S(=O)(=O)n2cc(C)c3c(C(=O)NCc4c(C)cc(C)[nH]c4=O)cc(-c4cnc(N5CC(F)C5)nc4)cc32)CC1]
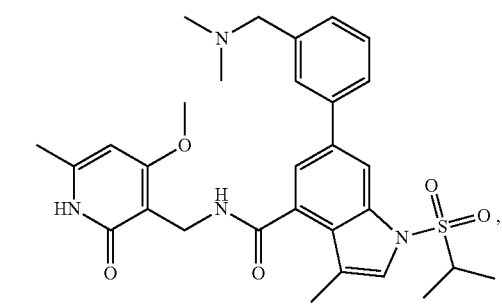 [SMILES: COc1cc(C)[nH]c(=O)c1CNC(=O)c1cc(-c2cccc(CN(C)C)c2)cc2c1c(C)cn2S(=O)(=O)C(C)C]
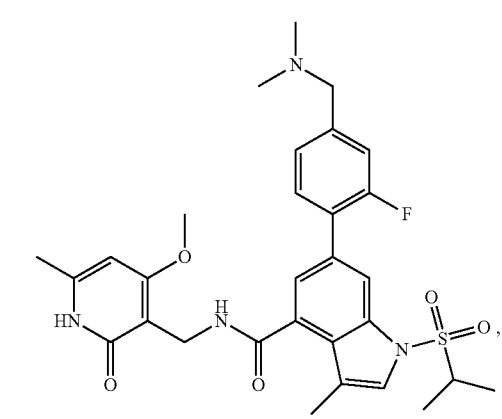 [SMILES: COc1cc(C)[nH]c(=O)c1CNC(=O)c1cc(-c2ccc(CN(C)C)cc2F)cc2c1c(C)cn2S(=O)(=O)C(C)C]
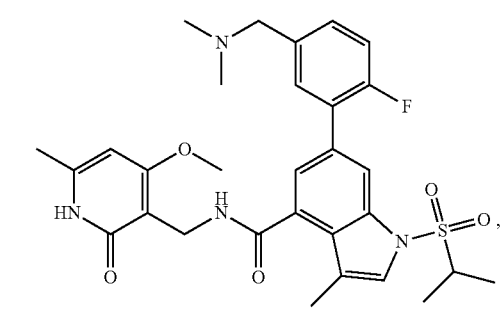 [SMILES: COc1cc(C)[nH]c(=O)c1CNC(=O)c1cc(-c2cc(CN(C)C)ccc2F)cc2c1c(C)cn2S(=O)(=O)C(C)C]

TABLE A-continued
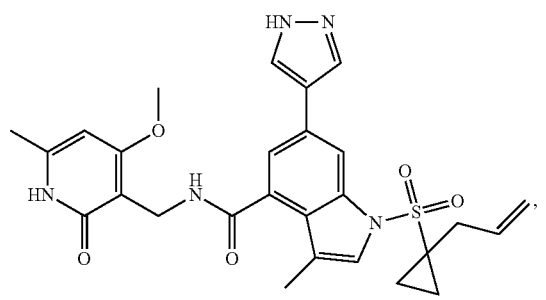 [SMILES: C=CCC1(S(=O)(=O)n2cc(C)c3c(C(=O)NCc4c(OC)cc(C)[nH]c4=O)cc(-c4cn[nH]c4)cc32)CC1]
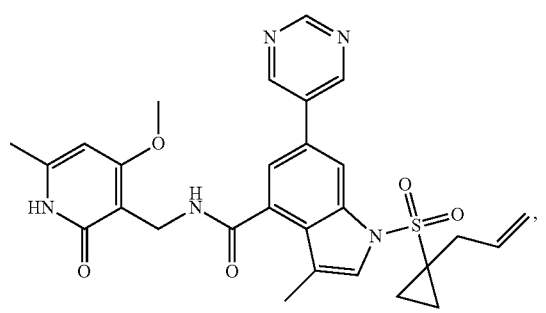
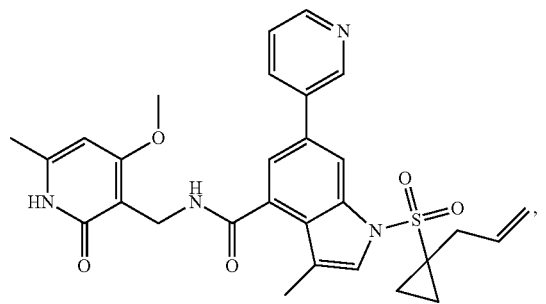
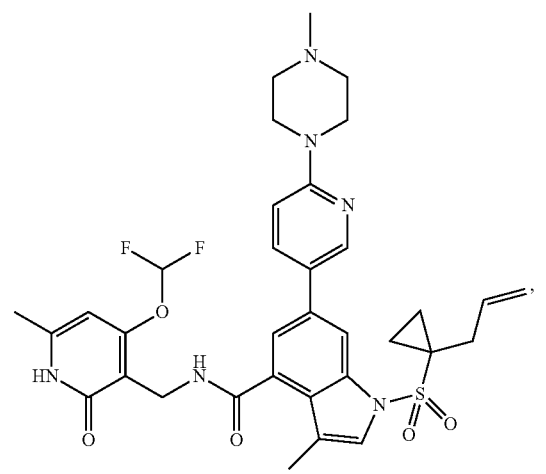 [SMILES: C=CCC1(S(=O)(=O)n2cc(C)c3c(C(=O)NCc4c(OC(F)F)cc(C)[nH]c4=O)cc(-c4ccc(N5CCN(C)CC5)nc4)cc32)CC1]
TABLE A-continued
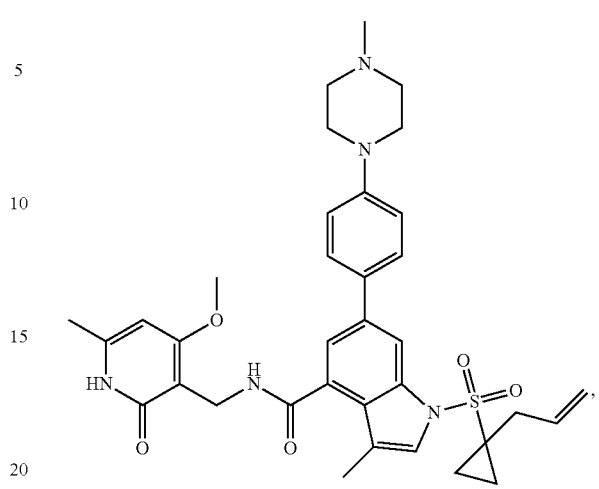
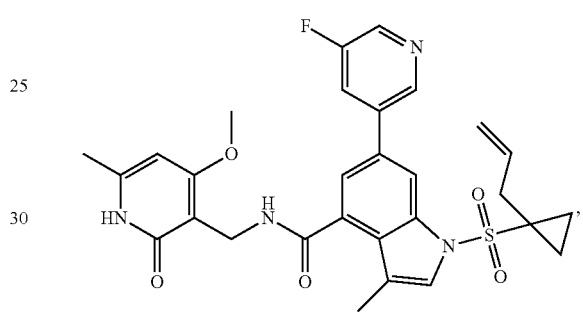
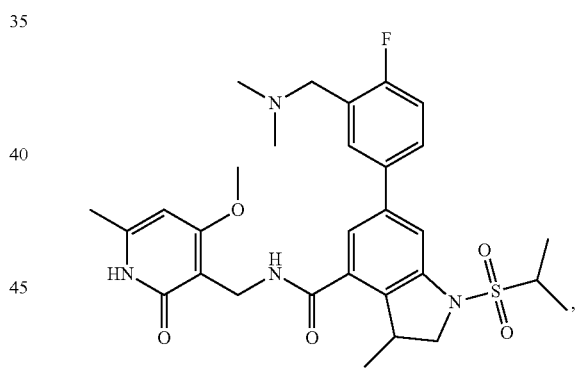
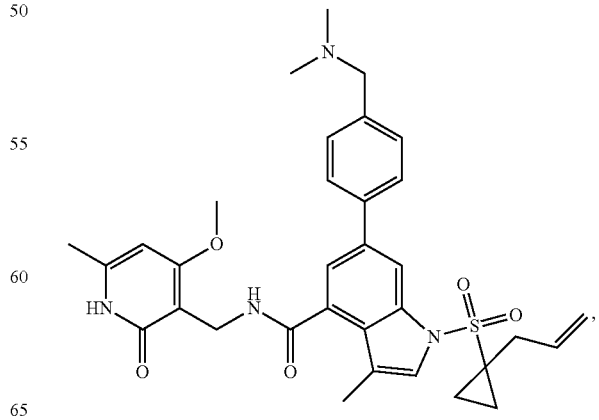

TABLE A-continued
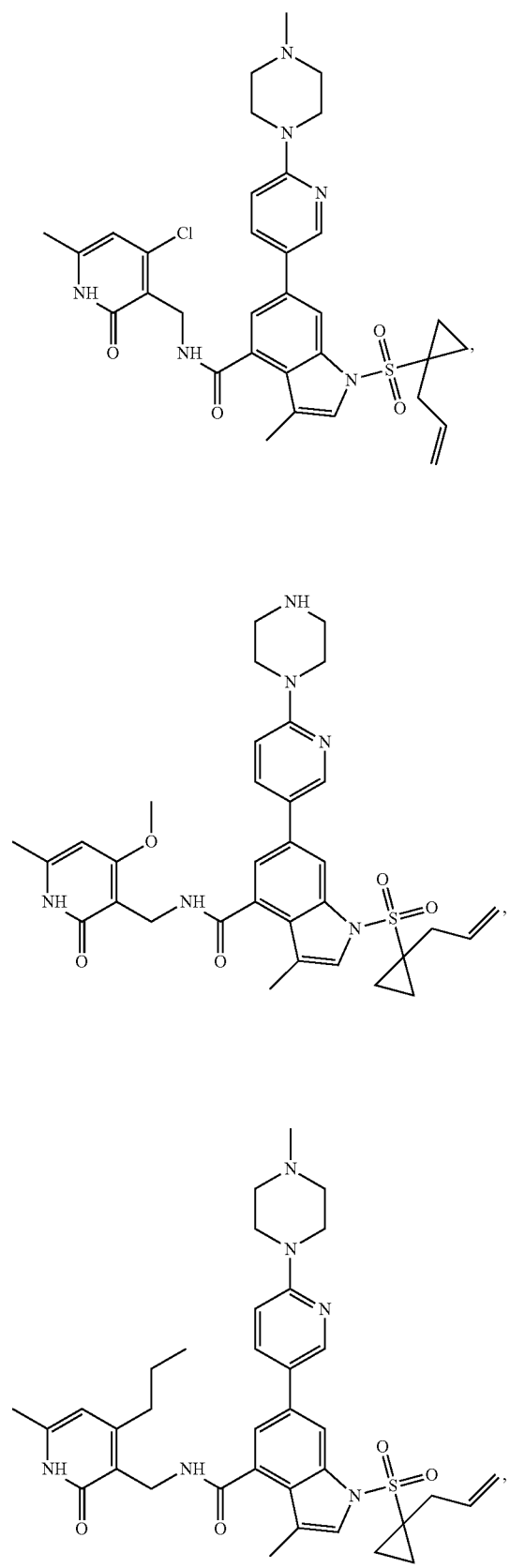
TABLE A-continued
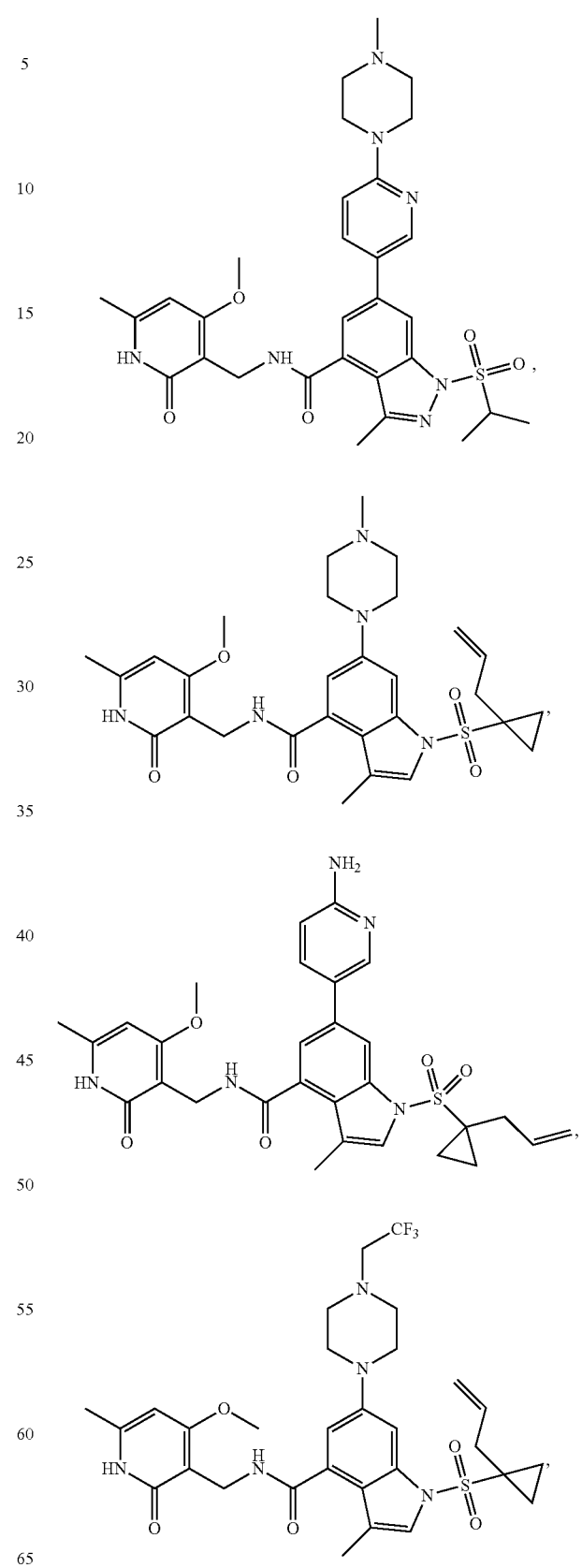

TABLE A-continued
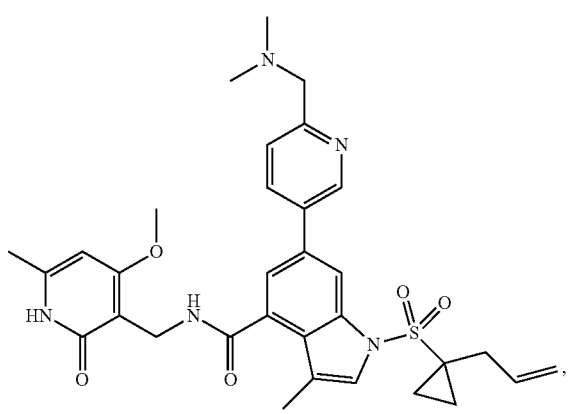 [SMILES: C=CCC1(S(=O)(=O)n2cc(C)c3c(C(=O)NCc4c(OC)cc(C)[nH]c4=O)cc(-c4ccc(CN(C)C)nc4)cc32)CC1]
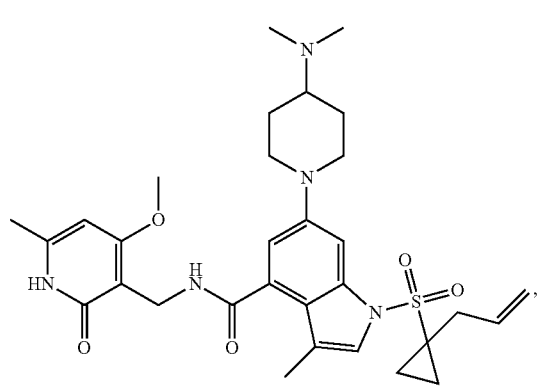 [SMILES: C=CCC1(S(=O)(=O)n2cc(C)c3c(C(=O)NCc4c(OC)cc(C)[nH]c4=O)cc(N4CCC(N(C)C)CC4)cc32)CC1]
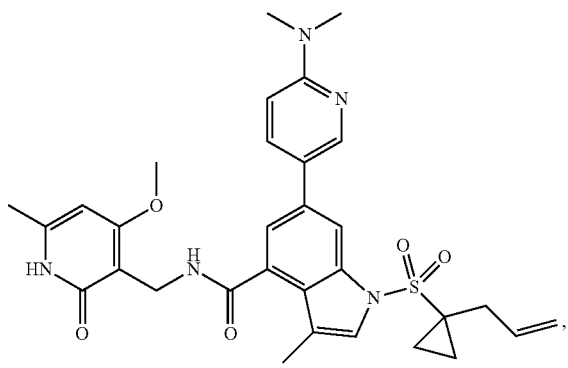 [SMILES: C=CCC1(S(=O)(=O)n2cc(C)c3c(C(=O)NCc4c(OC)cc(C)[nH]c4=O)cc(-c4ccc(N(C)C)nc4)cc32)CC1]
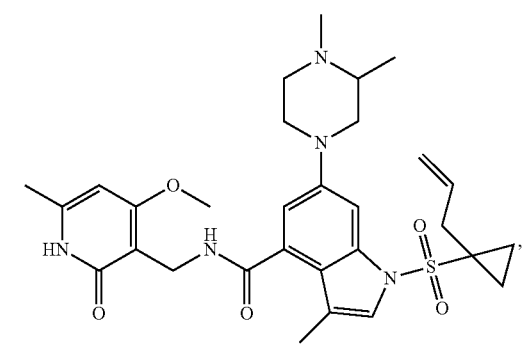 [SMILES: C=CCC1(S(=O)(=O)n2cc(C)c3c(C(=O)NCc4c(OC)cc(C)[nH]c4=O)cc(N4CCN(C)C(C)C4)cc32)CC1]
TABLE A-continued
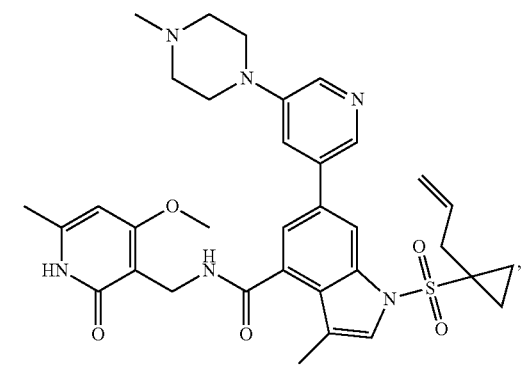 [SMILES: C=CCC1(S(=O)(=O)n2cc(C)c3c(C(=O)NCc4c(OC)cc(C)[nH]c4=O)cc(-c4cncc(N5CCN(C)CC5)c4)cc32)CC1]
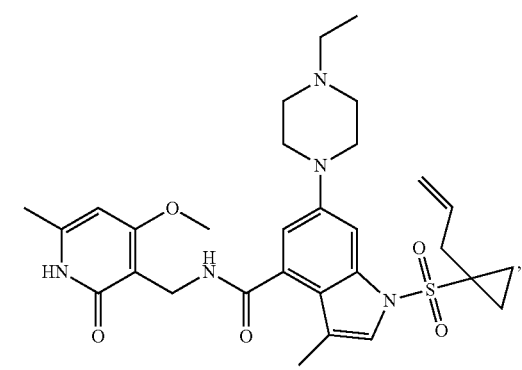 [SMILES: C=CCC1(S(=O)(=O)n2cc(C)c3c(C(=O)NCc4c(OC)cc(C)[nH]c4=O)cc(N4CCN(CC)CC4)cc32)CC1]
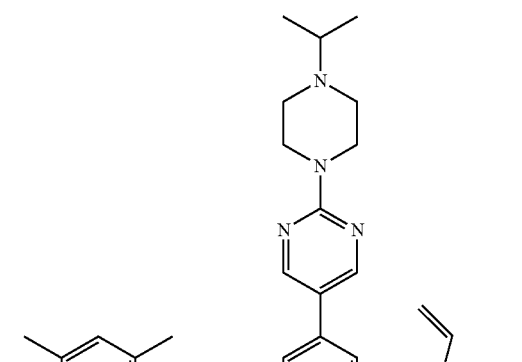
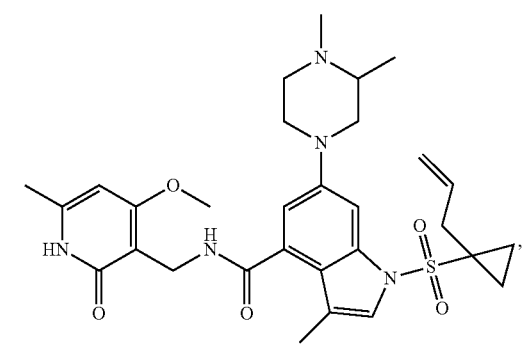 [SMILES: C=CCC1(S(=O)(=O)n2cc(C)c3c(C(=O)NCc4c(OC)cc(C)[nH]c4=O)cc(N4CCN(C)C(C)C4)cc32)CC1]

TABLE A-continued

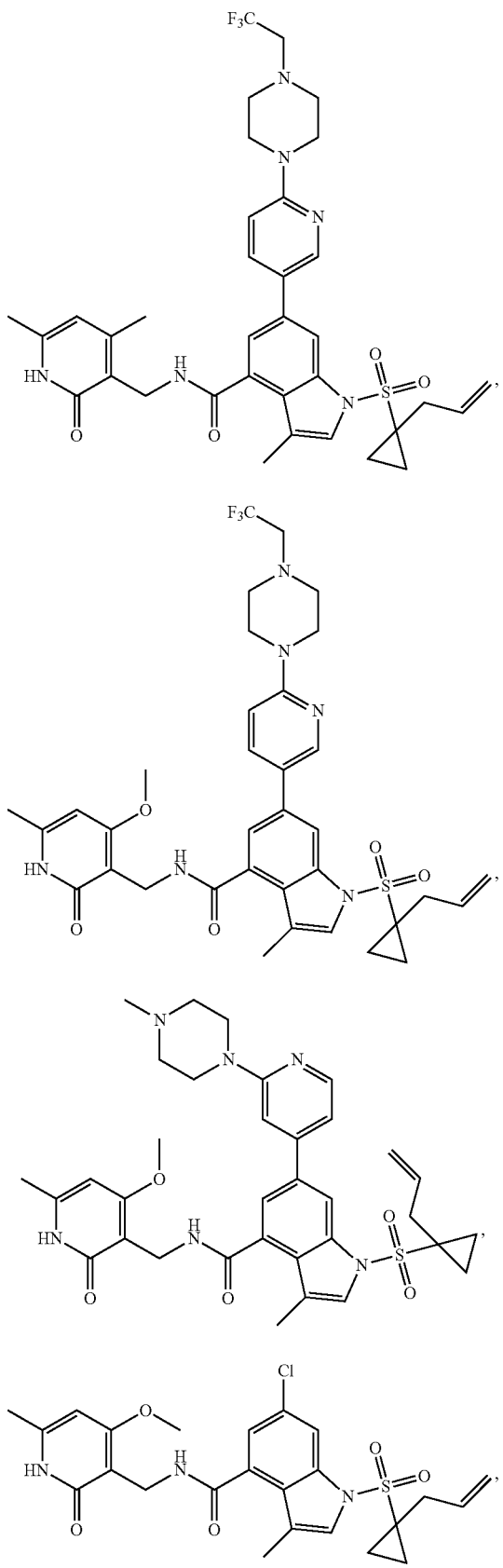

TABLE A-continued

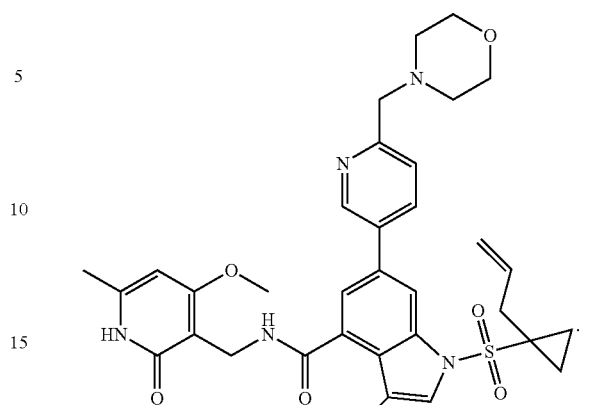

According to a second aspect of the present disclosure, a pharmaceutical composition comprising the compound of the first aspect of the present disclosure, or the pharmaceutically acceptable salt, solvate, stereoisomer or prodrug thereof; and a pharmaceutically acceptable carrier is provided.

According to a third aspect of the present disclosure, use of the compound of the first aspect of the present disclosure, or the pharmaceutically acceptable salt, solvate, stereoisomer or prodrug thereof or the pharmaceutical composition of the second aspect of the present disclosure for preparation of EZH2 inhibitors is provided.

According to a fourth aspect of the present disclosure, use of the compound of the first aspect of the present disclosure, or the pharmaceutically acceptable salt, solvate, stereoisomer or prodrug thereof or the pharmaceutical composition of the second aspect of the present disclosure for preparation of drugs for EZH2-mediated diseases or conditions is provided.

According to a fifth aspect of the present disclosure, a method of treating a disease or condition mediated by EZH2 is provided, which comprises administering to a patient in need thereof a therapeutically effective amount of the compound of the first aspect of the present disclosure, or the pharmaceutically acceptable salt, solvate, stereoisomer or prodrug thereof, or the pharmaceutical composition of the second aspect of the present disclosure.

According to a sixth aspect of the present disclosure, a method of treating a disease or condition mediated by EZH2 is provided, which comprises administering to a patient in need thereof a therapeutically effective amount of the compound of the first aspect of the present disclosure, or the pharmaceutically acceptable salt, solvate, stereoisomer or prodrug thereof, and another therapeutically active agent.

In another preferred embodiment, the disease or condition mediated by EZH2 is selected from the group consisting of cancer, pulmonary arterial hypertension, myelofibrosis, human immunodeficiency virus (HIV) disease, graft versus host disease (GVHD), Weaver syndrome, psoriasis vulgaris and liver fibrosis.

In another preferred embodiment, the disease or condition mediated by EZH2 is cancer.

In another preferred embodiment, the cancer mediated by EZH2 includes, but are not limited to, thyroid cancer, cardiac sarcoma, lung cancer, gastrointestinal cancer, genitourinary tract tumor, liver cancer, mantle cell lymphoma, osteosarcoma, nervous system sarcoma, gynecological cancer, hematological system tumor, adrenal neuroblastoma, skin cancer, astrocytic tumor, breast cancer, colorectal cancer, endometrial cancer, head and neck cancer, oral cancer.

It should be understood that each of the above technical features of the disclosure and each technical feature specifically described below (such as in Embodiments) can be combined with each other within the scope of the present disclosure so as to constitute new or preferred technical solutions which need not be specified again herein.

DETAILED DESCRIPTION OF THE EMBODIMENTS

The inventors have conducted extensive and intensive studies and have unexpectedly found that such sulfuryl-substituted benzoheterocyclic derivatives, particularly the derivatives containing the sulfuryl substituent that is substituted by the allyl-substituted cyclopropyl, have high inhibitory activities against enzymes such as EZH2 Y641F and the like, and cells such as SU-DHL-6, SU-DHL-10 cells and the like. Therefore, this series of compounds are hopefully developed as a drug for the treatment of tumors. Based on this, the inventors completed the present disclosure.

Definition of Terms

As used herein, "alkyl" refers to straight and branched saturated aliphatic hydrocarbon groups, $C_{1-8}$ alkyl is an alkyl containing 1 to 8 carbon atoms, preferably $C_{1-6}$ alkyl, more preferably $C_{1-3}$ alkyl with similar definitions; non-limiting examples of alkyl include: methyl, ethyl, n-propyl, isopropyl, n-butyl, isobutyl, tert-butyl, sec-butyl, n-pentane, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-decyl, 2-methyl-2-ethylhexyl, 2-methyl-3-ethylhexyl, 2,2-diethylpentyl, n-decyl, 3,3-diethylhexyl, 2,2-diethylhexyl, and their various branched isomers.

As used herein, "cycloalkyl" refers to a saturated or partially unsaturated monocyclic cyclic hydrocarbon group, "$C_{3-8}$ cycloalkyl" refers to a cyclic hydrocarbon group containing 3 to 8 carbon atoms, preferably a $C_{3-6}$ cycloalkyl with similar definition; non-limiting examples of cycloalkyl include cyclopropyl, cyclobutyl, cyclopentyl, cyclopentenyl, cyclohexyl, cyclohexenyl, cyclohexadienyl, cycloheptyl, cycloheptatrienyl, cyclooctyl and the like, preferably cyclopropyl, cyclopentyl, cyclohexenyl.

As used herein, "spiro" refers to a polycyclic group which shares one carbon atom (spiro atom) between the single rings. These may contain one or more double bonds, but none of the rings have a completely conjugated it electron system. According to the number of rings, the spiro is divided into bicyclic spiro or polycyclic spiro, preferably bicyclic spiro. More preferably 4 membered/5 membered, 5 membered/5 membered, or 5 membered/6 membered bicyclic spiro. For example:

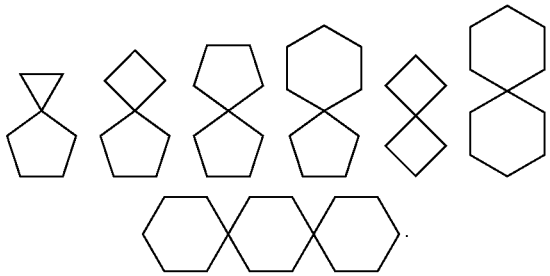

As used herein, "spiroheterocycle" refers to a polycyclic hydrocarbon which shares one atom (spiro atom) between the single rings, wherein one or two ring atoms are selected from heteroatoms such as nitrogen, oxygen, or $S(O)_n$ (wherein n is an integer from 0 to 2), the remaining ring atoms are carbon atoms. These may contain one or more double bonds, but none of the rings have a completely conjugated n-electron system. According to the number of rings, the spiroheterocycle is divided into bicyclic spiroheterocycle or polycyclic spiroheterocycle, preferably bicyclic spiroheterocycle, more preferably 4 membered/5 membered, 5 membered/5 membered, or 5 membered/6 membered bicyclic spiroheterocycle. For example:

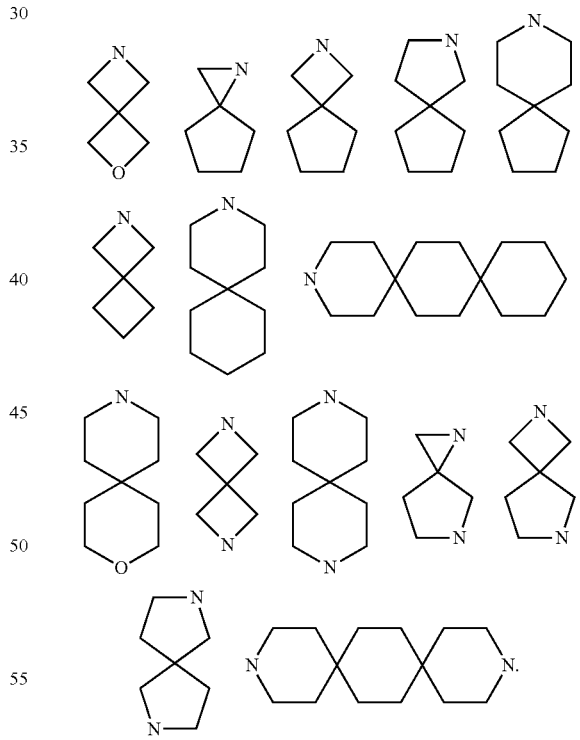

As used herein, "bridged ring" refers to a polycyclic group which shares two or more carbon atoms. The shared carbon atoms are known as bridgehead carbons. A carbon chain or a bond known as the bridge may be between two bridgehead carbons. These may contain one or more double bonds, but none of the rings have a completely conjugated i-electron system. Bicyclic or tricyclic bridged rings are preferred. For example:

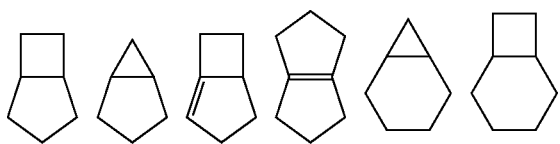

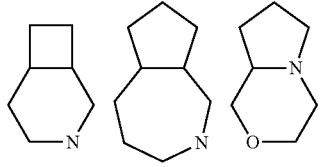

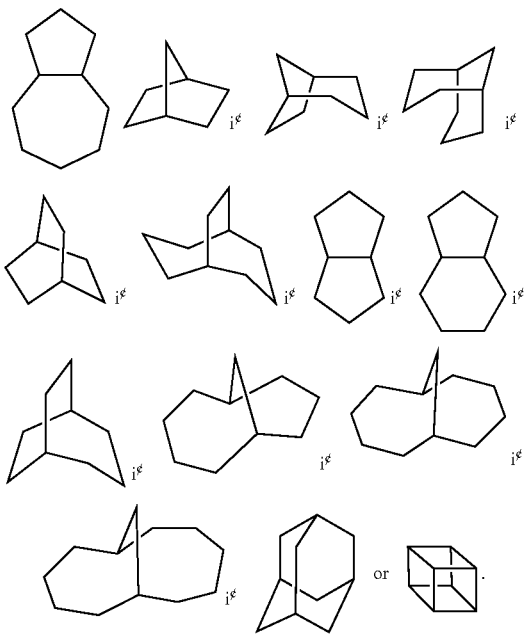

As used herein, "bridged heterocycle" refers to a polycyclic group that shares two or more atoms, wherein one or more ring atoms are selected from heteroatoms such as nitrogen, oxygen, or S(O)$_n$ (wherein n is an integer from 0 to 2), and the remaining ring atoms are carbon atoms. These may contain one or more double bonds, but none of the rings have a completely conjugated π-electron system. Bicyclic or tricyclic bridged heterocycles are preferred. For example:

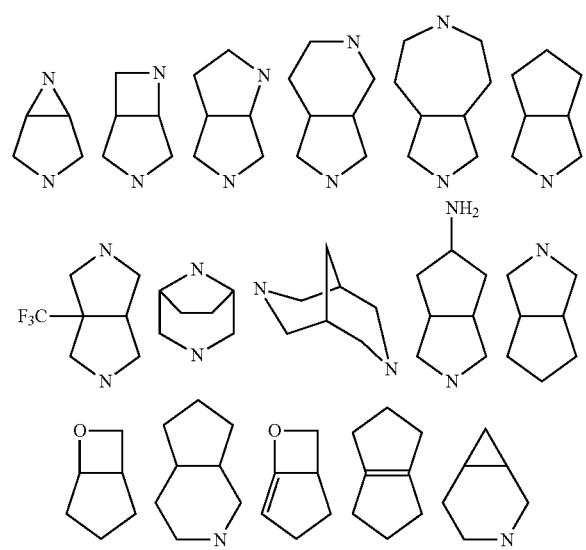

As used herein, "8 to 10 membered bicyclic ring" refers to a bridged ring with two rings containing 8 to 10 ring atoms. The bicyclic ring may be a saturated full-carbon bicyclic or partially unsaturated full-carbon bicyclic ring. Examples of 8 to 10 membered bicyclic ring include (but not limited to):

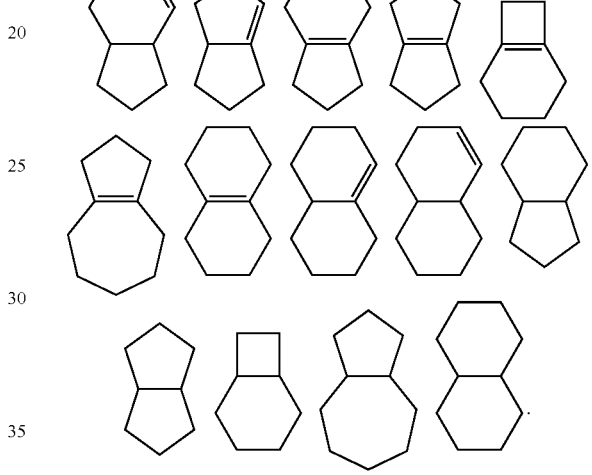

As used herein, "8 to 10 membered bicyclic heterocycle" refers to a bridged heterocycle with two rings containing 8 to 10 ring atoms, wherein 1, 2, 3, 4 or 5 carbon ring atoms are replaced by heteroatoms selected from nitrogen, oxygen or sulfur. Examples of 8 to 10 membered bicyclic heterocycles include, but are not limited to, tetrahydroquinoline ring, tetrahydroisoquinoline ring, decahydroquinoline ring, and the like.

As used herein, "$C_{1-8}$ alkoxy" refers to —O—($C_{1-8}$ alkyl), wherein alkyl is as defined above. $C_{1-6}$ alkoxy is preferred, and $C_{1-3}$ alkoxy is more preferred. Non-limiting examples include methoxy, ethoxy, propoxy, isopropoxy, butoxy, tert-butoxy, isobutoxy, pentoxy, and the like.

As used herein, "$C_{3-8}$ cycloalkoxy" refers to —O—($C_{3-8}$ cycloalkyl), wherein cycloalkyl is as defined above. $C_{3-6}$ cycloalkoxy is preferred. Non-limiting examples include cyclopropyloxy, cyclobutyloxy, cyclopentoxy, cyclohexyloxy, etc.

As used herein, "$C_{6-10}$ aryl" refers to a full-carbon monocyclic or fused polycyclic (i.e., ring that shares an adjacent pair of carbon atoms) group having a conjugated π-electron system, and refers to an aryl containing 6 to 10 carbon atoms; a phenyl and a naphthyl are preferred, a phenyl is more preferred.

As used herein, "a bond" means that two connected groups are linked by a covalent bond.

As used herein, "halogen" refers to fluorine, chlorine, bromine, or iodine.

As used herein, "halogenated" means that one or more (e.g., 1, 2, 3, 4 or 5) hydrogens in a group are substituted by a halogen.

For example, "halogenated $C_{1-8}$ alkyl" means that the alkyl is substituted by one or more (e.g., 1, 2, 3, 4 or 5) halogens, wherein the alkyl is as defined above. Halogenated $C_{1-6}$ alkyl is preferred, halogenated $C_{1-3}$ alkyl is more preferred. Examples of halogenated $C_{1-8}$ alkyl include, but not limited to, monochloromethyl, dichloromethyl, trichloromethyl, monochloroethyl, 1,2-dichloroethyl, trichloroethyl, monobromoethyl, monofluoromethyl, difluoromethyl, trifluoromethyl, monofluoroethyl, difluoroethyl, trifluoroethyl, and the like.

For another example, "halogenated $C_{1-8}$ alkoxy" means that the alkoxy is substituted by one or more (e.g., 1, 2, 3, 4 or 5) halogens, wherein the alkoxy is as defined above. Halogenated $C_{1-6}$ alkoxy is preferred, and halogenated $C_{1-3}$ alkoxy is more preferred, including, but not limited to, trifluoromethoxy, trifluoroethoxy, monofluoromethoxy, monofluoroethoxy, difluoromethoxy, difluoroethoxy, and the like.

For another example, "halogenated $C_{3-8}$ cycloalkyl" means that a cycloalkyl is substituted by one or more (e.g., 1, 2, 3, 4 or 5) halogens, wherein the cycloalkyl is as defined above. Halogenated $C_{3-6}$ cycloalkyl is preferred, including, but not limited to, trifluorocyclopropyl, monofluorocyclopropyl, monofluorocyclohexyl, difluorocyclopropyl, difluorocyclohexyl and the like.

As used herein, "deuterated $C_{1-8}$ alkyl" means that an alkyl is substituted by one or more (e.g., 1, 2, 3, 4, or 5) deuterium atoms, wherein the alkyl is as defined above. Deuterated $C_{1-6}$ alkyl is preferred, deuterated $C_{1-3}$ alkyl is more preferred. Examples of deuterated $C_{1-20}$ alkyl include, but not limited to, monodeuterated methyl, monodeuterated ethyl, dideuterated methyl, dideuterated ethyl, trideuterated methyl, trideuterated ethyl and the like.

As used herein, "amino" refers to NH2, "cyano" refers to CN, "nitro" refers to $NO_2$, "benzyl" refers to —$CH_2$-phenyl, "oxo" refers to =O, "carboxyl" refers to —C(O)OH, "acetyl" refers to —C(O)$CH_3$, "hydroxymethyl" refers to —$CH_2$OH, "hydroxyethyl" refers to —$CH_2CH_2$OH, "hydroxy" refers to —OH, "thiol" refers to SH, and the structure of "cyclopropylene" is:

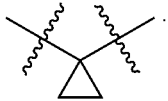

As used herein, "heteroaryl ring" and "heteroaryl" can be used interchangeably, and refer to a monocyclic heteroaryl having 5 to 10 ring atoms, preferably 5 or 6 membered monocyclic heteroaryl, or 8 to 10 membered bicyclic heteroaryl; 6,10 or 14 π electrons are shared in the ring array; and have 1 to 5 heteroatoms in addition to the carbon atom. "Heteroatom" refers to nitrogen, oxygen or sulfur.

As used herein, "3 to 6 membered saturated or partially unsaturated monocyclic ring" refers to a saturated or partially unsaturated full-carbon monocyclic ring containing 3 to 6 ring atoms. Examples of 3 to 6 membered saturated or partially unsaturated monocyclic rings include, but not limited to, cyclopropyl ring, cyclobutyl ring, cyclopentyl ring, cyclopentenyl ring, cyclohexyl ring, cyclohexenyl ring, cyclohexadienyl ring, cycloheptyl ring, cycloheptatrienyl ring, cyclooctyl ring and the like.

As used herein, "3 to 6 membered saturated or partially unsaturated single heterocycle" means that 1, 2 or 3 carbon atoms in a 3 to 6 membered monocyclic ring are substituted by heteroatoms selected from nitrogen, oxygen, or S(O)$_t$ (wherein t is an integer from 0 to 2), but the part of the ring of —O—O—, —O—S— or —S—S— is not included, the remaining ring atoms are carbon; 4 to 6 membered is preferred, 5 to 6 membered is more preferred. Examples of 3 to 6 membered saturated single heterocycles include, but not limited to, epoxypropane, azetidine, oxetane, tetrahydrofuran, tetrahydrothiophene, tetrahydropyrrole, piperidine, pyrroline, oxazolidine, piperazine, dioxolane, dioxane, morpholine, thiomorpholine, thiomorpholine-1,1-dioxide, tetrahydropyran and the like.

As used herein, "5 to 6 membered single heteroaryl ring" refers to a single heteroaryl ring containing 5 to 6 ring atoms, examples include but not limited to, thiophene ring, N-alkylpyrrole ring, furan ring, thiazole ring, imidazole ring, oxazole ring, pyrrole ring, pyrazole ring, triazole ring, tetrazole ring, isoxazole ring, oxadiazole ring, thiadiazole ring, pyridine ring, pyridazine ring, pyrimidine ring, pyrazine ring and the like.

As used herein, "8 to 10 membered bicyclic heteroaryl ring" refers to a bicyclic heteroaryl ring containing 8 to 10 ring atoms, including, for example, but not limited to, benzofuran, benzothiophene, indole, isoindole, quinoline, isoquinoline, indazole, benzothiazole, benzimidazole, quinazoline, quinoxaline, cinnoline, phthalizine.

As used herein, "substituted" means that one or more hydrogen atoms, preferably 1-5 hydrogen atoms in a group are independently substituted by a corresponding number of substituents, and more preferably 1 to 3 hydrogen atoms are independently substituted by a corresponding number of substituents. It goes without saying that the substituents are only in their possible chemical positions, and those skilled in the art can determine (by experiment or theory) the possible or impossible substitutions without undue effort. For example, an amino or hydroxy with a free hydrogen may be unstable when combined with a carbon atom having an unsaturated (e.g. olefinic) bond.

As used herein, any one of the groups herein may be substituted or unsubstituted. When the above groups are substituted, the substituents are preferably 1 to 5 groups independently selected from the group consisting of CN, halogen, $C_{1-8}$ alkyl (preferably $C_{1-6}$ alkyl, more preferably $C_{1-3}$ alkyl), $C_{1-8}$ alkoxy (preferably $C_{1-6}$ alkoxy, more preferably $C_{1-3}$ alkoxy), halogenated $C_{1-8}$ alkyl (preferably halogenated $C_{1-6}$ alkyl, more preferably halogenated $C_{1-3}$ alkyl), $C_{3-8}$ cycloalkyl (preferably $C_{3-6}$ cycloalkyl), halogenated $C_{1-8}$ alkoxy (preferably halogenated $C_{1-6}$ alkoxy, more preferably halogenated $C_{1-3}$ alkoxy), amino substituted by $C_{1-8}$ alkyl, amino, amino substituted by halogenated $C_{1-8}$ alkyl, 4 to 6 membered saturated single heterocycle, 5 to 6 membered single heteroaryl ring, 8 to 10 membered bicyclic heteroaryl ring, spiro, spiroheterocycle, bridged ring and bridged heterocycle.

The above-mentioned various substituents themselves of the present disclosure can also be substituted by the groups described herein.

When 4 to 6 membered saturated single heterocycles described herein are substituted, the positions of the substituents may be at their possible chemical positions, and representative substitutions of the exemplary single heterocycles are shown below:

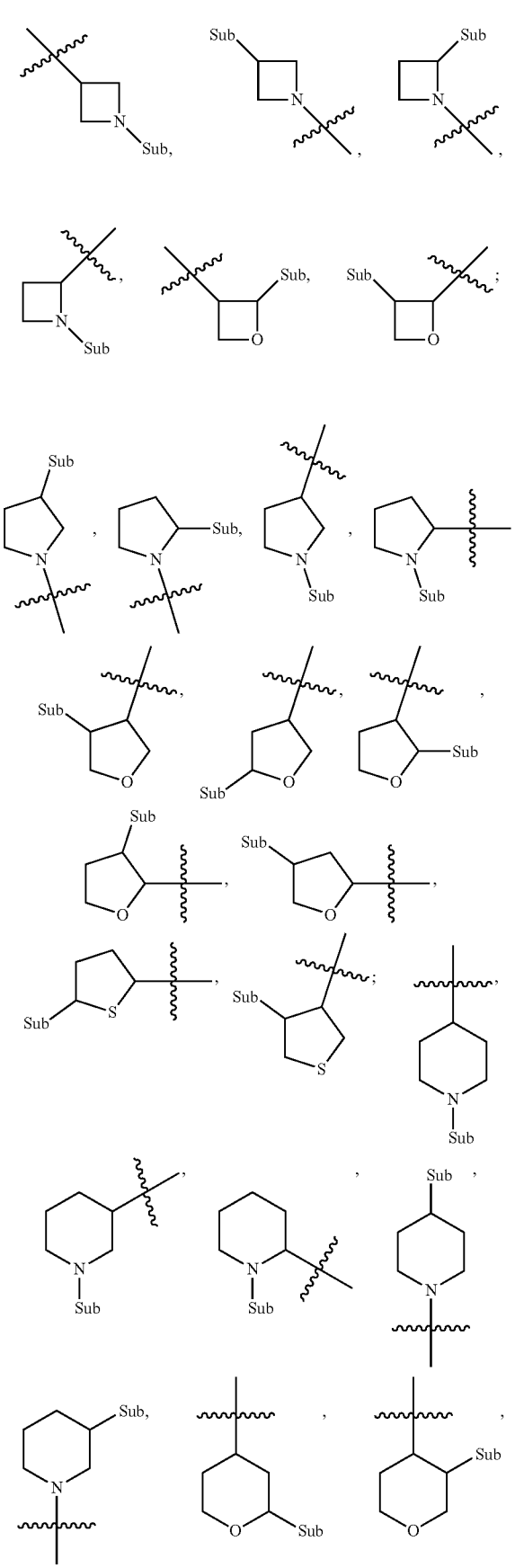
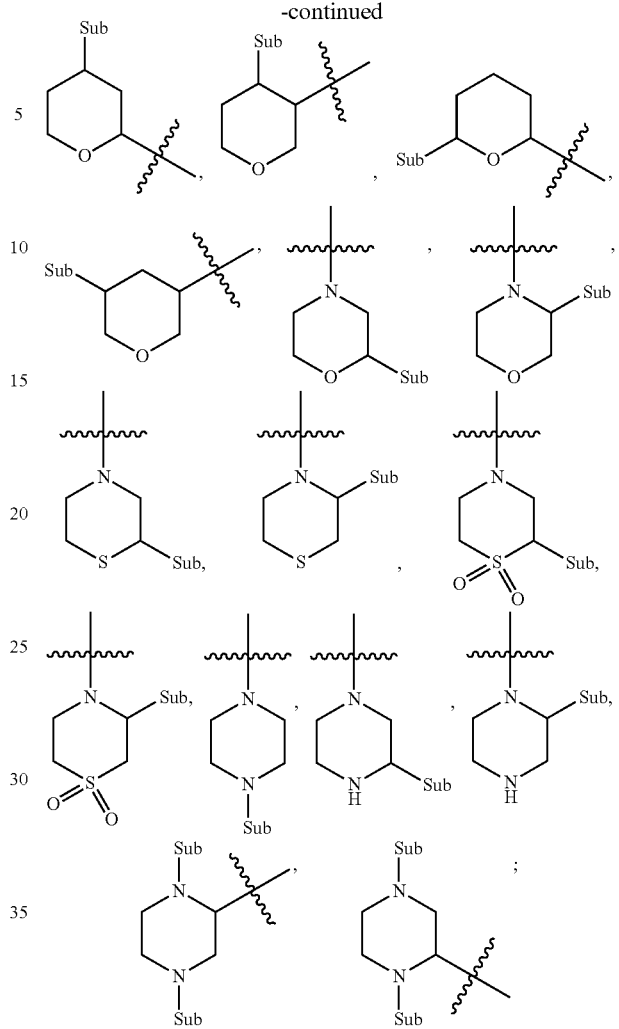

wherein "Sub" represents the various types of substituents described herein; "∼∼" represents connections with other atoms.

As used herein, "EZH2 inhibitor" refers to an agent that can inhibit increased expression of the histone lysine N-methyltransferase EZH2 (refers to a compound of formula (I) in the present disclosure) and is a catalytic functional subunit of PRC2, and is responsible for Lys27 methylation of specific histone H3 (H3K27) and indispensable for stem cell self-renewal.

As used herein, "disease or condition mediated by EZH2" refers to an abnormal epigenetic modification resulting from abnormal expression of the histone lysine N-methyltransferase EZH2, and thereby resulting in an abnormal condition in the patient.

As used herein, "therapeutically effective amount" refers to an amount of the compound of the present disclosure that will elicit the biological or medical response to an individual, for example, reduction or inhibition of an enzyme or a protein activity, or amelioration of a symptom, alleviation of a condition, slowing or delaying disease progression, or prevention of a disease, etc.

As used herein, "pharmaceutically acceptable carrier" refers to a non-toxic, inert, solid, semi-solid substance or liquid filler, diluent, encapsulating material or auxiliary formulation or any type of excipient that is compatible with the patient who is preferably a mammal and more preferably a human. It is suitable for delivering an active agent to a target without stopping the activity of the agent.

As used herein, "patient" refers to an animal, preferably a mammal, and more preferably a human. The term "mammal" refers to a warm-blooded vertebrate mammal, including, for example, cat, dog, rabbit, bear, fox, wolf, monkey, deer, rat, pig and human.

As used herein, "treating" refers to alleviating, delaying progression, attenuating, preventing, or maintaining an existing disease or condition (eg, cancer). Treatment also includes curing one or more symptoms of the disease or condition, preventing its development or reducing to some extent.

Preparation Method

A method of preparing the compound of formula (I) is provided in the present disclosure, the compound of the present disclosure can be prepared by a variety of synthetic operations, exemplary methods of preparing these compounds may include (but not limited to) the processes described below.

Preferably, the compound of formula (I) can be prepared through the following schemes and exemplary methods described in embodiment, as well as the related publications available for those skilled in the art.

In the specific operation process, the steps of method can be extended or combined as required.

Scheme 1:

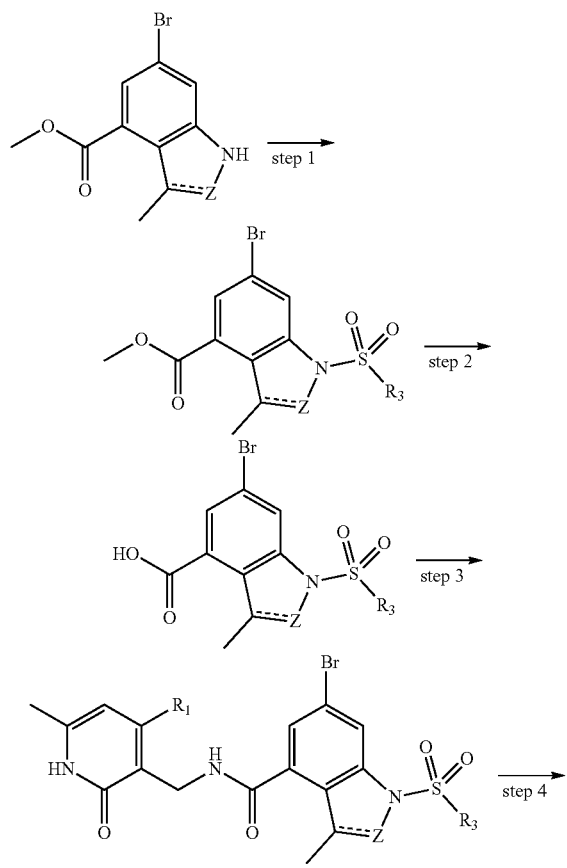

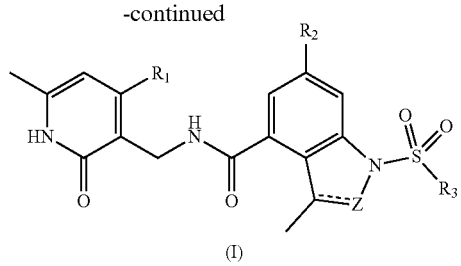

(I)

Step 1: The indole or indazole compounds can be dehydrogenated under alkaline conditions and then engaged in nucleophile substitution reaction with sulfonyl chloride. The base used can be, but is not limited to, sodium hydride.

Step 2: Hydrolysis of the ester, the compound can be hydrolyzed in for example an alkaline solution of methanol to give the carboxylic acid compound. The base used can be, but is not limited to, lithium hydroxide.

Step 3: The carboxylic acid compound can be condensed with the corresponding amine under alkaline conditions to synthesize an amide, or the condensation reaction was completed in the presence of a condensing agent.

Step 4: The indole or indazole compounds (which can be a bromide or a boron ester compound of bromide) can be engaged in Suzuki reaction with the corresponding bromides or boronate compounds using a suitable catalyst and an appropriate solvent at a given temperature. The reaction may be, but is not limited to, a microwave reaction; the palladium catalyst used may be, but is not limited to Pd(dppf)Cl$_2$, and the base used may be, but is not limited to, cesium fluoride. Alternatively, halogen atoms of the indole or indazole compounds may be engaged in Buchwald reaction with the corresponding amines under the catalysis of palladium catalysts, the reaction may be, but is not limited to, a microwave reaction; the palladium catalyst used may be but is not limited to Pd$_2$(dpa)$_3$, and the base used may be but not limited to sodium tert-butoxide.

The reactions in the above steps are all conventional reactions known to those skilled in the art. Unless otherwise specified, the reagents and raw material compounds used in the synthetic route are all commercially available, or can be prepared by those skilled in the art by referring to known methods according to the different compound structures designed.

Compared with the prior art, the main advantages of the present disclosure are to provide a series of novel sulfuryl-substituted benzoheterocyclic derivatives which have high inhibitory activity against EZH2 and can be used as drugs for the treatment of tumors.

The present disclosure will be further illustrated below with reference to the specific embodiments. It should be understood that these embodiments are only to illustrate the disclosure but not to limit the scope of the disclosure. The experimental methods without specific conditions in the following embodiments are generally carried out according to conventional conditions, or in accordance with the conditions recommended by the manufacturer. Unless indicated otherwise, parts and percentage are calculated by weight. Unless otherwise defined, terms used herein are of the same meanings that are familiar to those skilled in the art. In addition, any methods and materials similar with or equivalent to those described herein can be applied to the present disclosure.

As used herein, DMB refers to 2,4-dimethoxybenzyl, THF refers to tetrahydrofuran, EA refers to ethyl acetate, PE refers to petroleum ether, Ac$_2$O refers to acetic anhydride, NBS refers to N-bromosuccinimide, DCM refers to dichloromethane, AIBN refers to azodiisobutyronitrile, Pd(dppf)Cl$_2$ refers to [1,1'-bis(diphenylphosphino)ferrocene]palladium dichloride, TFA refers to trifluoroacetic acid, TBSCl refers to tert-butyldimethylchlorosilane, NCS refers to N-chlorosuccinimide, DHP refers to dihydrogenpyran, LiAlH$_4$ refers to lithium aluminium hydride, PMB refers to p-methoxybenzyl, LiHMDS refers to lithium bistrimethylsilylamide, Pd$_2$(dba)$_3$ refers to tris(dibenzylideneacetone)dipalladium, RuPhos refers to 2-dicyclohexylphosphoryl-2', 6'-diisopropoxy-1,1'-biphenyl, DMAP refers to 4-dimethylaminopyridine, THP refers to tetrahydropyran, n-BuLi refers to n-butyllithium, TMsOTf refers to trimethylsilyl trifluoromethanesulfonate, TEBAC refers to triethylbenzylammonium chloride, HATU refers to 2-(7-azobenzotriazole)-N,N,N',N'-tetramethyluronium hexafluorophosphate, DMF refers to dimethylformamide, DMSO refers to dimethylsulfoxide, DIEA refers to N,N-diisopropylethylamine, BINAP refers to (2R,3S)-2,2'-bis diphenylphosphino-1,1'-binaphthyl.

As used herein, room temperature refers to about 20-25° C.

Preparation of Intermediate 1a

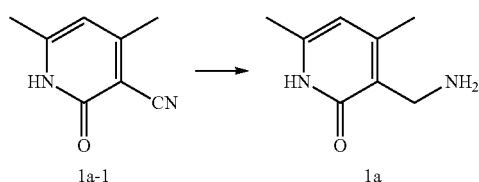

To a solution of compound 1a-1 (22.5 g, 152 mmol) in tetrahydrofuran (500 mL) was slowly added lithium aluminum hydride (11.5 g, 0.3 mol) under ice-bath, and the mixture was stirred at room temperature overnight. 15 mL of water and 30 mL of sodium hydroxide solution (15%) were added to the system respectively, then the system was filtered, and the filtrate was concentrated to give white solid compound 1a. MS m/z (ESI): N/A.

Preparation of Intermediate 2a

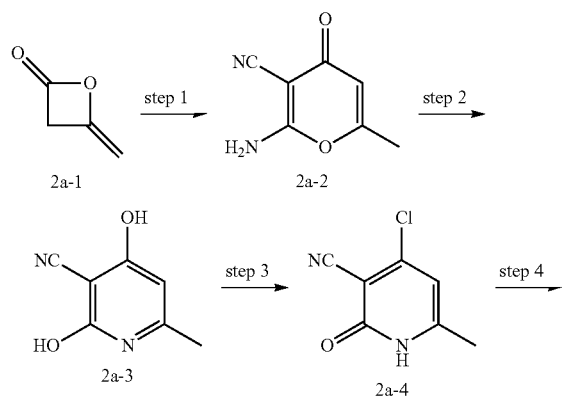

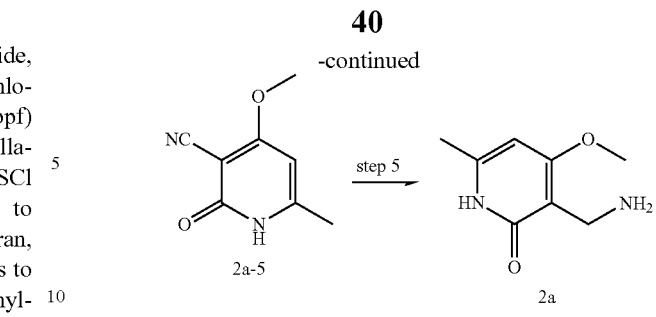

Step 1: A solution of compound malononitrile (12 g, 181.7 mmol) in dry tetrahydrofuran (225 mL) was stirred under an ice bath for 1 hour, sodium hydride (4.8 g, 199.8 mmol) was added in batchs and stirred for 2 hours, compound 2a-1 (16.8 g, 199.8 mmol) was added dropwise, the mixture was slowly warmed to room temperature and reacted for 1 hour. The reaction solution was quenched with hydrochloric acid solution, extracted with ethyl acetate, and the organic layer was dried and concentrated to give a yellow solid compound 2a-2 used directly for the next step. MS m/z (ESI): 151 [M+H]$^+$.

Step 2: A mixture of compound 2a-2 (28 g, 181.7 mmol), hydrochloric acid (23.2 g, 4 M, 636.4 mmol) and water (160 mL) was stirred under reflux for 5 hours. The reaction solution was filtered, and the solid residue was recrystallized from methanol to obtain 25 g of compound 2a-3. MS m/z (ESI): 151 [M+H]$^+$.

Step 3: To compound 2a-3 (80 mg, 0.53 mmol) was added 2 mL of phosphorus oxychloride and the mixture was stirred at 100° C. for 2 hours. LC-MS was followed until the reaction was completed. The mixture was cooled and poured into ice water. The pH was adjusted to 8 with aqueous ammonia, extracted with ethyl acetate, dried and concentrated to give 100 mg of compound 2a-4 as a white solid. MS m/z (ESI): 169 [M+H]$^+$.

Step 4: A mixture of compound 2a-4 (300 mg, 1.78 mmol), sodium methoxide (481 mg, 8.9 mmol) and methanol (15 mL) was sealed and reacted at 100° C. for 16 hours. LC-MS was followed until the reaction was completed, the reaction solution was concentrated to remove the solvent, water was added to the residues, and the pH was adjusted to 7 and filtered to give 225 mg of solid compound 2a-5. MS m/z (ESI): 419 [M+H]$^+$.

Step 5: The preparation method is the same as that of compound 1a, except that compound 1a-1 in the preparation method of 1a is replaced with compound 2a-5. MS m/z (ESI): 152 [M+H]$^+$.

Preparation of Intermediate 5a

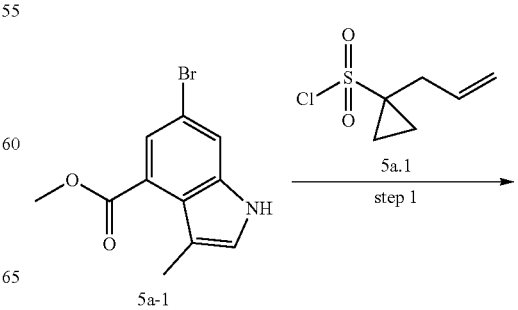

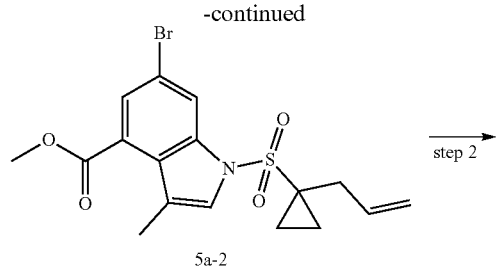

5a-2

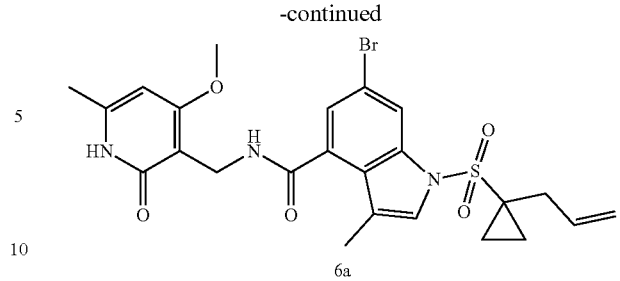

6a

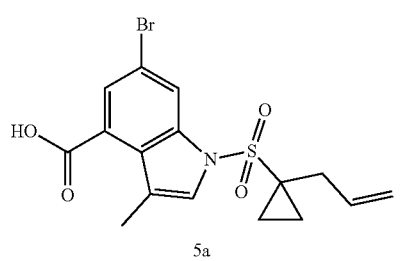

5a

Step 1: To a solution of compound 5a-1 (250 mg, 0.932 mmol) in DMF (20 mL) was added sodium hydride (80 mg, 2 mmol) under an ice bath, and the mixture was stirred under an ice bath under an argon atmosphere for 30 minutes, compound 5a.1 (300 mg, 1.661 mmol) was added. The system was stirred for 30 minutes under the ice bath. TLC was followed until the reaction was completed. The reaction solution was poured into water, extracted with ethyl acetate, concentrated and purified by combiflash (PE:EA=100:0-80:20) to give compound 5a-2 (460 mg, 93.7%). MS m/z (ESI): 426 [M+H]$^+$.

Step 2: A mixture of 5a-2 (460 mg, 1.116 mmol), hydrated lithium hydroxide (200 mg, 4.762 mmol), 10 mL of tetrahydrofuran, 3 mL of water and 10 mL of methanol was stirred at room temperature overnight. LC-MS was followed until the reaction was completed. The reaction solution was concentrated to remove tetrahydrofuran. Water was added, and the mixture was extracted with ethyl acetate. The aqueous layer was adjusted to pH 5-6 with an aqueous solution of 0.1N hydrochloric acid under an ice bath, and extracted with ethyl acetate. The organic layer was separated, washed with saturated brine, dried, and concentrated to give 370 mg of compound 5a. MS m/z (ESI): 398 [M+Na]$^+$.

Preparation of Intermediate 6a

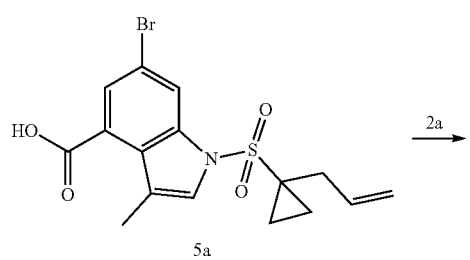

5a

To a solution of compound 5a (500 mg, 1.25 mmol) in dichloromethane (20 mL) was added compound 2a (500 mg, 2.44 mmol), EDCI (700 mg, 3.65 mmol), HOBt (600 mg, 4.44 mmol) and triethylamine (3 mL), the mixture was stirred at room temperature under argon atmosphere for 12 hours. LC-MS was followed until the reaction was completed. The reaction solution was concentrated and purified by combiflash (DCM:MeOH=100:0-90:10) to give compound 6a (200 mg, 29%).). MS m/z (ESI): 548.1 [M+H]$^+$.

Preparation of Intermediate 7a

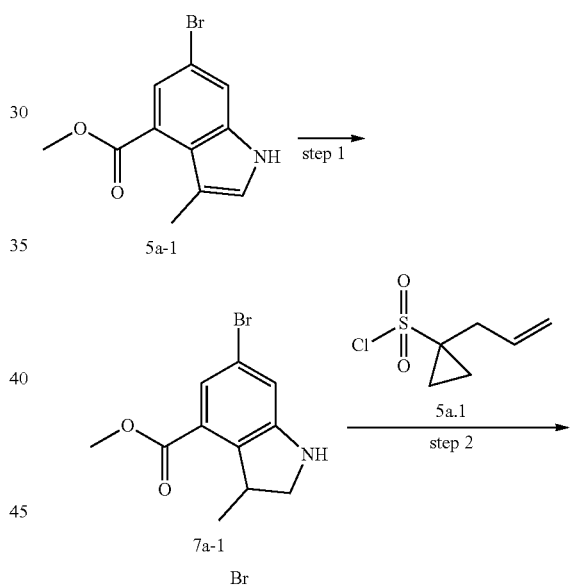

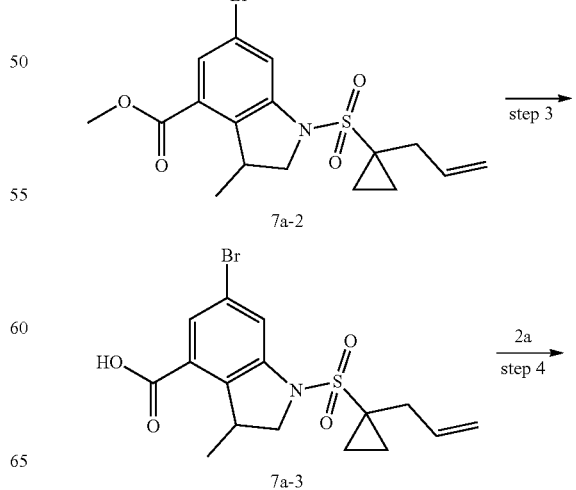

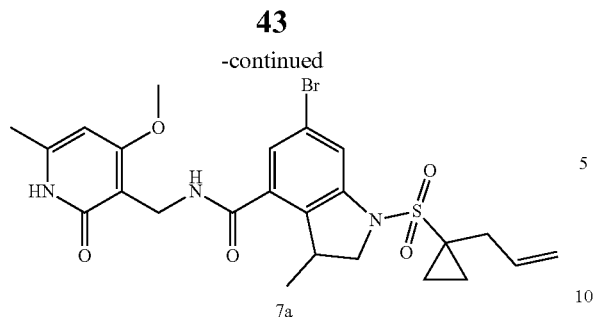

7a

Step 1: Compound 5a-1 (2.03 g, 7.42 mmol) and trifluoroacetic acid (4.33 g, 37.98 mmol) in DCE (30 mL) were cooled under an ice bath under argon atmosphere and sodium cyanoborohydride NaCNBH$_3$ (955 mg, 15.2 mmol) was added dropwise, the mixture was stirred at room temperature for 2 hours. LC-MS was followed until the reaction was completed. The reaction solution was poured into the ice water, adjusted to pH 9 with 4N sodium hydroxide solution, extracted with dichloromethane, and the organic layer was dried and concentrated, and purified by combiflash (PE:EA=100:0-90:10) to give the yellow oil compound 7a-1 (1.59 g, 79.5%). MS m/z (ESI): 272 [M+H]$^+$.

Step 2: The preparation method is the same as that of compound 5a-2, except that compound 5a-1 in the preparation method of 5a-2 is replaced with compound 7a-1. MS m/z (ESI): 414[M+H]$^+$.

Step 3: The preparation method is the same as that of compound 5a, except that compound 5a-2 in the preparation method of 5a is replaced with compound 7a-2. MS m/z (ESI): 398[M–H]$^+$.

Step 4: The preparation method is the same as that of compound 6a, except that compound 5a in the preparation method of 6a is replaced with compound 7a-3. MS m/z (ESI): 550[M+H]$^+$.

Preparation of Intermediate 8a

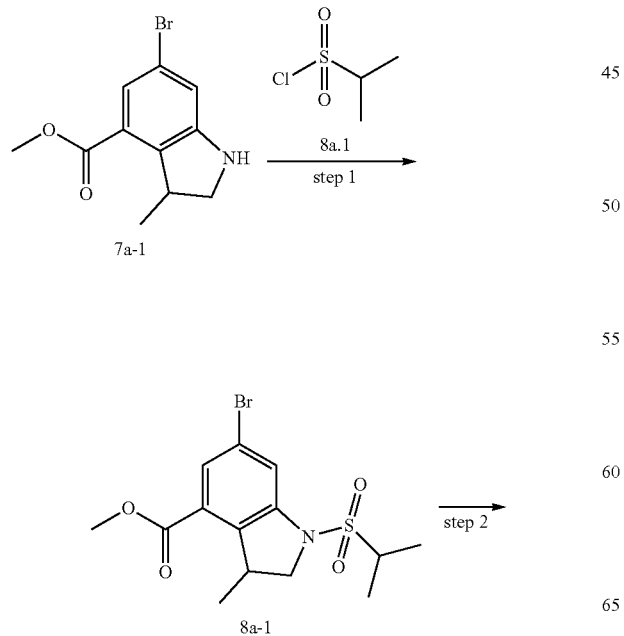

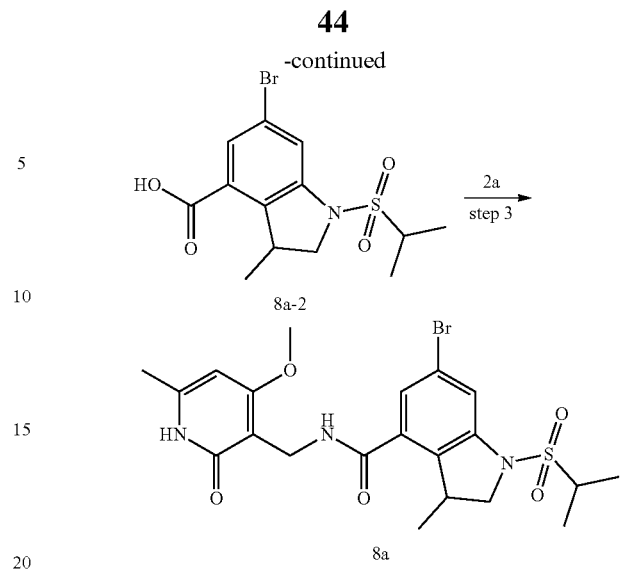

Step 1: The preparation method is the same as that of compound 5a-2, except that compound 5a.1 in the preparation method of 5a-2 is replaced with compound 8a.1. MS m/z (ESI): 376[M+H]$^+$.

Step 2: The preparation method is the same as that of compound 5a, except that compound 5a-2 in the preparation method of 5a is replaced with compound 8a-1. MS m/z (ESI): 362 [M–H]$^+$.

Step 3: The preparation method is the same as that of compound 6a, except that compound 5 in the preparation method of 6a is replaced with compound 8a-2. MS m/z (ESI): 512[M+H]$^+$.

Preparation of Intermediate 9a

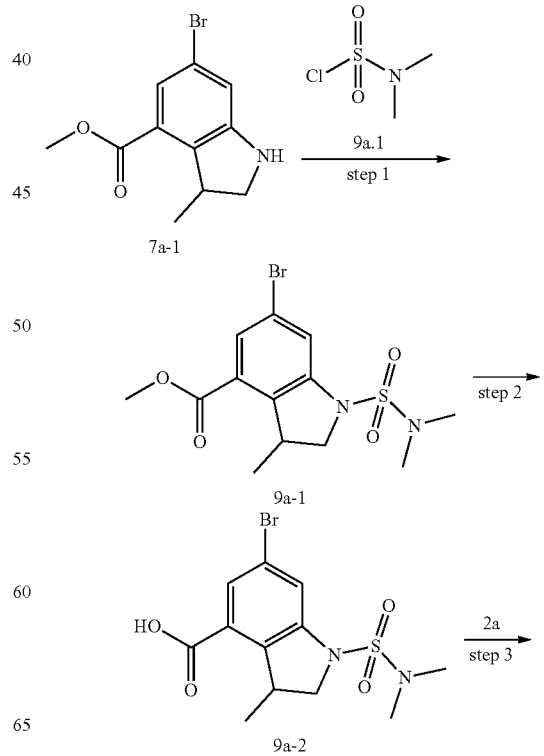

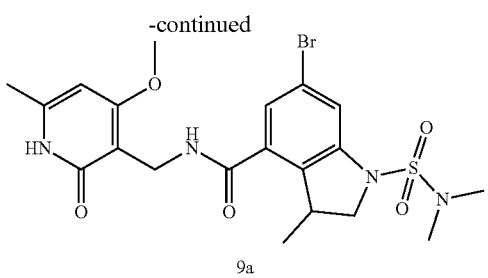

9a

Step 1: The preparation method is the same as that of compound 5a-2, except that compound 5a.1 in the preparation method of 5a-2 is replaced with compound 9a.1. MS m/z (ESI): 377[M+H]⁺.

Step 2: The preparation method is the same as that of compound 5a, except that compound 5a-2 in the preparation method of 5a is replaced with compound 9a-1. MS m/z (ESI): 363[M–H]⁺.

Step 3: The preparation method is the same as that of compound 6a, except that compound 5a in the preparation method of 6a is replaced with compound 9a-2. MS m/z (ESI): 513[M+H]⁺.

Preparation of Intermediate 10a

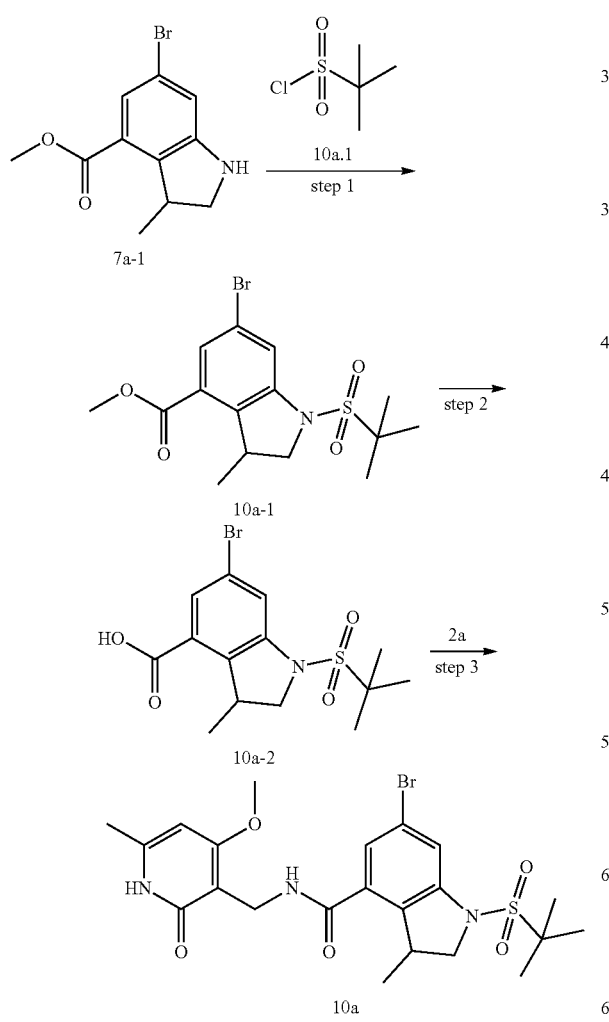

Step 1: The preparation method is the same as that of compound 5a-2, except that compound 5a.1 in the preparation method of 5a-2 is replaced with compound 10a.1. MS m/z (ESI): 374[M+H]⁺.

Step 2: The preparation method is the same as that of compound 5a, except that compound 5a-2 in the preparation method of 5a is replaced with compound 10a-1. MS m/z (ESI): 360[M–H]⁺.

Step 3: The preparation method is the same as that of compound 6a, except that compound 5a in the preparation method of 6a is replaced with compound 10a-2. MS m/z (ESI): 510[M+H]⁺.

Preparation of Intermediate 11a

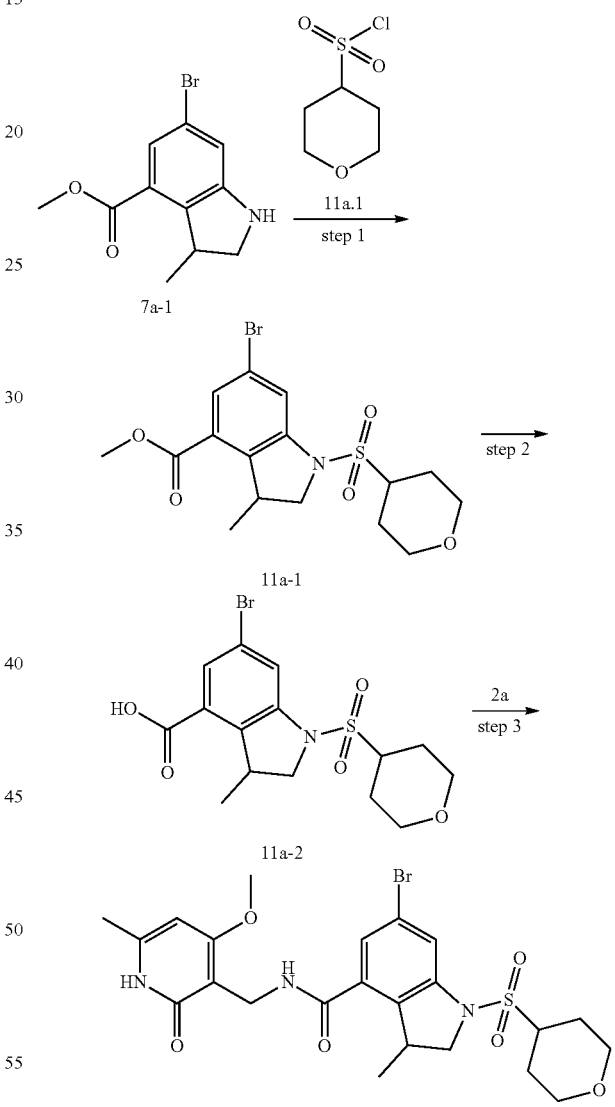

Step 1: The preparation method is the same as that of compound 5a-2, except that compound 5a.1 in the preparation method of 5a-2 is replaced with compound 11a. 1. MS m/z (ESI): 418 [M+H]⁺.

Step 2: The preparation method is the same as that of compound 5a, except that compound 5a-2 in the preparation method of 5a is replaced with compound 11a-1. MS m/z (ESI): 404[M–H]⁺.

Step 3: The preparation method is the same as that of compound 6a, except that compound 5a in the preparation method of 6a is replaced with compound 11a-2. MS m/z (ESI): 554[M+H]$^+$.

Preparation of Intermediate 12a

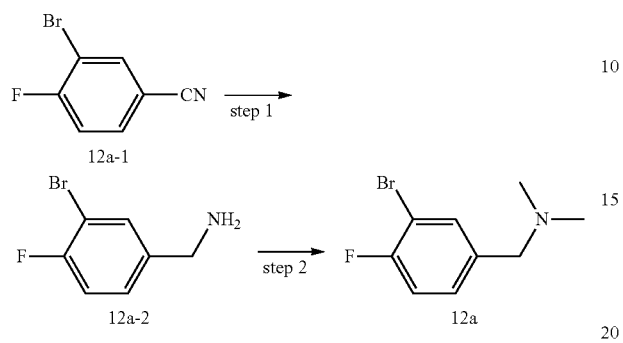

Step 1: To a solution of compound 12a-1 (2 g, 10 mmol) in THF (5 mL) was added dropwise borane-tetrahydrofuran (100 mL, 1M) at room temperature, the system was slowly raised to 85° C. and stirred for 2 hours. The mixture was cooled to room temperature, quenched with methanol and concentrate to give 1.95 g of white solid compound 12a-2. MS m/z (ESI): 204 [M+H]$^+$.

Step 2: To a solution of compound 12a-2 (200 mg, 1 mmol) in DMF (2 mL) was added formaldehyde (365 mg, 4.5 mmol) at room temperature and the system was stirred at 100° C. for 5 hours. The reaction solution was concentrated and purified by combiflash to give 100 mg of compound 12a. MS. m/z (ESI): 232 [M+H]$^+$.

Preparation of Intermediate 13a

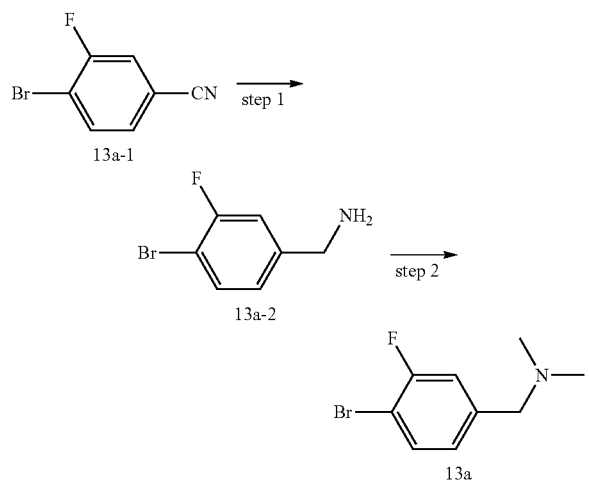

Step 1: The preparation method is the same as that of compound 12a-2, except that compound 12a-1 in the preparation method of 12a-2 is replaced with compound 13a-1. MS m/z (ESI): 204[M+H]$^+$.

Step 2: The preparation method is the same as that of compound 12a, except that compound 12a-2 in the preparation method of 12a is replaced with compound 13a-2. MS m/z (ESI): 232[M–H]$^+$.

Preparation of Intermediate 14a

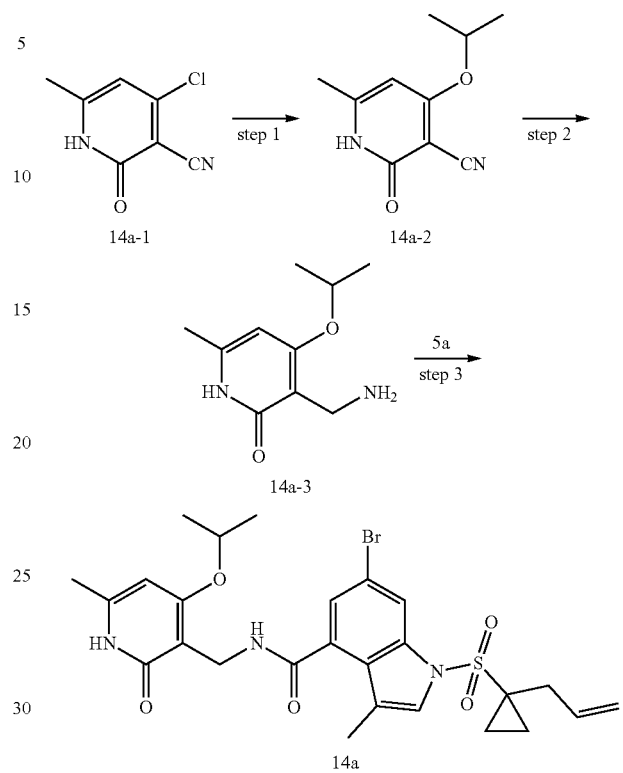

Step 1: The preparation method is the same as that of compound 2a-5, except that compound 2a-4, sodium methoxide and methanol in the preparation method of 2a-5 are replaced with compound 14a-1, sodium hydride and isopropanol respectively. MS m/z (ESI): 193[M+H]$^+$.

Step 2: The preparation method is the same as that of compound 2a, except that compound 2a-5 in the preparation method of 2a is replaced with compound 14a-2. MS m/z (ESI): 197[M+H]$^+$.

Step 3: The preparation method is the same as that of compound G-1, except that compound 1a in the preparation method of G-1 is replaced with compound 14a-3. MS m/z (ESI): 576[M+H]$^+$.

Preparation of Intermediate 15a

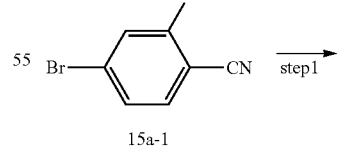

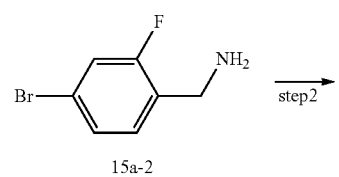

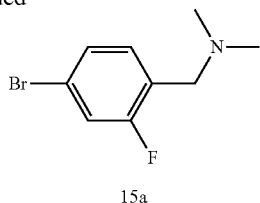

Step 1: The preparation method is the same as that of compound 12a-2, except that compound 12a-1 in the preparation method of 12a-2 is replaced with compound 15a-1. MS m/z (ESI): 204[M+H]⁺.

Step 2: The preparation method is the same as that of compound 12a, except that compound 12a-2 in the preparation method of 12a is replaced with compound 15a-2. MS m/z (ESI): 232[M−H]⁺.

Preparation of Intermediate 16a

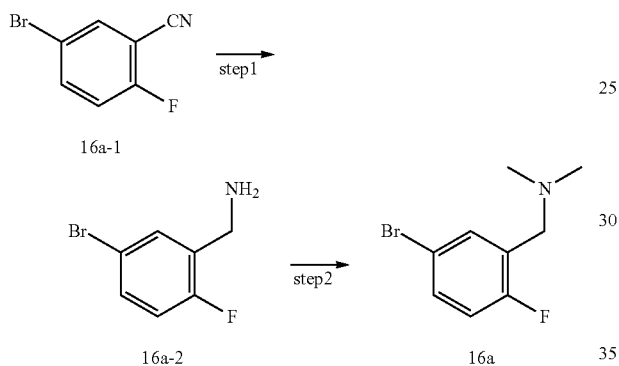

Step 1: The preparation method is the same as that of compound 12a-2, except that compound 12a-1 in the preparation method of 12a-2 is replaced with compound 16a-1. MS m/z (ESI): 204[M+H]⁺.

Step 2: The preparation method is the same as that of compound 12a, except that compound 12a-2 in the preparation method of 12a is replaced with compound 16a-2. MS m/z (ESI): 232[M−H]⁺.

Preparation of Intermediate 17a

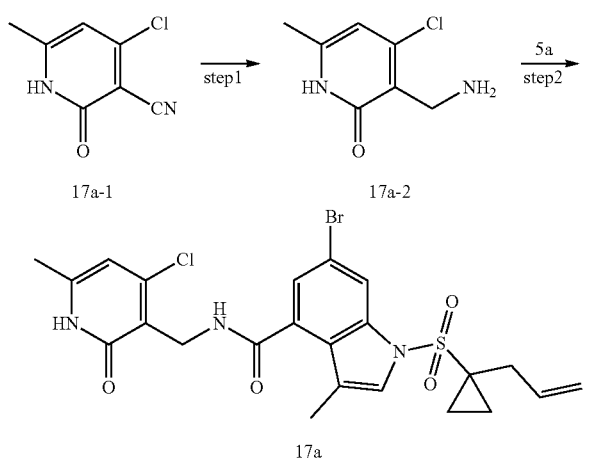

Step 1: The preparation method is the same as that of compound 12a-2, except that compound 12a-1 in the preparation method of 12a-2 is replaced with compound 17a-1. MS m/z (ESI): 173[M+H]⁺.

Step 2: The preparation method is the same as that of compound G-1, except that compound 1a in the preparation method of G-1 is replaced with compound 17a-2. MS m/z (ESI): 554[M+H]⁺.

Preparation of Intermediate 18a

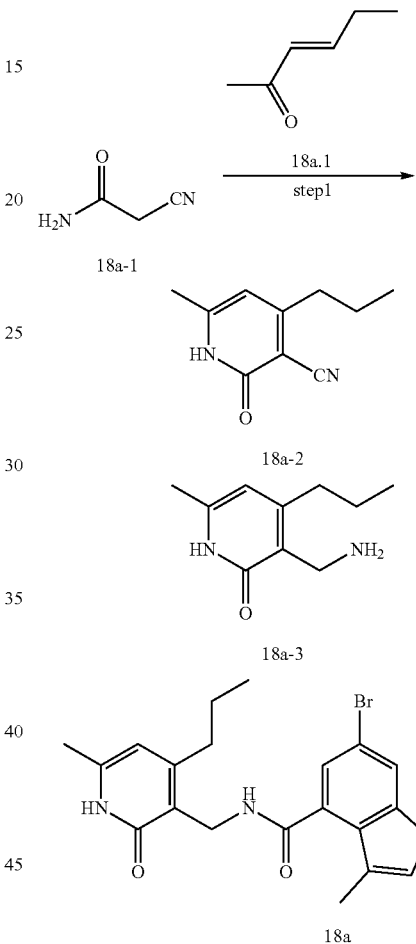

Step 1: A solution of compound 18a-1 (1.85 g, 22 mmol), 18a.1 (2.24 g, 20 mmol) and potassium tert-butoxide (11.2 g, 100 mmol) in DMSO (40 mL) was stirred at room temperature overnight under a nitrogen atmosphere. The reaction solution was quenched with 4N hydrochloric acid solution, adjusted to pH 3, filtered, and the filter cake was washed with water and ethanol to give a solid compound 18a-2. MS m/z (ESI): 177 [M+H]⁺.

Step 2: The preparation method is the same as that of compound 12a-2, except that compound 12a-1 in the preparation method of 12a-2 is replaced with compound 18a-2. MS m/z (ESI): 181 [M+H]⁺.

Step 3: The preparation method is the same as that of compound G-1, except that compound 1a in the preparation method of G-1 is replaced with compound 18a-3. MS m/z (ESI): 560[M+H]⁺.

Preparation of Intermediate 1b

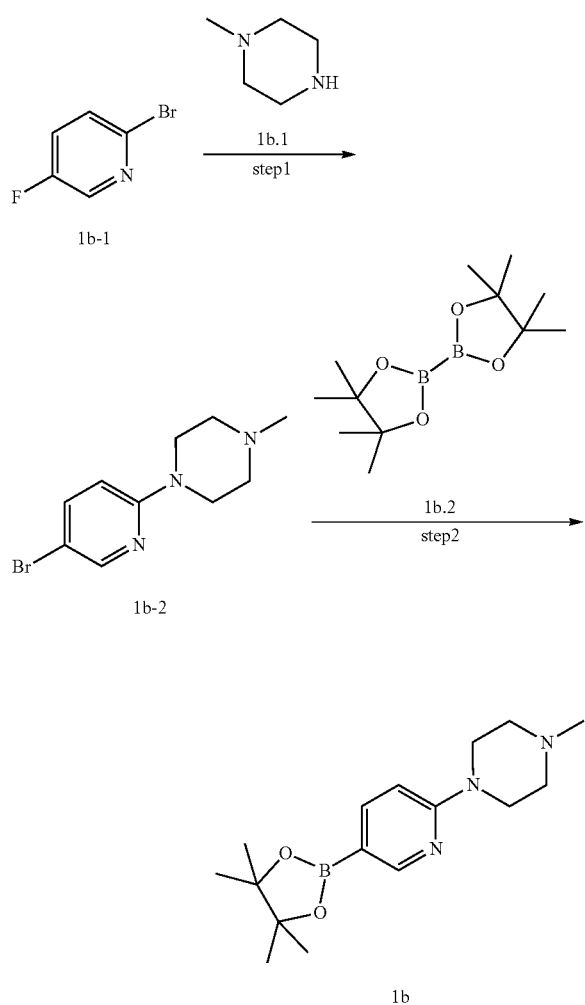

Step 1: A solution of compound 1b-1 (30 g, 170.5 mmol), 1b.1 (20.5 g, 204.5 mmol) and potassium carbonate (51.8 g, 375 mmol) in DMF (250 mL) was stirred at 100° C. overnight. The reaction solution was filtered and the filtrate was concentrated, the residue was extracted with ethyl acetate/water and the organic layer was dried and concentrated to give 38.1 g of crude product of compound 1b-2. MS m/z (ESI): 256.1 [M+H]$^+$.

Step 2: A mixture of compound 1b-2 (37.5 g, 146.4 mmol), compound Pd(dppf)Cl$_2$ (4.3 g, 5.86 mmol), compound 1b.2 (81.8 g, 322.0 mmol), potassium acetate (57.5 g, 585.6 mmol), 1,4-dioxane (300 mL) and DMF (200 mL) was stirred under argon atmosphere at 95° C. overnight. The reaction solution was filtered, concentrated and purified by combiflash (EA:MeOH=90:10) to give a solid compound 1b (33 g, 75%). MS m/z (ESI): 304.3 [M+H]$^+$.

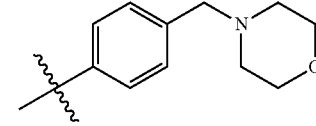

or boric acid or boronate intermediates

The intermediate compounds are represented by formula (A) and (B), and the substituent R is shown in the following table.

General step: Compounds 2b to 11b were prepared by a similar method to intermediate 1b using the bromides as raw materials.

| Intermediates No | R | MS [M + H]$^+$ |
|---|---|---|
| 2b | 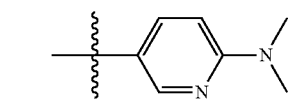 [SMILES: *c1ccc(N(C)C)nc1] | 304 |
| 3b | 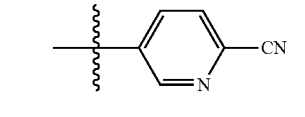 [SMILES: *c1ccc(C#N)nc1] | 249.3 |
| 4b | 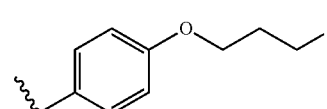 | 149.1 |
| 5b | 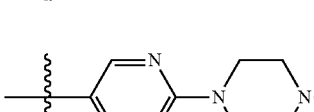 | 306 |
| 6b | 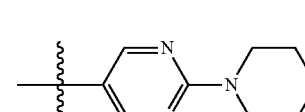 | 305 |
| 7b | 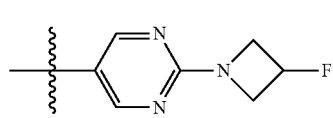 [SMILES: *c1cnc(N2CC(F)C2)nc1] | 292 |
| 8b |  | 280 |
| 9b | 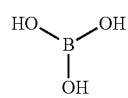 | 372 |

-continued

| Intermediates No | R | MS [M + H]+ |
|---|---|---|
| 10b |  | 304 |
| 11b | 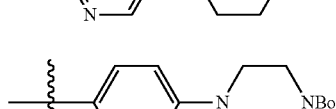 | 390 |

Preparation of Intermediate 12b

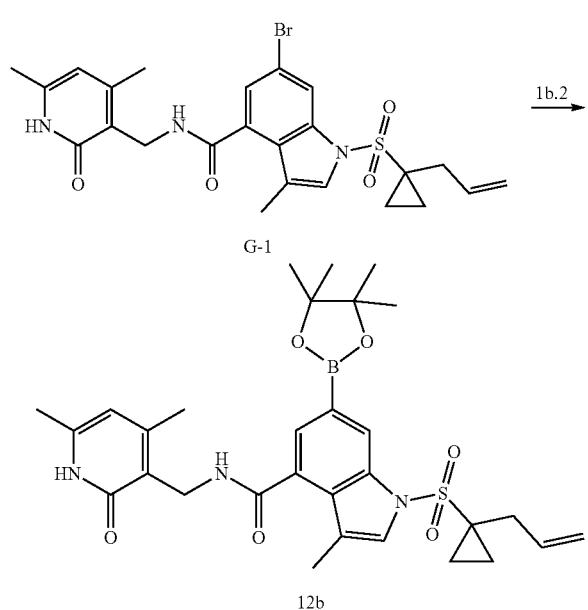

The preparation method is the same as that of compound 1b, except that compound 1b-2 in the preparation method of 1b is replaced with compound G-1. MS m/z (ESI): 580[M−H]+.

EXAMPLE 1

Preparation of 6-bromo-1-(1-cyclopropyl-3-butenyl-sulfonyl)-N-((4, 6-dimethyl-2-oxo-1,2-dihydropyridin-3-yl)methyl)-3-methyl-1H-indole-4-carboxamide (Compound G-1)

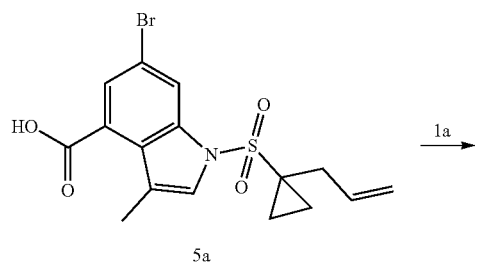

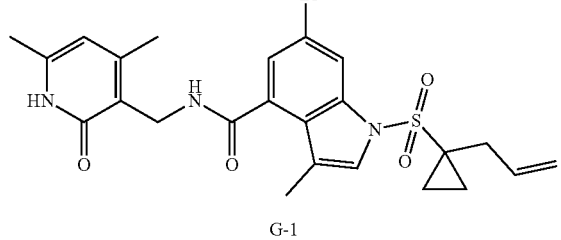

To a solution of compound 5a (370 mg, 0.932 mmol) in dichloromethane (30 mL) was added to compound 1a (500 mg, 2.65 mmol), EDCI (450 mg, 2.347 mmol), HOBt (450 mg, 3.33 mmol) and triethylamine (600 mg, 5.929 mmol). The mixture was stirred under argon at room temperature overnight. LC-MS was followed until the reaction was completed. The reaction solution was concentrated and purified by combiflash (PE:EA=100:0-0:100) to obtain compound G-1 (260 mg, 52.5%). MS m/z (ESI): 532.1[M+H]+.

EXAMPLE 2

Preparation of 1-(1-cyclopropyl-3-butenylsulfonyl)-N-((4, 6-dimethyl-2-oxo-1, 2-dihydropyridin-3-yl)methyl)-3-methyl-6-(6-(4-methylpiperazin-1-yl)pyridin-3-yl)-1H-indole-4-carboxamide (Compound G-2)

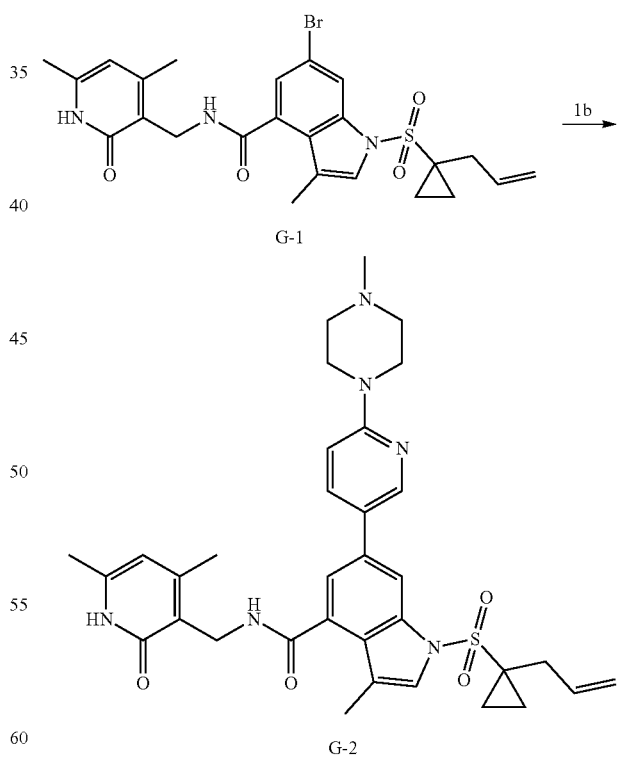

A mixture of compound G-1 (250 mg, 0.471 mmol), compound 1b (400 mg, 1.316 mmol), Pd(dppf)Cl$_2$ (100 mg, 0.136 mmol), cesium fluoride (400 mg, 2.631 mmol), acetonitrile (12 mL) and 0.1 mL of water was microwaved at 100° C. under an argon atmosphere for 15 minutes.

LC-MS was followed until the reaction was completed. The reaction solution was poured into water, extracted with dichloromethane, concentrated and purified by Prep-HPLC to give compound G-2 as a white solid (22.7 mg, 7.7%).

MS m/z (ESI): 629.4[M+H]$^+$; $^1$H NMR (400 MHz, DMSO-d$_6$): δ 11.48 (br. s., 1H), 8.47-8.44 (m, 1H), 8.42 (d, 1H), 8.00 (d, 1H), 7.84 (dd, 1H), 7.47 (s, 1H), 7.41 (s, 1H), 6.95 (d, 1H), 5.87 (s, 1H), 5.59-5.48 (m, 1H), 4.97-4.90 (m, 2H), 4.34 (d, 2H), 3.56-3.53 (m, 4H), 2.43-2.39 (m, 4H), 2.30 (d, 2H), 2.23 (d, 6H), 2.16 (s, 3H), 2.11 (s, 3H), 1.57-1.53 (m, 2H), 1.11-1.06 (m, 2H).

EXAMPLE 3-44, 63-65, 70-73

General step: compounds G-3 to G-44 were prepared by a similar method to Example 2 using compound G-1 or 6a and their boric acids or boronates as raw materials; G-70 to G-73 were prepared by a similar method to Example 69. The structures of examples 3-44, 63, 65, 70-73 are the structures of the compound of formula (I) in which Z is =CH—, and R$_1$, R$_2$, S(O)$_2$R$_3$ are the structures shown in the table below; the structure of example 64 is the structure of the compound of formula (I) in which Z is =N—, and R$_1$, R$_2$. S(O)$_2$R$_3$ are the structures shown in the table below.

| Example No. | compound | R$_1$ | R$_2$ | S(O)$_2$R$_3$ | MS[M + H]$^+$ |
|---|---|---|---|---|---|
| 3 | G-3 | Me | 4-(morpholinomethyl)phenyl | 1-allylcyclopropylsulfonyl | 629.3 |
| 4 | G-4 | Me | 3-((dimethylamino)methyl)phenyl | 1-allylcyclopropylsulfonyl | 587 |
| 5 | G-5 | Me | 4-(2-(dimethylamino)ethoxy)phenyl | 1-allylcyclopropylsulfonyl | 617.4 |
| 6 | G-6 | Me | 4-((dimethylamino)methyl)phenyl | 1-allylcyclopropylsulfonyl | 587 |
| 7 | G-7 | Me | pyridin-3-yl | 1-allylcyclopropylsulfonyl | 531.3 |
| 8 | G-8 | Me | 6-(dimethylamino)pyridin-3-yl | 1-allylcyclopropylsulfonyl | 574.3 |
| 9 | G-9 | Me | 6-aminopyridin-3-yl | 1-allylcyclopropylsulfonyl | 546.3 |

-continued

| Example No. | compound | R₁ | R₂ | S(O)₂R₃ | MS[M + H]⁺ |
|---|---|---|---|---|---|
| 10 | G-10 | Me | 5-(2-cyanopyridyl) | 1-allylcyclopropyl sulfonyl | 556.3 |
| 11 | G-11 | Me | 4-(3-dimethylaminopropoxy)phenyl | 1-allylcyclopropyl sulfonyl | 631 |
| 12 | G-12 | Me | 5-(2-morpholinopyridyl) | 1-allylcyclopropyl sulfonyl | 616.3 |
| 13 | G-13 | Me | 5-(2-(4-methylpiperazin-1-yl)pyrimidinyl) | 1-allylcyclopropyl sulfonyl | 630.4 |
| 14 | G-14 | MeO | 5-(2-(4-methylpiperazin-1-yl)pyridyl) | 1-allylcyclopropyl sulfonyl | 645.4 |
| 15 | G-15 | Me | 3-(dimethylaminomethyl)-4-fluorophenyl | 1-allylcyclopropyl sulfonyl | 605 |
| 16 | G-16 | Me | 4-(dimethylaminomethyl)-3-fluorophenyl | 1-allylcyclopropyl sulfonyl | 605 |
| 17 | G-17 | i-PrO | 4-(dimethylaminomethyl)phenyl | 1-allylcyclopropyl sulfonyl | 631 |
| 18 | G-18 | Me | 3-fluoro-4-(dimethylaminomethyl)phenyl | 1-allylcyclopropyl sulfonyl | 605 |

-continued

| Example No. | compound | R₁ | R₂ | S(O)₂R₃ | MS[M + H]⁺ |
|---|---|---|---|---|---|
| 19 | G-19 | i-PrO | 5-(4-methylpiperazin-1-yl)pyridin-2-yl | 1-allylcyclopropylsulfonyl | 673 |
| 20 | G-20 | MeO | 2-(4-methylpiperazin-1-yl)pyrimidin-5-yl | 1-allylcyclopropylsulfonyl | 646.9 |
| 21 | G-21 | Me | 3-((dimethylamino)methyl)-4-fluorophenyl | 1-allylcyclopropylsulfonyl | 605 |
| 22 | G-22 | MeO | 2-morpholinopyrimidin-5-yl | 1-allylcyclopropylsulfonyl | 633 |
| 23 | G-23 | MeO | 2-(piperazin-1-yl)pyrimidin-5-yl | 1-allylcyclopropylsulfonyl | 632 |
| 24 | G-24 | Me | 2-(3-fluoroazetidin-1-yl)pyrimidin-5-yl | 1-allylcyclopropylsulfonyl | 605 |
| 25 | G-25 | MeO | 1H-pyrazol-4-yl | 1-allylcyclopropylsulfonyl | 536 |
| 26 | G-26 | MeO | pyrimidin-5-yl | 1-allylcyclopropylsulfonyl | 548 |
| 27 | G-27 | MeO | pyridin-3-yl | 1-allylcyclopropylsulfonyl | 547 |
| 28 | G-28 | MeO | 4-(4-methylpiperazin-1-yl)phenyl | 1-allylcyclopropylsulfonyl | 642.3 |

-continued
| Example No. | compound | R₁ | R₂ | S(O)₂R₃ | MS[M + H]⁺ |
|---|---|---|---|---|---|
| 29 | G-29 | MeO | 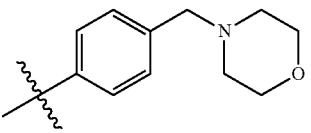 [SMILES: *c1ccc(CN2CCOCC2)cc1] | 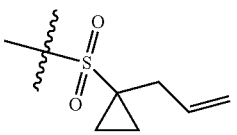 [SMILES: *S(=O)(=O)C1(CC=C)CC1] | 645.4 |
| 30 | G-30 | MeO | 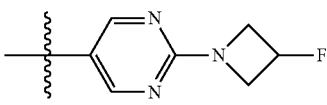 [SMILES: *c1cnc(N2CC(F)C2)nc1] | 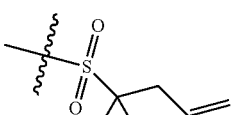 | 619.3 |
| 31 | G-31 | MeO | 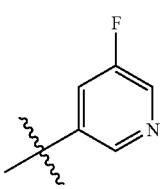 [SMILES: *c1cncc(F)c1] | 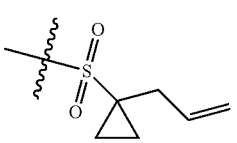 [SMILES: *S(=O)(=O)C1(CC=C)CC1] | 565.2 |
| 32 | G-32 | MeO | 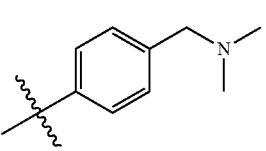 [SMILES: *c1ccc(CN(C)C)cc1] | 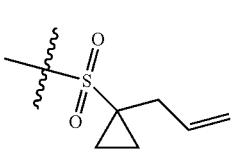 [SMILES: *S(=O)(=O)C1(CC=C)CC1] | 603.3 |
| 33 | G-33 | MeO | 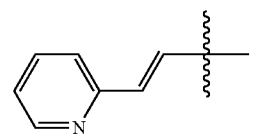 [SMILES: */C=C/c1ccccn1] | 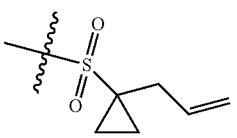 [SMILES: *S(=O)(=O)C1(CC=C)CC1] | 573 |
| 34 | G-34 | Cl | 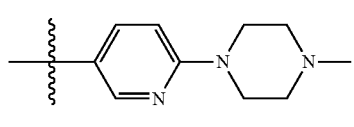 | 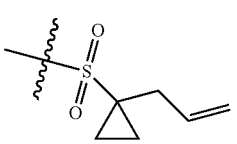 [SMILES: *S(=O)(=O)C1(CC=C)CC1] | 649 |
| 35 | G-35 | Pr | 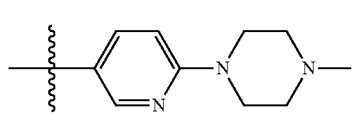 [SMILES: *c1ccc(N2CCN(C)CC2)nc1] | 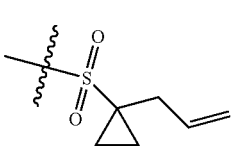 [SMILES: *S(=O)(=O)C1(CC=C)CC1] | 657.5 |
| 36 | G-36 | MeO | 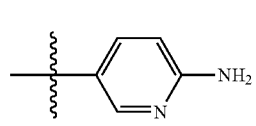 | 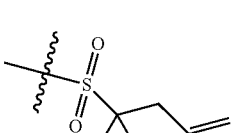 | 562.2 |
| 37 | G-37 | MeO | 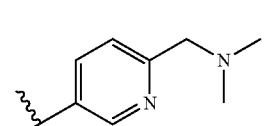 | 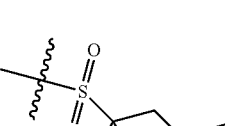 | 604.3 |

-continued

| Example No. | compound | R₁ | R₂ | S(O)₂R₃ | MS[M + H]⁺ |
|---|---|---|---|---|---|
| 38 | G-38 | MeO | 5-(dimethylamino)pyridin-2-yl | 1-allylcyclopropylsulfonyl | 589.9 |
| 39 | G-39 | MeO | 5-(4-methylpiperazin-1-yl)pyridin-3-yl | 1-allylcyclopropylsulfonyl | 645 |
| 40 | G-40 | Me | 2-(4-isopropylpiperazin-1-yl)pyrimidin-5-yl | 1-allylcyclopropylsulfonyl | 658 |
| 41 | G-41 | Me | 6-(4-(2,2,2-trifluoroethyl)piperazin-1-yl)pyridin-3-yl | 1-allylcyclopropylsulfonyl | 697 |
| 42 | G-42 | MeO | 6-(4-(2,2,2-trifluoroethyl)piperazin-1-yl)pyridin-3-yl | 1-allylcyclopropylsulfonyl | 713 |
| 43 | G-43 | MeO | 2-(4-methylpiperazin-1-yl)pyridin-4-yl | 1-allylcyclopropylsulfonyl | 645 |
| 44 | G-44 | MeO | 6-(morpholinomethyl)pyridin-3-yl | 1-allylcyclopropylsulfonyl | 646 |
| 63 | G-63 | MeO | 6-(piperazin-1-yl)pyridin-3-yl | 1-allylcyclopropylsulfonyl | 631 |
| 64 | G-64 | MeO | 2-(4-methylpiperazin-1-yl)pyrimidin-5-yl | isopropylsulfonyl | 607 |

-continued

| Example No. | compound | R₁ | R₂ | S(O)₂R₃ | MS[M + H]⁺ |
|---|---|---|---|---|---|
| 65 | G-65 | Me | 5-(piperazin-1-yl)pyrimidin-2-yl (NH) | 1-allylcyclopropylsulfonyl | 616 |
| 70 | G-70 | MeO | 4-(2,2,2-trifluoroethyl)piperazin-1-yl | 1-allylcyclopropylsulfonyl | 636 |
| 71 | G-71 | MeO | 4-(dimethylamino)piperidin-1-yl | 1-allylcyclopropylsulfonyl | 596 |
| 72 | G-72 | MeO | 3,4-dimethylpiperazin-1-yl | 1-allylcyclopropylsulfonyl | 582 |
| 73 | G-73 | MeO | 4-ethylpiperazin-1-yl | 1-allylcyclopropylsulfonyl | 582 |

G-4  ¹H NMR (400 MHz, DMSO)δ11.47 (s, 1H), 8.49 (t, 1H), 8.17 (s, 1H), 8.09 (d, 1H), 7.59-7.55 (m, 2H), 7.51 (d, 1H), 7.47-7.44 (m, 2H), 7.31 (s, 1H), 5.87 (s, 1H), 5.59-5.51 (m, 1H), 4.96-4.91 (m, 2H), 4.35 (d, 2H), 3.51 (s, 2H), 2.31 (d, 2H), 2.24 (s, 3H), 2.20 (s, 6H), 2.17 (d, 3H), 2.11 (s, 3H), 1.56 (t, 2H), 1.09 (t, 2H).

G-6  ¹H NMR (400 MHz, DMSO)δ11.47 (s, 1H), 8.48 (t, 1H), 8.09 (s, 1H), 7.64-7.62 (m, 2H), 7.51-7.47 (m, 2H), 7.42-7.40 (m, 2H), 5.87 (s, 1H), 5.55-5.51 (m, 1H), 4.96-4.91 (m, 2H), 4.35 (d, 2H), 3.43 (s, 2H), 2.32 (d, 2H), 2.24 (s, 3H), 2.17 (s, 9H), 2.11 (s, 3H), 1.55 (t, 2H), 1.09 (t, 2H).

G-7  ¹H NMR (400 MHz, DMSO-d₆): δ 11.45 (s, 1H), 8.86 (d, 1H), 8.57 (dd, 1H), 8.47-8.45 (m, 1H), 8.08 (d, 1H), 8.07-8.04 (m, 1H), 7.54-7.47 (m, 3H), 5.84 (s, 1H), 5.56-5.45 (m, 1H), 4.93-4.86 (m, 2H), 4.32 (d, 2H), 2.29 (d, 2H), 2.22 (s, 3H), 2.15 (s, 3H), 2.08 (s, 3H), 1.56-1.51 (m, 2H), 1.09-1.05 (m, 2H).

G-8  ¹H NMR (400 MHz, DMSO-d₆): δ 11.47 (s, 1H), 8.46-8.43 (m, 1H), 8.40 (d, 1H), 7.99 (s, 1H), 7.82 (dd, 1H), 7.43 (d, 2H), 6.76 (d, 1H), 5.87 (s, 1H), 5.60-5.49 (m, 1H), 4.97-4.91 (m, 2H), 4.34 (d, 2H), 3.08 (s, 6H), 2.30 (d, 2H), 2.24 (s, 3H), 2.16 (s, 3H), 2.11 (s, 3H), 1.52-1.58 (m, 2H), 1.12-1.06 (m, 2H).

G-9  ¹H NMR (400 MHz, DMSO-d₆): δ 11.48 (s, 1H), 8.45-8.42 (m, 1H), 8.23 (d, 1H), 7.96 (s, 1H), 7.69 (dd, 1H), 7.45 (s, 1H), 7.38 (s, 1H), 6.56 (d, 1H), 6.13 (s, 2H), 5.87 (s, 1H), 5.58-5.50 (m, 1H), 4.97-4.90 (m, 2H), 4.34 (d, 2H), 2.30 (d, 2H), 2.24 (s, 3H), 2.15 (s, 3H), 2.11 (s, 3H), 1.57-1.50 (m, 2H), 1.11-1.05 (m, 2H).

G-10  ¹H NMR (400 MHz, DMSO-d₆): δ 11.49 (s, 1H), 9.10 (d, 1H), 8.51-8.48 (m, 1H), 8.36 (dd, 1H), 8.18 (d, 1H), 8.15 (d, 1H), 7.62 (dd, 2H), 5.87 (s, 1H), 5.57-5.45 (m, 1H), 4.93 (s, 1H), 4.90 (d, 1H), 4.36 (d, 2H), 2.32 (d, 2H), 2.25 (s, 3H), 2.18 (s, 3H), 2.11 (s, 3H), 1.60-1.57 (m, 2H), 1.12-1.08 (m, 2H).

G-11  ¹H NMR (400 MHz, DMSO)δ11.47 (s, 1H), 8.46 (t, 1H), 8.03 (s, 1H), 7.60-7.58 (m, 2H), 7.48-7.45 (m, 2H), 7.06-7.04 (m, 2H), 5.87 (s, 1H), 5.59-5.48 (m, 1H), 4.96-4.91 (m, 2H), 4.35 (d, 2H), 4.04 (t, 2H), 2.41-2.38 (m, 2H), 2.31 (d, 2H), 2.24-2.11 (m, 13H), 1.87-1.86 (m, 2H), 1.56 (t, 2H), 1.23 (s, 2H), 1.08 (t, 2H).

G-12  ¹H NMR (400 MHz, DMSO-d₆): δ 11.48 (s, 1H), 8.47-8.43 (m, 2H), 8.01 (d, 1H), 7.88 (dd, 1H), 7.47 (d, 1H), 7.43 (d, 1H), 6.96 (d, 1H), 5.87 (s, 1H), 5.60-5.49 (m, 1H), 4.97-4.90 (m, 2H), 4.34 (d, 2H), 3.74-3.70 (m, 4H), 3.52-3.49 (m, 4H), 2.31 (d, 2H), 2.24 (s, 3H), 2.16 (s, 3H), 2.11 (s, 3H), 1.57-1.48 (m, 2H), 1.12-1.07 (m, 2H).

G-13  ¹H NMR (400 MHz, DMSO-d₆): δ 11.45 (br. s., 1H), 8.66 (s, 2H), 8.40 (t, 1H), 7.97 (d, 1H), 7.46 (d, 1H), 7.41 (d, 1H), 5.85 (s, 1H), 5.56-5.45 (m, 1H), 4.93 (d, 1H), 4.89 (dd, 1H), 4.32 (d, 2H), 3.79-3.75 (m, 4H), 2.38-2.34 (m, 4H), 2.28 (d, 2H), 2.22 (s, 3H), 2.20 (s, 3H), 2.13 (s, 3H), 2.09 (s, 3H), 1.57-1.53 (m, 2H), 1.07-1.03 (m, 2H).

| | |
|---|---|
| G-14 | ¹H NMR (400 MHz, DMSO-d₆): δ 11.43 (s, 1H), 8.42 (d, 1H), 8.23 (t, 1H), 7.99 (d, 1H), 7.84 (dd, 1H), 7.46 (d, 1H), 7.40 (d, 1H), 6.95 (d, 1H), 6.09 (s, 1H), 5.61-5.49 (m, 1H), 4.96 (d, 1H), 4.93 (d, 1H), 4.29 (d, 2H), 3.81 (s, 3H), 3.58-3.53 (m, 4H), 2.47-2.40 (m, 4H), 2.31 (d, 2H), 2.24 (s, 3H), 2.21 (s, 3H), 2.17 (s, 3H), 1.57-1.53 (m, 2H), 1.10-1.06 (m, 2H). |
| G-15 | ¹H NMR (400 MHz, DMSO)δ11.46 (s, 1H), 8.49 (t, 1H), 8.27 (s, 1H), 8.06 (s, 1H), 7.54 (s, 1H), 7.49 (d, 1H), 7.33-7.27 (m, 2H), 5.86 (s, 1H), 5.57-5.48 (m, 1H), 4.95-4.91 (m, 2H), 4.34 (d, 2H), 3.44 (s, 2H), 2.32 (d, 2H), 2.24 (s, 3H), 2.17 (s, 9H), 2.11 (s, 3H), 1.56 (t, 2H), 1.08 (t, 2H). |
| G-16 | ¹H NMR (400 MHz, DMSO)δ11.49 (s, 1H), 8.49 (t, 1H), 8.09 (s, 1H), 7.53-7.48 (m, 5H), 5.87 (s, 1H), 5.56-5.51 (m, 1H), 4.95-4.91 (m, 2H), 4.35 (d, 2H), 3.48 (s, 2H), 2.32 (d, 2H), 2.25 (s, 3H), 2.19-2.17 (m, 8H), 2.12-2.11 (m, 4H), 1.56 (t, 2H), 1.09 (t, 2H). |
| G-17 | ¹H NMR (400 MHz, DMSO)δ11.34 (s, 1H), 8.23 (t, 1H), 8.18 (s, 1H), 8.08 (s, 1H), 7.62 (d, 2H), 7.51 (s, 1H), 7.46 (s, 1H), 7.41 (d, 2H), 6.08 (s, 1H), 5.57-5.49 (m, 1H), 4.95-4.91 (m, 2H), 4.68-4.64 (m, 1H), 4.28 (d, 2H), 3.47 (s, 2H), 2.32 (d, 2H), 2.23 (s, 3H), 2.19 (s, 6H), 2.15 (s, 3H), 1.55 (t, 2H), 1.27 (d, 6H), 1.09 (t, 2H). |
| G-18 | ¹H NMR (400 MHz, DMSO)δ11.46 (s, 1H), 8.47 (t, 1H), 8.07 (s, 1H), 7.57-7.54 (m, 2H), 7.35 (s, 1H), 7.26-7.24 (m, 2H), 5.86 (s, 1H), 5.53-5.48 (m, 1H), 4.95-4.91 (m, 2H), 4.34 (s, 2H), 3.44 (s, 2H), 2.31 (d, 2H), 2.24 (s, 3H), 2.17 (s, 9H), 2.11 (s, 3H), 1.56 (t, 2H), 1.08 (t, 2H). |
| G-19 | ¹H NMR (500 MHz, DMSO-d₆): δ 11.29 (br. s., 1H), 8.34 (d, 1H), 8.13 (t, 1H), 7.93 (d, 1H), 7.76 (dd, 1H), 7.40 (dd, 1H), 7.34 (d, 1H), 6.88 (d, 1H), 6.01 (s, 1H), 5.52-5.43 (m, 1H), 4.90-4.84 (m, 2H), 4.62-4.56 (m, 1H), 4.21 (d, 2H), 3.49-3.47 (m, 4H), 2.38-2.35 (m, 4H), 2.24 (d, 2H), 2.16 (d, 6H), 2.09 (d, 3H), 1.48-1.46 (m, 2H), 1.20 (d, 6H), 1.04-0.98 (m, 2H). |
| G-20 | ¹H NMR (400 MHz, DMSO)δ11.42 (s, 1H), 8.69 (s, 2H), 8.21 (t, 1H), 7.99 (d, 1H), 7.49 (d, 1H), 7.43 (d, 1H), 6.09 (s, 1H), 5.59-5.49 (m, 1H), 4.96-4.91 (m, 2H), 4.30 (d, 2H), 3.80 (s, 7H), 2.47 (s, 3H), 2.32 (d, 5H), 2.19 (d, 7H), 1.56 (t, 2H), 1.07 (t, 2H). |
| G-21 | ¹H NMR (400 MHz, DMSO)δ11.48 (s, 1H), 8.50 (t, 1H), 8.06 (d, 1H), 7.68-7.65 (m, 1H), 7.62-7.58 (m, 1H), 7.51 (d, 1H), 7.43 (d, 1H), 7.30 (t, 1H), 5.87 (s, 1H), 5.61-5.53 (m, 1H), 4.96-4.91 (m, 2H), 4.34 (d, 2H), 3.53 (s, 2H), 2.31 (d, 3H), 2.24-2.17 (m, 11H), 2.11 (s, 3H), 1.53 (t, 2H), 1.10 (t, 2H). |
| G-22 | 1H NMR (400 MHz, DMSO)δ11.43 (s, 1H), 8.70 (s, 2H), 8.21 (s, 1H), 8.00 (s, 1H), 7.47 (d, 2H), 6.09 (s, 1H), 5.59-5.49 (m, 1H), 4.96-4.91 (m, 2H), 4.29 (s, 2H), 3.81-3.69 (m, 11H), 2.31 (d, 2H), 2.19 (d, 6H), 1.57 (t, 2H), 1.08 (t, 2H). |
| G-23 | ¹H NMR (400 MHz, DMSO-d₆): δ 11.40 (br. s., 1H), 8.66 (s, 2H), 8.24-8.21 (m, 1H), 7.98 (s, 1H), 7.48 (s, 1H), 7.42 (s, 1H), 6.09 (s, 1H), 5.58-5.50 (m, 1H), 4.97-4.91 (m, 2H), 4.29 (d, 2H), 3.80 (s, 3H), 3.74-3.72 (m, 4H), 2.79-2.76 (m, 4H), 2.30 (d, 2H), 2.21 (s, 3H), 2.17 (s, 3H), 1.59-1.54 (m, 2H), 1.09-1.04 (m, 2H). |
| G-24 | ¹H NMR (400 MHz, DMSO-d₆): δ 11.44 (br. s., 1H), 8.66 (s, 2H), 8.41-8.38 (m, 1H), 7.96 (d, 1H), 7.46 (d, 1H), 7.40 (d, 1H), 5.86 (s, 1H), 5.51-5.40 (m, 2H), 4.92-4.86 (m, 2H), 4.41-4.36 (m, 2H), 4.29 (d, 2H), 4.14 (d, 1H), 4.07 (d, 1H), 2.26 (d, 2H), 2.20 (s, 3H), 2.11 (s, 3H), 2.07 (s, 3H), 1.54-1.51 (m, 2H), 1.05-1.02 (m, 2H). |
| G-25 | ¹H NMR (400 MHz, DMSO-d₆): δ 11.41 (br. s., 1H), 8.17-7.94 (m, 4H), 7.38 (d, 2H), 6.06 (s, 1H), 5.56-5.46 (m, 1H), 4.95-4.88 (m, 2H), 4.25 (d, 2H), 3.77 (s, 3H), 2.26 (d, 2H), 2.15 (d, 6H), 1.55-1.53 (m, 2H), 1.04-1.02 (m, 2H). |
| G-26 | ¹H NMR (400 MHz, DMSO)δ11.45 (s, 1H), 9.21 (s, 1H), 9.13 (s, 2H), 8.27 (t, 1H), 8.15 (s, 1H), 7.59 (s, 2H), 6.10 (s, 1H), 5.58-5.47 (m, 1H), 4.95-4.91 (m, 2H), 4.30 (d, 2H), 3.81 (s, 3H), 2.33 (d, 2H), 2.23 (s, 3H), 2.17 (s, 3H), 1.60 (t, 2H), 1.09 (t, 2H). |
| G-27 | ¹H NMR (400 MHz, DMSO)δ11.45 (s, 1H), 8.88 (s, 1H), 8.60 (d, 1H), 8.29 (t, 1H), 8.10-8.08 (m, 2H), 7.56-7.51 (m, 3H), 6.10 (s, 1H), 5.59-5.49 (m, 1H), 4.95-4.91 (m, 2H), 4.30 (d, 2H), 3.81 (s, 3H), 2.32 (d, 2H), 2.23 (s, 3H), 2.17 (s, 3H), 1.57 (t, 2H), 1.10 (t, 2H). |
| G-28 | ¹H NMR (400 MHz, DMSO)δ11.43 (s, 1H), 8.24 (t, 1H), 8.02 (d, 1H), 7.52 (d, 2H), 7.45 (d, 1H), 7.39 (d, 1H), 7.05 (d, 2H), 6.09 (s, 1H), 5.60-5.50 (m, 1H), 4.97-4.91 (m, 2H), 4.28 (d, 2H), 3.81 (s, 3H), 3.20 (t, 4H), 2.47 (t, 5H), 2.31 (d, 2H), 2.23-2.17 (m, 8H), 1.55 (t, 2H), 1.08 (t, 2H). |
| G-29 | ¹H NMR (400 MHz, DMSO-d₆): δ 11.39 (s, 1H), 8.24-8.20 (m, 1H), 8.03 (br. s., 1H), 7.58 (d, 2H), 7.46 (s, 1H), 7.41-7.37 (m, 3H), 6.05 (s, 1H), 5.56-5.45 (m, 1H), 4.93-4.87 (m, 2H), 4.25 (d, 2H), 3.77 (s, 3H), 3.56-3.53 (m, 4H), 3.47 (s, 2H), 2.36-2.34 (m, 4H), 2.28 (d, 2H), 2.18 (s, 3H), 2.13 (s, 3H), 1.54-1.48 (m, 2H), 1.07-1.02 (m, 2H). |
| G-30 | ¹H NMR (400 MHz, DMSO)δ11.43 (s, 1H), 8.69 (s, 2H), 8.22 (t, 1H), 8.00 (d, 1H), 7.49 (d, 1H), 7.43 (d, 1H), 6.09 (s, 1H), 5.61-5.45 (m, 2H), 4.96-4.91 (m, 2H), 4.48-4.39 (m, 2H), 4.29 (d, 2H), 4.19-4.11 (m, 2H), 3.81 (s, 3H), 2.30 (d, 2H), 2.21 (s, 3H), 2.17 (s, 3H), 1.57 (t, 2H), 1.08 (t, 2H). |
| G-32 | ¹H NMR (400 MHz, DMSO-d₆): δ 11.44 (s, 1H), 8.29-8.26 (m, 1H), 8.08 (d, 1H), 7.62 (d, 2H), 7.51 (s, 1H), 7.46 (s, 1H), 7.40 (d, 2H), 6.09 (s, 1H), 5.60-5.49 (m, 1H), 4.97-4.91 (m, 2H), 4.29 (d, 2H), 3.81 (s, 3H), 3.44 (s, 2H), 2.32 (d, 2H), 2.22 (s, 3H), 2.17 (s, 9H), 1.57-1.53 (m, 2H), 1.11-1.08 (m, 2H). |
| G-33 | ¹H NMR (400 MHz, DMSO-d₆): δ 11.41 (br. s., 1H), 8.55-8.53 (m, 1H), 8.23-8.21 (m, 1H), 8.01 (s, 1H), 7.79-7.74 (m, 2H), 7.60 (d, 1H), 7.49 (d, 1H), 7.30 (d, 1H), 7.25-7.21 (m, 1H), 6.07 (s, 1H), 5.54-5.47 (m, 1H), 4.95-4.89 (m, 2H), 4.26 (d, 2H), 3.78 (s, 3H), 2.28 (d, 2H), 2.15 (d, 6H), 1.57-1.56 (m, 2H), 1.05-1.03 (m, 2H). |
| G-34 | ¹H NMR (400 MHz, DMSO-d6): δ 11.87 (br. s., 1H), 8.50-8.48 (m, 1H), 8.38 (d, 1H), 7.99 (d, 1H), 7.81 (d, 1H), 7.45 (s, 1H), 7.40 (d, 1H), 6.92 (d, 1H), 6.15 (s, 1H), 5.56-5.48 (m, 1H), 4.94-4.90 (m, 2H), 4.38 (d, 2H), 3.52-3.50 (m, 4H), 2.48-2.46 (m, 4H), 2.38 (d, 2H), 2.19 (s, 3H), 2.17 (s, 3H), 2.12 (s, 3H), 1.53-1.51 (m, 2H), 1.06-1.04 (m, 2H). |

| | |
|---|---|
| G-35 | ¹H NMR (400 MHz, DMSO-d₆): δ 11.50 (br. s., 1H), 8.48-8.42 (m, 1H), 8.41 (d, 1H), 8.00 (s, 1H), 7.83 (dd, 1H), 7.48 (s, 1H), 7.41 (s, 1H), 6.96 (d, 1H), 5.90 (s, 1H), 5.56-5.53 (m, 1H), 4.96-4.90 (m, 2H), 4.35 (d, 2H), 3.57-3.52 (m, 4H), 2.53 (q, 2H), 2.45-2.42 (m, 4H), 2.30 (d, 2H), 2.24 (s, 3H), 2.17 (s, 3H), 2.12 (s, 3H), 1.60-1.54 (m, 4H), 1.10-1.07 (m, 2H), 0.93 (t, 3H). |
| G-36 | ¹H NMR (400 MHz, DMSO-d₆): δ 11.43 (br. s., 1H), 8.22 (s, 2H), 7.96 (d, 1H), 7.69 (dd, 1H), 7.44 (d, 1H), 7.35 (d, 1H), 6.55 (d, 1H), 6.13-6.09 (m, 3H), 5.57-5.52 (m, 1H), 4.98-4.92 (m, 2H), 4.29 (d, 2H), 3.81 (s, 3H), 2.31 (d, 2H), 2.19 (s, 3H), 2.17 (s, 3H), 1.56-1.54 (m, 2H), 1.11-1.06 (m, 2H). |
| G-37 | ¹H NMR (400 MHz, DMSO-d₆): δ 11.44(s, 1H), 8.77(d, 1H), 8.27(t, 1H), 8.10(d, 1H), 8.05-8.07(dd, 1H), 7.52-7.55(m, 2H), 7.50(d, 1H), 6.09(s, 1H), 5.49-5.60(m, 1H), 4.91-4.96(m, 2H), 4.30(d, 2H), 3.81(s, 3H), 3.58(s, 2H), 2.32(d, 2H), 2.22(s, 9H), 2.17(s, 3H), 1.57(m, 2H), 1.10(m, 2H). |
| G-38 | ¹H NMR (400 MHz, DMSO-d₆): δ 11.44 (br. s., 1H), 8.39 (d, 1H), 8.25-8.22 (m, 1H), 7.99 (d, 1H), 7.82 (dd, 1H), 7.45 (d, 1H), 7.39 (d, 1H), 6.76 (d, 1H), 6.09 (s, 1H), 5.60-5.52 (m, 1H), 4.98-4.92 (m, 2H), 4.29 (d, 2H), 3.81 (s, 3H), 3.09 (d, 6H), 2.31 (d, 2H), 2.21 (s, 3H), 2.18 (s, 3H), 1.56-1.53 (m, 2H), 1.10-1.07 (m, 2H). |
| G-39 | ¹H NMR (400 MHz, DMSO)δ11.43 (s, 1H), 8.33 (d, 1H), 8.25 (t, 2H), 8.07 (d, 1H), 7.53 (d, 1H), 7.49 (d, 2H), 6.09 (s, 1H), 5.60-5.51 (m, 1H), 4.96-4.91 (m, 2H), 4.30 (d, 2H), 3.80 (s, 3H), 3.28 (s, 4H), 2.58 (s, 4H), 2.31 (d, 5H), 2.22 (d, 3H), 2.17 (s, 3H), 1.56 (t, 2H), 1.09 (t, 2H). |
| G-40 | ¹H NMR (400 MHz, DMSO)δ11.49 (s, 1H), 8.78 (s, 2H), 8.44 (t, 1H), 8.02 (d, 1H), 7.51 (d, 1H), 7.47 (d, 1H), 5.88 (s, 1H), 5.56-5.48 (m, 1H), 4.95-4.91 (m, 2H), 4.84 (d, 2H), 4.35 (d, 2H), 3.54 (d, 3H), 3.31 (t, 2H), 3.12 (t, 2H), 2.31 (d, 2H), 2.25 (s, 3H), 2.15 (d, 3H), 2.11 (s, 3H), 1.57 (t, 2H), 1.29 (d, 6H), 1.08 (t, 2H). |
| G-41 | ¹H NMR (400 MHz, DMSO)δ11.48 (s, 1H), 8.45 (t, 1H), 8.41 (d, 1H), 8.01 (d, 1H), 7.88 (q, 1H), 7.48 (d, 1H), 7.42 (d, 1H), 6.99 (d, 1H), 5.87 (s, 1H), 5.57-5.51 (m, 1H), 4.95-4.91 (m, 2H), 4.34 (d, 2H), 3.57 (t, 4H), 3.25 (t, 2H), 2.73 (t, 4H), 2.30 (d, 2H), 2.24 (s, 3H), 2.15 (d, 3H), 2.11 (s, 3H), 1.56 (t, 2H), 1.08 (t, 2H). |
| G-42 | ¹H NMR (400 MHz, DMSO)δ11.44 (s, 1H), 8.42 (d, 1H), 8.24 (t, 1H), 8.00 (s, 1H), 7.85 (q, 1H), 7.47 (s, 1H), 7.40 (s, 1H), 6.96 (d, 1H), 6.09 (s, 1H), 5.58-5.49 (m, 1H), 4.97-4.91 (m, 2H), 4.29 (d, 2H), 3.81 (s, 3H), 3.56 (t, 4H), 3.24 (q, 2H), 2.73 (t, 4H), 2.31 (d, 2H), 2.20 (s, 3H), 2.17 (s, 3H), 1.55 (t, 2H), 1.08 (t, 2H). |
| G-43 | ¹H NMR (400 MHz, DMSO)δ11.45 (s, 1H), 8.25 (d, 2H), 8.14 (s, 1H), 7.60 (s, 1H), 7.57 (s, 1H), 7.21 (s, 1H), 7.04 (d, 1H), 6.10 (s, 1H), 5.59-5.48 (m, 1H), 4.95-4.90 (m, 2H), 4.56 (d, 2H), 4.31 (d, 2H), 3.81 (s, 3H), 3.53 (d, 2H), 3.23-3.12 (m, 4H), 2.86 (s, 3H), 2.30 (d, 2H), 2.22 (s, 3H), 2.18 (s, 3H), 1.56 (t, 2H), 1.10 (t, 2H). |
| G-44 | ¹H NMR (400 MHz, DMSO)δ11.42 (s, 1H), 8.79 (t, 1H), 8.26 (t, 1H), 8.09 (d, 1H), 8.06 (q, 1H), 7.57-7.54 (m, 2H), 7.49 (d, 1H), 6.09 (s, 1H), 5.59-5.49 (m, 1H), 4.96-4.91 (m, 2H), 4.30 (d, 2H), 3.81 (s, 3H), 3.64 (t, 2H), 3.60 (t, 4H), 2.45 (t, 4H), 2.32 (d, 2H), 2.23 (s, 3H), 2.17 (s, 3H), 1.57 (t, 2H), 1.09 (t, 2H). |
| G-63 | 1H NMR (400 MHz, DMSO-d6): δ 11.45 (br. s., 1H), 8.42 (d, 1H), 8.27-8.24 (m, 1H), 7.80 (s, 1H), 7.85 (dd, 1H), 7.47 (s, 1H), 7.40 (s, 1H), 6.94 (d, 1H), 6.10 (s, 1H), 5.60-5.51 (m, 1H), 4.97-4.91 (m, 2H), 4.28 (d, 2H), 3.80 (s, 3H), 3.55 (m., 5H), 2.90 (m, 4H), 2.30 (d, 2H), 2.18 (d, 6H), 1.60-1.53 (m, 2H), 1.10-1.06 (m, 2H). |
| G-64 | 1H NMR (400 MHz, DMSO)δ11.46 (s, 1H), 8.52 (d, 1H), 8.42 (t, 1H), 8.05 (s, 1H), 7.94 (q, 1H), 7.59 (s, 1H), 6.97 (d, 1H), 6.10 (s, 1H), 4.32 (d, 2H), 3.87-3.83 (m, 1H), 3.81 (s, 3H), 3.58 (t, 4H), 2.51 (t, 3H), 2.47 (t, 4H), 2.26 (s, 3H), 2.18 (s, 3H), 1.18 (d, 6H). |
| G-65 | 1H NMR (400 MHz, DMSO-d6): δ 11.50 (br. s., 1H), 8.67 (s, 2H), 8.43 (t, 1H), 8.00 (d, 1H), 7.48 (d, 1H), 7.43 (d, 1H), 5.87 (s, 1H), 5.57-5.49 (m, 1H), 4.95 (d, 1H), 4.92 (dd, 1H), 4.34 (d, 2H), 3.75-3.72 (m, 4H), 3.45-3.38 (m, 1H), 2.79-2.76 (m, 4H), 2.31 (d, 2H), 2.25 (s, 3H), 2.16 (s, 3H), 2.11 (s, 3H), 1.59-1.55 (m, 2H), 1.10-1.05 (m, 2H). |
| G-70 | 1H NMR (400 MHz, DMSO)δ11.26 (s, 1H), 8.10 (t, 1H), 7.33 (d, 1H), 7.23 (d, 1H), 6.89 (d, 1H), 6.08 (s, 1H), 5.58-5.50 (m, 1H), 4.98-4.93 (m, 2H), 4.25 (d, 2H), 3.80 (s, 3H), 3.23 (q, 2H), 3.15 (t, 4H), 2.78 (t, 4H), 2.27 (d, 2H), 2.17 (s, 3H), 2.13 (s, 3H), 1.49 (t, 2H), 1.03 (t, 2H). |
| G-71 | 1H NMR (400 MHz, DMSO)δ11.41 (s, 1H), 8.09 (t, 1H), 7.35 (d, 1H), 7.21 (d, 1H), 6.87 (d, 1H), 6.09 (s, 1H), 5.60-5.50 (m, 1H), 4.98-4.93 (m, 2H), 4.26 (d, 2H), 3.80 (s, 3H4H), 3.66 (d, 3H), 2.72 (t, 1H), 2.28 (d, 2H3H), 2.21-2.17 (m, 9H), 2.12 (s, 2H), 1.86 (d, 2H), 1.54 (d, 2H), 1.48 (t, 2H), 1.03 (t, 2H). |
| G-72 | 1H NMR (400 MHz, DMSO)δ11.43 (s, 1H), 8.09 (t, 1H), 7.32 (d, 1H), 7.21 (d, 1H), 6.87 (d, 1H), 6.09 (s, 1H), 5.60-5.51 (m, 1H), 4.98-4.93 (m, 2H), 4.25 (d, 2H), 3.80 (s, 3H), 3.47 (d, 4H), 2.85-2.74 (m, 2H), 2.41 (t, 1H), 2.26 (d, 2H), 2.21 (s, 3H), 2.17 (s, 3H), 2.12 (d, 3H), 1.48 (t, 2H), 1.06-1.01 (m, 5H). |
| G-73 | 1H NMR (400 MHz, DMSO)δ11.42 (s, 1H), 8.10 (t, 1H), 7.34 (d, 1H), 7.22 (d, 1H), 6.88 (d, 1H), 6.09 (s, 1H), 5.59-5.52 (m, 1H), 4.98-4.92 (m, 2H), 4.25 (d, 2H), 3.80 (s, 3H), 3.30 (s, 2H), 3.14 (s, 4H), 2.56 (s, 2H), 2.42 (s, 2H), 2.27 (d, 2H), 2.17 (s, 3H), 2.12 (d, 3H), 1.48 (t, 2H), 1.07-1.02 (m, 5H). |

EXAMPLE 45

Preparation of 6-bromo-1-(1-cyclopropyl-3-butenyl-sulfonyl)-N-((4-methoxy-6-methyl-2-oxo-1, 2-dihydropyridin-3-yl)methyl)-3-methyl-1H-indole-4-carboxamide (Compound G-45)

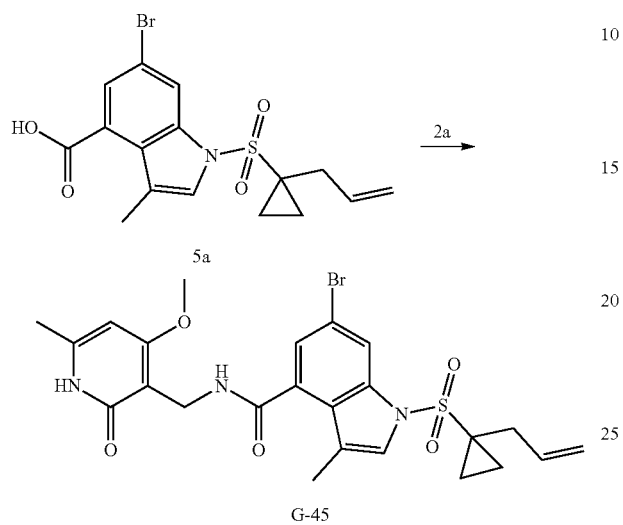

The preparation method was the same as that of compound G-1, except that compound 1a in the preparation method of G-1 was replaced with compound 2a. A solid compound G-45(20 mg, 40%) was obtained. MS m/z (ESI): 548[M+H]$^+$; $^1$H NMR (400 MHz, DMSO) δ11.46 (s, 1H), 8.30 (t, 1H), 8.01 (d, 1H), 7.52 (d, 1H), 7.30 (d, 1H), 6.10 (s, 1H), 5.57-5.46 (m, 1H), 4.96-4.92 (m, 2H), 4.25 (d, 2H), 3.80 (s, 3H), 2.29 (d, 2H), 2.17 (s, 6H), 1.54 (t, 2H), 1.10 (t, 2H).

EXAMPLE 46

Preparation of 1-(1-allylcyclopropylsulfonyl)-6-bromo-N-((4, 6-dimethyl-2-oxo-1, 2-dihydropyridin-3-yl)methyl)-1H-indole-4-carboxamide (Compound G-46)

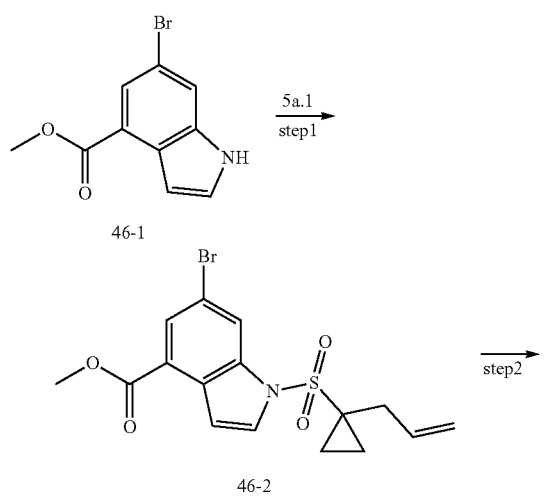

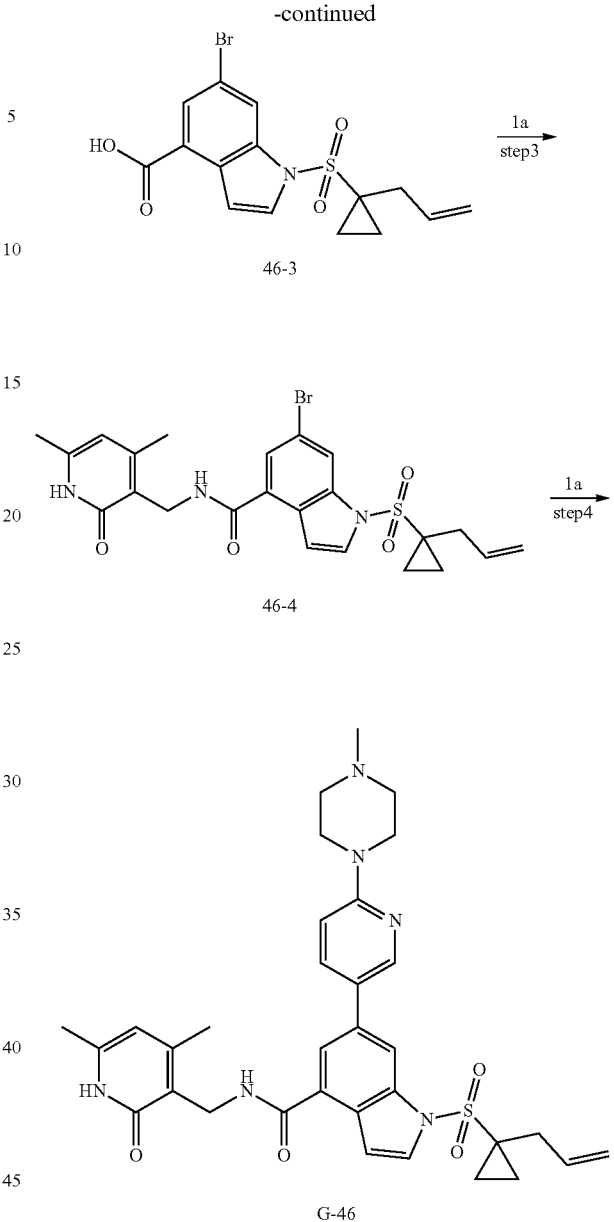

Step 1: The preparation method was the same as that of compound 5a-2, except that compound 5a-1 in the preparation method of 5a-2 was replaced with compound 46-1. MS m/z (ESI): 398[M+H]$^+$.

Step 2: The preparation method was the same as that of compound 5a, except that compound 5a-2 in the preparation method of 5a was replaced with compound 46-2. MS m/z (ESI): 384[M+H]$^+$.

Step 3: The preparation method was the same as that of compound G-1, except that compound 5a in the preparation method of G-1 was replaced with compound 46-3. MS m/z (ESI): 518[M+H]$^+$.

Step 4: The preparation method was the same as that of compound G-2, except that compound G-1 in the preparation method of G-2 was replaced with compound 46-4. After purification by Prep-HPLC, compound G-46(10 mg, 12%) was obtained as a white solid. MS m/z (ESI): 615[M+H]$^+$.

EXAMPLE 47

Preparation of N-((4, 6-dimethyl-2-oxo-1, 2-dihydropyridin-3-yl)methyl)-1-(isopropylsulfonyl)-6-(6-(4-methylpiperazin-1-yl)pyridin-3-yl)dihydroindole-4-carboxamide (compound G-47)

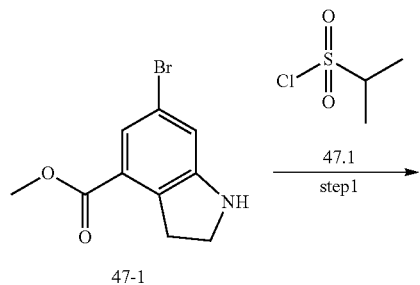

47-1

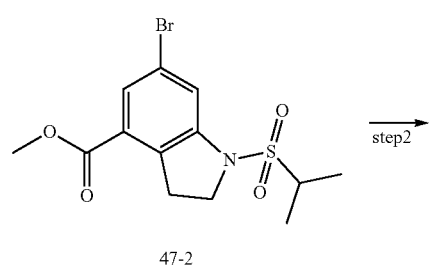

47-2

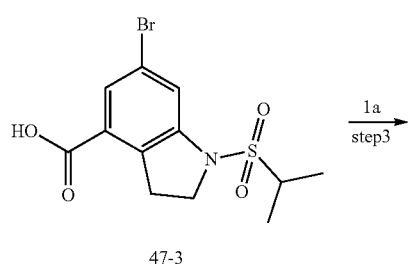

47-3

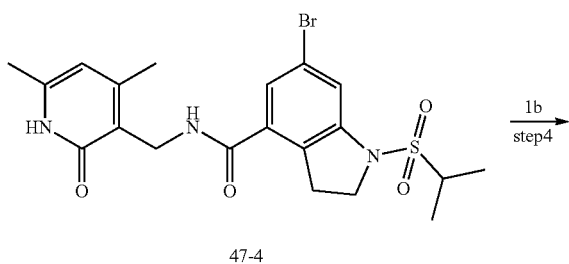

47-4

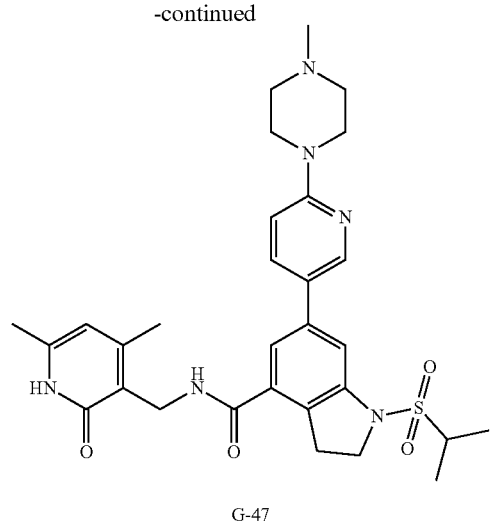

G-47

Step 1: The preparation method was the same as that of compound 5a-2, except that compounds 5a-1 and 5a.1 in the preparation method of 5a-2 were replaced with compounds 47-1 and 47.1. MS m/z (ESI): 362[M+H]+.

Step 2: The preparation method was the same as that of compound 5a, except that compound 5a-2 in the preparation method of 5a was replaced with compound 47-2. MS m/z (ESI): 348[M+H]+.

Step 3: The preparation method was the same as that of compound G-1, except that compound 5a in the preparation method of G-1 was replaced with compound 47-3. MS m/z (ESI): 482[M+H]+.

Step 4: The preparation method was the same as that of compound G-2, except that compound G-1 in the preparation method of G-2 was replaced with compound 47-4. After purification by Prep-HPLC, compound G-47(10 mg, 30%) was obtained as a white solid. MS m/z (ESI): 579 [M+H]+; $^1$H NMR (400 MHz, DMSO-$d_6$): δ 11.50 (br. s., 1H), 8.42-8.38 (m, 2H), 7.82 (d, 1H), 7.45 (d, 2H), 6.93 (d, 1H), 5.87 (s, 1H), 4.29 (d, 2H), 4.03 (t, 2H), 3.72-3.65 (m, 1H), 3.60-3.52 (m, 4H), 3.33 (t, 2H), 2.58-2.51 (m, 4H), 2.30 (s, 3H), 2.18 (s, 3H), 2.11 (s, 3H), 1.24 (d, 6H).

EXAMPLE 48

Preparation of 1-(1-allylcyclopropylsulfonyl)-N-((4, 6-dimethyl-2-oxo-1, 2-dihydropyridin-3-yl)methyl)-6-(6-(4-isopropylpiperazin-1-yl)pyridin-3-yl)-3-methyl-1H-indole-4-carboxamide (Compound G-48)

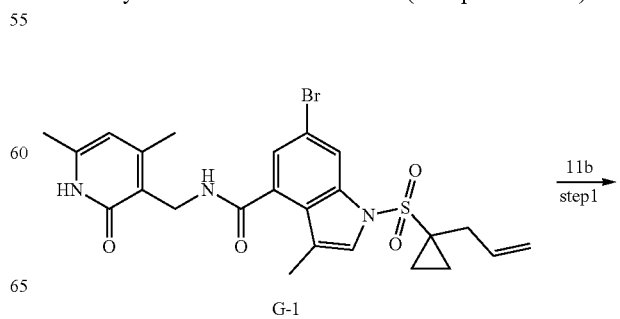

G-1

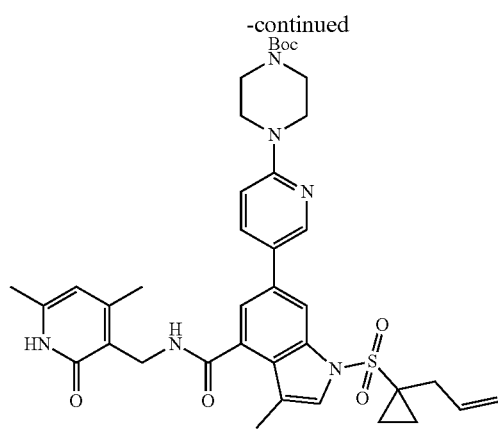

48-1

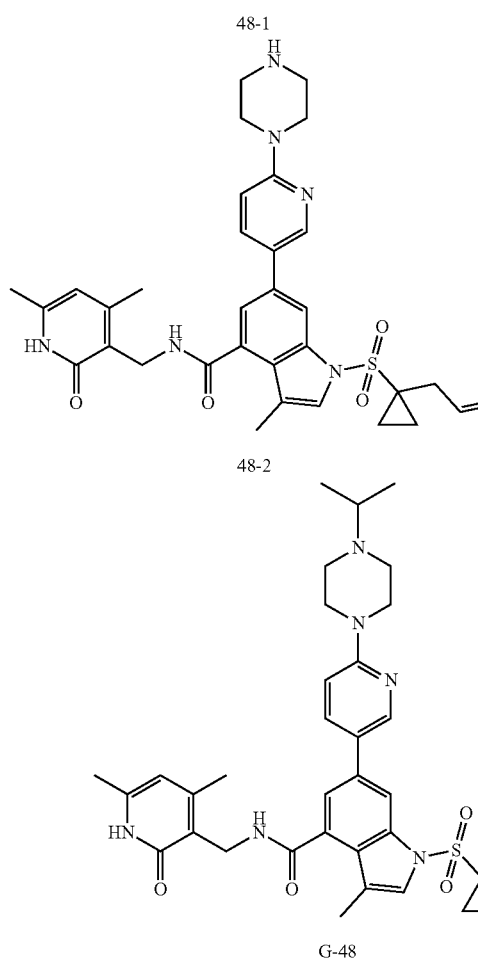

48-2

G-48

Step 1: The preparation method was the same as that of compound G-2, except that compound 1b in the preparation method of G-2 was replaced with compound 11b. MS m/z (ESI): 713.4[M+H]⁺.

Step 2: A solution of compound 48-1 (400 mg, 0.56 mmol) in 2 mL of trifluoroacetic acid and methanol (20 mL) was stirred at room temperature for 24 hours. LC-MS was followed until the reaction was completed. The reaction solution was concentrated under reduced pressure to give 400 mg of compound 48-2. MS m/z. (ESI): 613.3 [M+H]⁺.

Step 3: A solution of compound 48-2 (400 mg, 0.651 mmol), acetone (12 mL), two drops of acetic acid and methanol (20 mL) was stirred at 70° C. for 2 hours, and the mixture was cooled under an ice bath. After 1 hour, sodium cyanoborohydride (500 mg, 7.936 mmol)) was added, the system was warmed to room temperature and stirred for 12 hours. LC-MS was followed until the reaction was completed. The reaction solution was concentrated to remove the solvent, extracted with ethyl acetate/water, and the organic layer was concentrated. After purification by Prep-HPLC, compound G-48 (5.8 mg, 1.4%) was obtained as a white solid. MS m/z (ESI): 657.5[M+H]⁺; ¹H NMR (400 MHz, DMSO-d₆): δ 11.46 (br. s., 1H), 8.44-8.39 (m, 2H), 7.98 (d, 1H), 7.82 (dd, 1H), 7.44 (d, 1H), 7.39 (d, 1H), 6.92 (d, 1H), 6.51 (br. s., 1H), 5.85 (s, 1H), 5.58-5.46 (m, 1H), 4.95-4.88 (m, 2H), 4.32 (d, 2H), 3.56-350 (m, 4H), 2.62-2.56 (m, 4H), 2.28 (d, 2H), 2.22 (s, 3H), 2.14 (s, 3H), 2.09 (s, 3H), 1.54-1.50 (m, 2H), 1.08-1.04 (m, 2H), 1.01 (d, 6H).

EXAMPLE 57

Preparation of (3R)-1-(tert-butyl sulfinyl)-N-((4-methoxy-6-methyl-2-oxo-1,2-dihydropyridin-3-yl)methyl)-3-methyl-6-(4-methylpiperazin-1-yl)pyridin-3-yl)dihydroindole-4-carboxamide (Compound G-57)

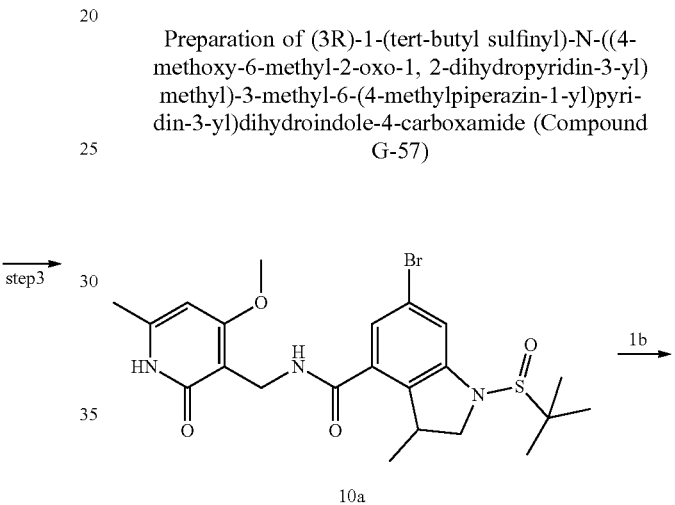

10a

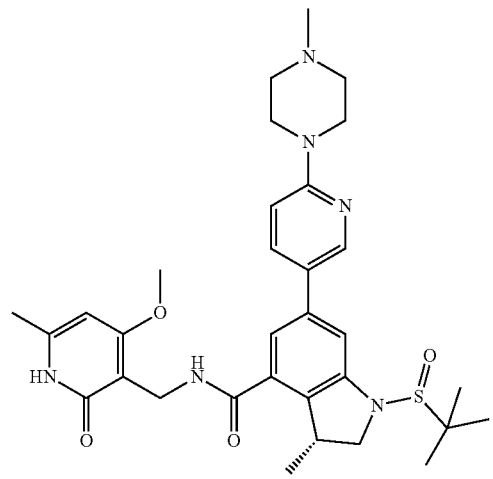

G-57

The preparation method was the same as that of compound G-2, except that compound G-1 in the preparation method of G-2 was replaced with compound 10a. MS m/z (ESI): 607[M+H]±0.1 H NMR (400 MHz, DMSO) δ11.46 (s, 1H), 8.45 (d, 1H), 8.19 (t, 1H), 7.87-7.84 (m, 1H), 7.26 (d, 1H), 7.12 (d, 1H), 6.90 (d, 1H), 6.10 (s, 1H), 4.24 (d, 2H), 3.79 (s, 3H), 3.77-3.74 (m, 1H), 3.68-3.66 (m, 2H), 3.53 (t, 4H), 2.43 (s, 4H), 2.24 (s, 3H), 2.18 (s, 3H), 1.24 (s, 9H), 1.03 (d, 3H).

EXAMPLES 49-56, 58-62, 74

General steps: compounds G-49 to G-56, G-58 to G-62 were prepared by a similar method to example 2 using intermediates 7a-11a as raw materials. The structures of examples 49-56, 58-62, and 74 are the structure of the compounds of formula (I) in which Z is —CH$_2$—, and R$_1$, R$_2$, S(O)$_2$R$_3$ have the following structures:

| Example No. | compound | R$_1$ | R$_2$ | S(O)$_2$R$_3$ | MS[M + H]$^+$ |
|---|---|---|---|---|---|
| 49 | G-49 | MeO | 5-(4-methylpiperazin-1-yl)pyridin-2-yl | 1-allylcyclopropyl sulfonyl | 647 |
| 50 | G-50 | MeO | 2-(4-methylpiperazin-1-yl)pyrimidin-5-yl | 1-allylcyclopropyl sulfonyl | 648 |
| 51 | G-51 | MeO | 4-(3-(dimethylamino)propoxy)phenyl | 1-allylcyclopropyl sulfonyl | 649 |
| 52 | G-52 | MeO | 4-(morpholinomethyl)phenyl | 1-allylcyclopropyl sulfonyl | 647 |
| 53 | G-53 | MeO | 5-(piperazin-1-yl)pyridin-2-yl | 1-allylcyclopropyl sulfonyl | 633 |
| 54 | G-54 | MeO | 5-(4-methylpiperazin-1-yl)pyridin-2-yl | isopropyl sulfonyl | 609 |
| 55 | G-55 | MeO | 5-(4-methylpiperazin-1-yl)pyridin-2-yl | methylsulfamoyl | 610 |
| 56 | G-56 | MeO | 2-(3-fluoroazetidin-1-yl)pyrimidin-5-yl | isopropyl sulfonyl | 585 |

-continued

| Example No. | compound | R₁ | R₂ | S(O)₂R₃ | MS[M + H]⁺ |
|---|---|---|---|---|---|
| 58 | G-58 | MeO | 5-(4-methylpiperazin-1-yl)pyridin-2-yl | tetrahydropyran-4-yl sulfonyl | 651 |
| 59 | G-59 | MeO | 3-((dimethylamino)methyl)phenyl | isopropylsulfonyl | 567 |
| 60 | G-60 | MeO | 3-fluoro-4-((dimethylamino)methyl)phenyl | isopropylsulfonyl | 585 |
| 61 | G-61 | MeO | 3-((dimethylamino)methyl)-4-fluorophenyl | isopropylsulfonyl | 585 |
| 62 | G-62 | MeO | 3-((dimethylamino)methyl)-4-fluorophenyl | isopropylsulfonyl | 585 |
| 74 | G-74 | Me | 4-((dimethylamino)methyl)phenyl | isopropylsulfonyl | 551 |

G-49 ¹H NMR (400 MHz, DMSO)δ8.37 (s, 1H), 8.23-8.18 (m, 1H), 7.77 (d, 1H), 7.52 (s, 1H), 7.29 (s, 1H), 6.93 (d, 1H), 6.10 (s, 1H), 5.78-5.68 (m, 1H), 5.01-4.96 (m, 2H), 4.23 (s, 2H), 4.13-4.07 (m, 1H), 3.80 (s, 4H), 3.65 (d, 1H), 3.54 (s, 3H), 3.37-3.34 (m, 1H), 2.42 (s, 8H), 2.20 (d, 4H), 1.33 (s, 2H), 1.24-1.16 (m, 3H), 1.01 (s, 2H).

G-50 ¹H NMR (400 MHz, DMSO)δ11.46 (s, 1H), 8.61 (s, 2H), 8.19 (t, 1H), 7.50 (d, 1H), 7.32 (d, 1H), 6.10 (s, 1H), 5.78-5.68 (m, 1H), 5.01-4.96 (m, 2H), 4.24 (d, 2H), 4.10 (t, 1H), 3.87-3.76 (m, 8H), 3.66 (q, 1H), 2.53 (s, 2H), 2.36 (t, 4H), 2.21 (s, 3H), 2.18 (s, 3H), 1.33 (t, 2H), 1.17 (d, 3H), 1.01 (t, 2H).

G-51 ¹H NMR (400 MHz, DMSO)δ11.45 (s, 1H), 8.25 (t, 1H), 7.55-7.52 (m, 3H), 7.29 (s, 1H), 7.02 (d, 2H), 6.10 (s, 1H), 5.78-5.68 (m, 1H), 5.01-4.96 (m, 2H), 4.24 (d, 2H), 4.11 (t, 1H), 4.03 (t, 2H), 3.79 (s, 4H), 3.65 (q, 1H), 2.53 (s, 3H), 2.38 (t, 2H), 2.18-2.16 (m, 8H), 1.89-1.82 (m, 2H), 1.33 (t, 2H), 1.17 (d, 3H), 1.01 (t, 2H).

G-52 ¹H NMR (400 MHz, DMSO)δ11.45 (s, 1H), 8.25 (t, 1H), 7.60-7.55 (m, 3H), 7.40 (d, 2H), 7.34 (d, 1H), 6.10 (s, 1H), 5.78-5.68 (m, 1H), 5.01-4.96 (m, 2H), 4.24 (d, 2H), 4.12 (t, 1H), 3.87-3.84 (m, 1H), 3.80 (s, 3H), 3.66 (q, 1H), 3.58 (t, 4H), 3.49 (s, 2H), 2.53 (d, 2H), 2.37 (s, 4H), 2.18 (s, 3H), 1.33 (t, 2H), 1.18 (d, 3H), 1.02 (t, 2H).

G-53 ¹H NMR (400 MHz, DMSO)δ11.44 (s, 1H), 8.36 (d, 1H), 8.23 (t, 1H), 7.77 (q, 1H), 7.53 (d, 1H), 7.30 (d, 1H), 6.89 (d, 1H), 6.10 (s, 1H), 5.77-5.08 (m, 1H), 5.01-4.96 (m, 2H), 4.24 (d, 2H), 4.10 (t, 1H), 3.87-3.84 (m, 1H), 3.80 (s, 3H), 3.63-3.51 (m, 2H), 3.47 (t, 4H), 2.80 (t, 4H), 2.53 (s, 2H), 2.18 (s, 3H), 1.33 (t, 2H), 1.17 (d, 3H), 1.01 (t, 2H).

G-54 ¹H NMR (400 MHz, DMSO-d₆): δ 11.46 (br. s., 1H), 8.40 (d, 1H), 8.24-8.20 (m, 1H), 7.79 (dd, 1H), 7.42 (d, 1H), 7.27 (d, 1H), 6.93 (d, 1H), 6.10 (s, 1H), 4.23 (d, 2H), 4.13-4.10 (m, 1H), 3.80-3.65 (m, 7H), 3.34-3.30 (m, 3H), 2.52-2.50 (m, 4H), 2.32 (s, 3H), 2.18 (s, 3H), 1.27 (d, 6H), 1.15 (d, 3H).

| | -continued |
|---|---|
| G-55 | ¹H NMR (400 MHz, DMSO)δ11.46 (s, 1H), 8.37 (d, 1H), 8.21 (t, 1H), 7.78 (q, 1H), 7.41 (d, 1H), 7.28 (d, 1H), 6.91 (d, 1H), 6.10 (s, 1H), 4.24 (d, 2H), 4.05 (t, 1H), 3.87-3.84 (m, 1H), 3.79 (s, 3H), 3.59 (q, 1H), 3.53 (t, 4H), 2.85 (s, 6H), 2.40 (t, 4H), 2.20 (d, 6H), 1.17 (d, 3H). |
| G-56 | ¹H NMR (400 MHz, DMSO-d₆): δ 11.41 (br. s., 1H), 8.62 (s, 2H), 8.17-8.13 (m, 1H), 7.36 (d, 1H), 7.25 (d, 1H), 6.06 (s, 1H), 5.57-5.39 (m, 1H), 4.25-4.32 (m, 2H), 4.19 (d, 2H), 4.14-4.03 (m, 3H), 3.82-3.78 (m, 1H), 3.75 (s, 3H), 3.74-3.70 (m, 1H), 3.62 (dd, 1H), 2.14 (s, 3H), 1.22 (d, 6H), 1.11 (d, 3H). |
| G-58 | 1H NMR (400 MHz, DMSO)δ11.46 (s, 1H), 8.41 (d, 1H), 8.21 (t, 1H), 7.81 (q, 1H), 7.45 (d, 1H), 7.28 (d, 1H), 6.92 (d, 1H), 6.10 (s, 1H), 4.24 (d, 2H), 4.15 (t, 1H), 3.90-3.82 (m, 4H), 3.79 (s, 3H), 3.67 (q, 1H), 3.53 (t, 5H), 2.47 (s, 1H), 2.42 (t, 4H), 2.23 (s, 3H), 2.18 (s, 3H), 1.82-1.69 (m, 4H), 1.16 (d, 3H). |
| G-59 | 1H NMR (500 MHz, DMSO-d6): δ 11.44 (br. s., 1H), 8.28-8.25 (m, 1H), 7.52-7.46 (m, 3H), 7.42 (t, 1H), 7.32-7.29 (m, 2H), 6.09 (s, 1H), 4.23 (d, 2H), 4.15 (t, 1H), 3.85-3.82 (m, 1H), 3.79 (s, 3H), 3.74-3.70 (m, 1H), 3.67 (dd, 1H), 3.50 (br. s., 2H), 2.20-1.73 (m, 9H), 1.27 (d, 6H), 1.17 (d, 3H). |
| G-60 | 1H NMR (500 MHz, DMSO-d₆): δ 11.45 (br. s., 1H), 7.66-7.61 (m, 1H), 7.59-7.54 (m, 1H), 7.52-7.48 (m, 1H), 7.21 (s, 2H), 6.09 (s, 1H), 4.23-4.22 (m, 2H), 4.15 (t, 1H), 3.89-3.84 (m, 1H), 3.78 (s, 3H), 3.70-3.65 (m, 2H), 3.50-3.44 (m, 2H), 2.19-2.16 (m, 9H), 1.26 (dd, 6H), 1.18 (d, 3H). |
| G-61 | 1H NMR (500 MHz, DMSO-d6): δ 11.37 (br. s., 1H), 8.17-8.15 (m, 1H), 7.40-7.36 (m, 2H), 7.30-7.26 (m, 1H), 7.22-7.18 (m, 1H), 7.11 (s, 1H), 6.02 (s, 1H), 4.16 (d, 2H), 4.08 (t, 1H), 3.80-3.77 (m, 1H), 3.72 (s, 3H), 3.63-3.58 (m, 2H), 3.49-3.48 (m, 2H), 2.14-2.10 (m, 9H), 1.19 (dd, 6H), 1.11 (d, 3H). |
| G-62 | 1H NMR (400 MHz, DMSO-d6): δ 11.42 (br. s., 1H), 8.25-8.22 (m, 1H), 7.59-7.51 (m, 3H), 7.43 (br. s., 1H), 7.27-7.22 (m, 2H), 6.06 (s, 1H), 4.20 (d, 2H), 4.15-4.08 (m, 1H), 3.76 (s, 3H), 3.71-3.67 (m, 1H), 3.66-3.61 (m, 1H), 3.47 (br. s., 2H), 2.14 (m, 9H), 1.23 (d, 6H), 1.13 (d, 3H). |
| G-74 | 1H NMR (400 MHz, DMSO-d6): δ 11.49 (br. s., 1H), 8.46 (t, 1H), 7.60 (d, 2H), 7.51 (s, 1H), 7.42 (d, 2H), 7.36 (s, 1H), 5.86 (s, 1H), 4.29 (d, 2H), 4.14 (t, 1H), 3.88-3.86 (m, 1H), 3.76-3.70 (m, 1H), 3.67 (dd, 1H), 3.58 (br. s., 2H), 2.26 (s, 6H), 2.20 (s, 3H), 2.11 (s, 3H), 1.27 (d, 6H), 1.13 (d, 3H). |

EXAMPLE 66

Preparation of 1-(1-allylcyclopropylsulfonyl)-6-chloro-N-((4-methoxy-6-methyl-2-oxo-1,2-dihydro-pyridin-3-yl)methyl)-3-methyl-1H-indole-4-carboxamide (Compound G-66)

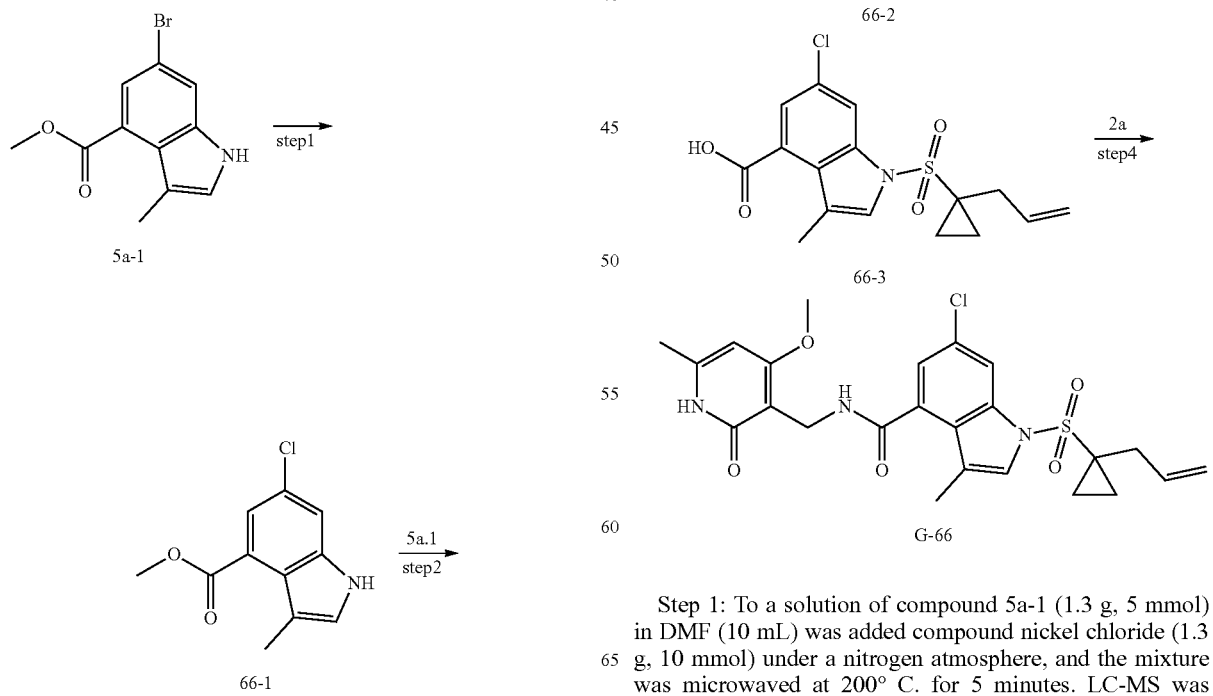

Step 1: To a solution of compound 5a-1 (1.3 g, 5 mmol) in DMF (10 mL) was added compound nickel chloride (1.3 g, 10 mmol) under a nitrogen atmosphere, and the mixture was microwaved at 200° C. for 5 minutes. LC-MS was followed until the reaction was completed. The reaction solution was concentrated and purified by combiflash to give compound 66-1 (1 g, 91%). MS m/z (ESI): 224[M+H]+.

Step 2: The preparation method was the same as that of compound 5a-2, except that compound 5a-1 in the preparation method of 5a-2 was replaced with compound 66-1. MS m/z (ESI): 368 [M+H]+.

Step 3: The preparation method was the same as that of compound 5a, except that compound 5a-2 in the preparation method of 5a was replaced with compound 66-2. MS m/z (ESI): 352 [M+H]+.

Step 4: The preparation method was the same as that of compound 6a, except that compound 5a in the preparation method of 6a was replaced with compound 66-3. MS m/z (ESI): 504[M+H]+; $^1$H NMR (400 MHz, DMSO) δ11.45 (s, 1H), 8.29 (t, 1H), 7.86 (d, 1H), 7.53 (d, 1H), 7.19 (d, 1H), 6.09 (s, 1H), 5.56-5.46 (m, 1H), 4.96-4.91 (m, 2H), 4.26 (d, 2H), 3.80 (s, 3H), 2.30 (d, 2H), 2.18 (s, 6H), 1.55 (t, 2H), 1.10 (t, 2H).

EXAMPLE 67

Preparation of 1-(1-allylcyclopropylsulfonyl)-6-(2-(4-isopropylpiperidin-1-yl) pyrimidin-5-yl)-N-((4-methoxy-6-methyl-2-oxo-1,2-dihydropyridin-3-yl) methyl)-3-methyl-1H-indole-4-carboxamide (Compound G-67)

The preparation method was the same as that of compound G-48, except that compound 48-2 in the preparation method of G-48 was replaced with compound G-65. After purification by Prep-HPLC, compound G-67(10.6 mg, 8.6%) was obtained as a white solid. MS m/z (ESI): 674.4 [M–H]+; $^1$H NMR (400 MHz, DMSO-d$_6$): δ 8.67 (s, 2H), 8.24-8.21 (m, 1H), 7.98 (d, 1H), 7.48 (d, 1H), 7.42 (d, 1H), 6.09 (s, 1H), 2.58-5.50 (m, 1H), 4.97-4.91 (m, 2H), 4.29 (d, 2H), 3.80 (s, 3H), 3.78-3.76 (m, 4H), 2.72-2.66 (m, 1H), 2.54-2.52 (m, 4H), 2.30 (d, 2H), 2.19 (d, 6H), 1.57-1.55 (m, 2H), 1.09-1.05 (m, 2H), 1.00 (d, 6H).

EXAMPLE 68

Preparation of 1-(1-allylcyclopropylsulfonyl)-N-((4-(difluoromethoxy)-6-methyl-2-oxo-1,2-dihydropyridin-3-yl)methyl)-3-methyl-6-(4-methylpiperazin-1-yl) pyridin-3-yl)-1H-indole-4-carboxamide (Compound G-68)

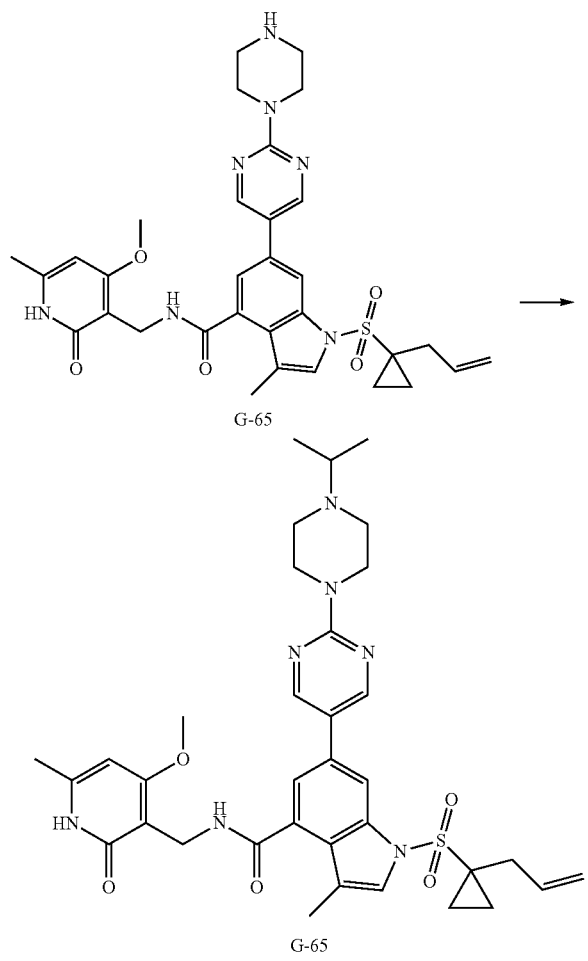

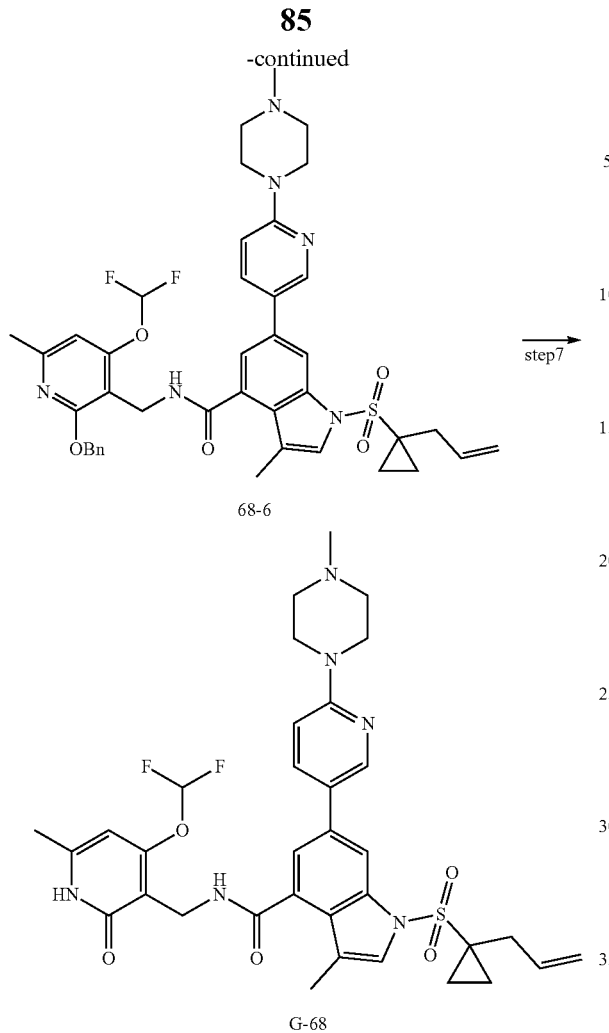

68-6

G-68

Step 7: A solution of compound 68-6 (45 mg, 0.58 mmol) in trifluoroacetic acid (3 mL) was stirred at room temperature for 2 hours. LC-MS was followed until the reaction was completed. The reaction solution was concentrated and purified by Prep-HPLC to give the compound G-68 (5 mg, 12.5%). MS m/z (ESI): 681[M+H]$^+$; $^1$H NMR (400 MHz, DMSO-d$_6$): δ 11.84 (br. s., 1H), 8.44-8.37 (m, 2H), 7.98 (s, 1H), 7.80 (dd, 1H), 7.42-7.44 (m, 1H), 7.39 (br. s., 1H), 6.92 (d, 1H), 6.03 (s, 1H), 5.55-5.47 (m, 1H), 4.94-4.87 (m, 2H), 4.27 (d, 2H), 3.52-3.50 (m, 4H), 3.13 (d, 1H), 2.39-2.37 (m, 4H), 2.27 (d, 2H), 2.20 (s, 3H), 2.15 (d, 6H), 1.53-1.50 (m, 2H), 1.07-1.03 (m, 2H).

EXAMPLE 69

Preparation of 1-(1-allylcyclopropylsulfonyl)-N-((4-methoxy-6-methyl-2-oxo-1,2-dihydropyridin-3-yl) methyl)-3-methyl-6-(4-methylpiperazin-1-yl) piperidin-1-yl)-1H-indole-4-carboxamide (Compound G-69)

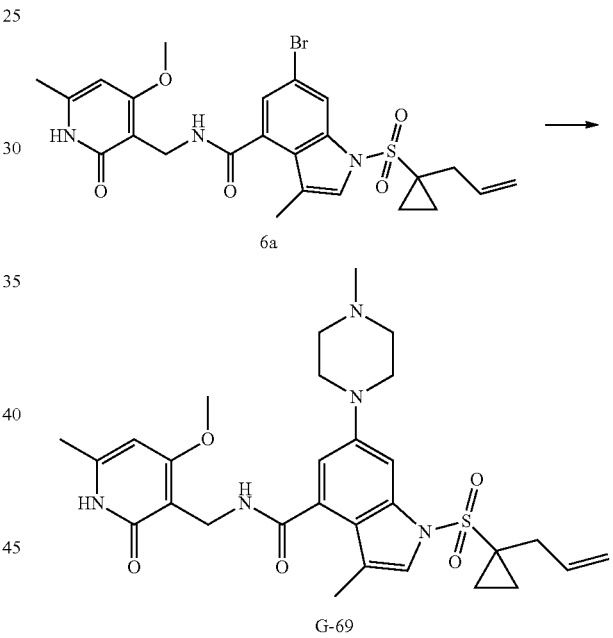

6a

G-69

Step 1: A solution of compound 2a-4 (2 g, 11.9 mmol), benzyl chloride (1.8 g, 14.2 mmol) and silver oxide (3 g, 13.1 mmol) in toluene (100 mL) was stirred under reflux for 16 hours. LC-MS was followed until the reaction was completed. The reaction solution was filtered and the filtrate was concentrated and compound 68-1 (650 mg, 21%) was obtained by combiflash. MS m/z (ESI): 241 [M+H]$^+$.

Step 2: The preparation method was the same as that of compound 2a-4, except that compound 2a-3 in the preparation method of 2a-4 was replaced with compound 68-1. MS m/z (ESI): 259 [M+H]$^+$.

Step 3: The preparation method was the same as that of compound 5a-2, except that compounds 5a-1 and 5a.1 in the preparation method of 5a-2 were replaced with compound 68-2 and ethyl difluorochloroacetate. MS m/z (ESI): 291 [M+H]$^+$.

Step 4: The preparation method was the same as that of compound 14a-2, except that compound 14a-1 in the preparation method of 14a-2 was replaced with compound 68-3. MS m/z (ESI): 295 [M+H]$^+$.

Step 5: The preparation method was the same as that of compound G-1, except that compound 1a in the preparation method of G-1 was replaced with compound 68-4. MS m/z (ESI): 584[M+H]$^+$.

Step 6: The preparation method was the same as that of compound G-2, except that compound G-1 in the preparation method of G-2 was replaced with compound 68-5. MS m/z (ESI): 771[M+H]$^+$.

A solution of compound 6a (55 mg, 0.1 mmol), N-methylpiperazine (30 mg, 0.3 mmol), Xantphos (6 mg, 0.01 mmol), Pd$_2$(dba)$_3$ (10 mg, 0.01 mmol), and sodium tert-butoxide (30 mg, 0.3 mmol) in 1,4-dioxane (5 mL) was microwaved under argon atmosphere at 130° C. for 20 minutes. LC-MS was followed until the reaction was completed. The reaction solution was filtered, concentrated and purified by Prep-HPLC to give compound G-69 (5 mg, 9%). MS m/z (ESI): 568 [M+H]$^+$; $^1$H NMR (400 MHz, DMSO) δ11.43 (s, 1H), 8.09 (t, 1H), 7.33 (d, 1H), 7.22 (d, 1H), 6.88 (d, 1H), 6.09 (s, 1H), 5.59-5.50 (m, 1H), 4.98-4.93 (m, 2H), 4.25 (d, 2H), 3.80 (s, 3H), 3.13 (t, 4H), 2.47 (t, 4H), 2.27 (d, 2H), 2.22 (s, 3H), 2.17 (s, 3H), 2.12 (d, 3H), 1.48 (t, 2H), 1.03 (t, 2H). Examples 75-80

Compounds G-75 to G-80 can be synthesized according to the similar preparation method of the examples above.

Example 75
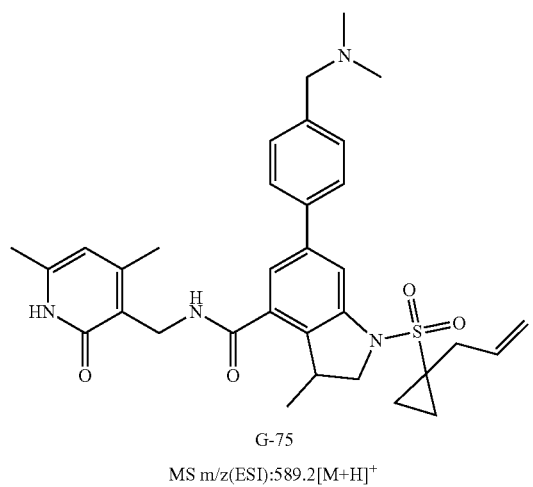
G-75
MS m/z(ESI):589.2[M+H]+
Example 76
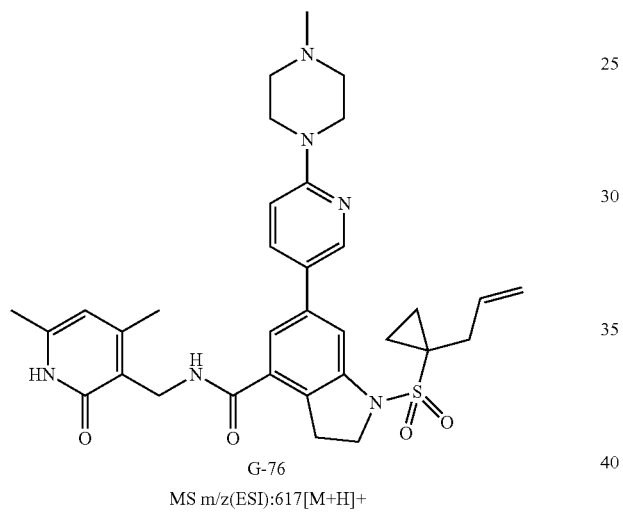
G-76
MS m/z(ESI):617[M+H]+
Example 77
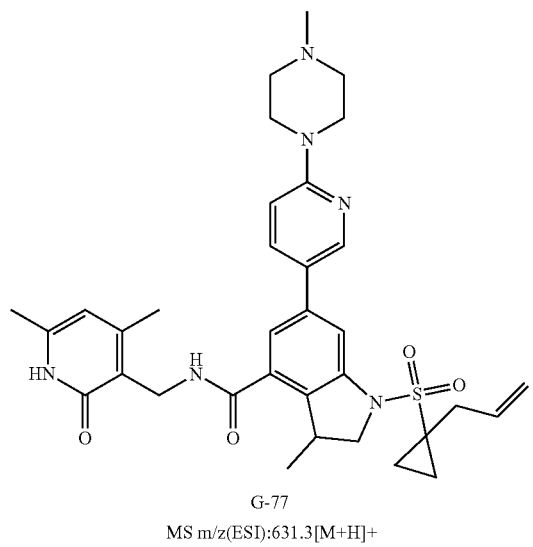
G-77
MS m/z(ESI):631.3[M+H]+
Example 78
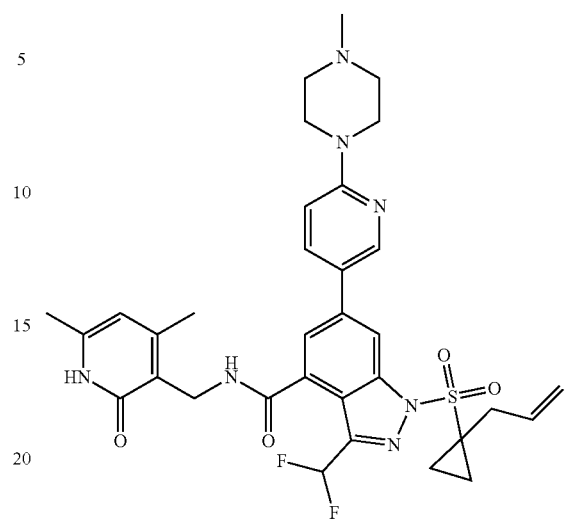
G-78
MS m/z(ESI):666[M+H]+
Example 79
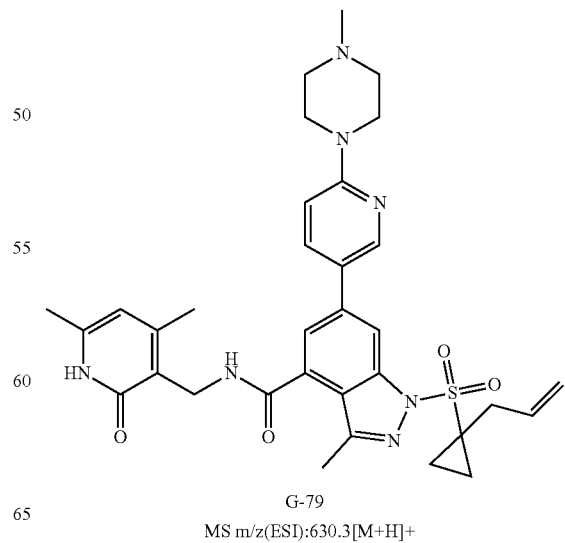
G-79
MS m/z(ESI):630.3[M+H]+

-continued

Example 80

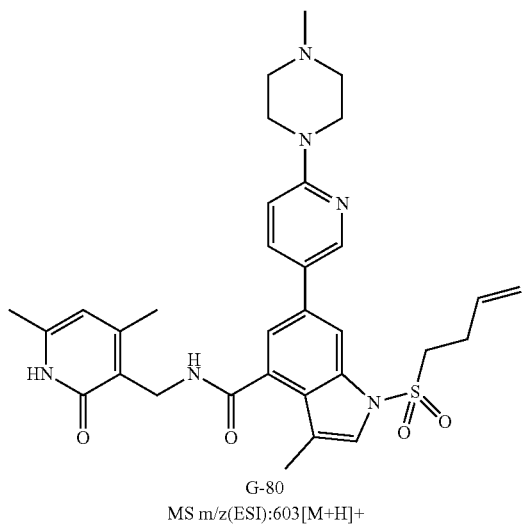

G-80
MS m/z(ESI):603[M+H]+

Example 81

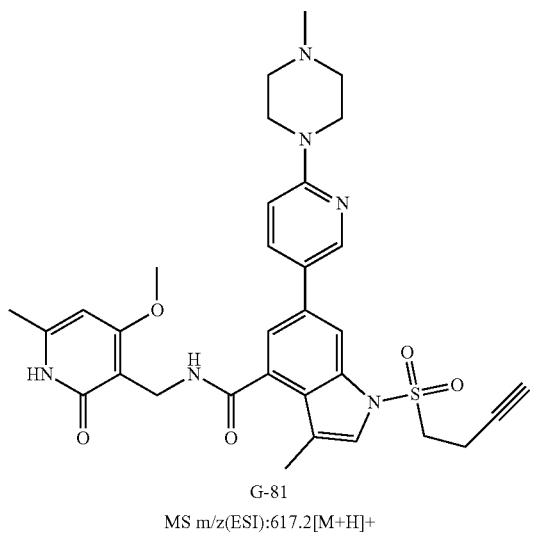

G-81
MS m/z(ESI):617.2[M+H]+

Bioassay

TEST EXAMPLE 1

In Vitro Methyltransferase Activity Test

Recombinant PRC2 (EZH2-Y641F) was purchased from Active motif company, S-adenosyl-methionine (SAM) and Poly-L-lysine (PLL) were purchased from Sigma-Aldrich company, and H3(1-50)K27me1 peptide was purchased from Cisbio company. The detection system uses LAN-CEUltra system (Perkinelmer company). In the enzyme activity test, compounds to be tested were diluted by 8 gradient points in a ratio of 1:3, and added into a reaction plate, then 100 ng recombinase was added. And then a buffer [20 mM Tris pH8.5, 2 mM MgCl2, 0.01% Tween-20, 1 mM TCEP] containing 2.5 μM SAM/250 nM H3 (1-50)K27me1 premixtures was added, thus the enzyme reaction was started at room temperature. After reacting for 3 hours, a test solution premixed with PLL, detection antibody and Ulight was added, and reacted for 1h at room temperature, then the fluorescence value was read on a Tecan infinite pro. IC50 was calculated by fitting a four-factor model in the XLfit software. The results were shown in Table 1:

TABLE 1

Inhibitory Activity of Compounds against EZH2 Y641F

| compound | EZH2 Y641F IC$_{50}$(μM) | compound | EZH2 Y641F IC$_{50}$(μM) | compound | EZH2 Y641F IC$_{50}$(μM) |
|---|---|---|---|---|---|
| G-2 | 0.014 | G-3 | 0.028 | G-4 | 0.022 |
| G-5 | 0.017 | G-6 | 0.019 | G-7 | 0.033 |
| G-8 | 0.040 | G-9 | 0.035 | G-10 | 0.041 |
| G-11 | 0.032 | G-12 | 0.058 | G-13 | 0.013 |
| G-14 | 0.005 | G-15 | 0.025 | G-16 | 0.023 |
| G-17 | 0.045 | G-18 | 0.042 | G-19 | 0.036 |
| G-20 | 0.021 | G-21 | 0.037 | G-22 | 0.031 |
| G-23 | 0.005 | G-24 | 0.032 | G-25 | 0.037 |
| G-26 | 0.043 | G-27 | 0.024 | G-28 | 0.009 |
| G-29 | 0.008 | G-30 | 0.009 | G-31 | 0.031 |
| G-32 | 0.008 | G-33 | 0.036 | G-34 | 0.032 |
| G-35 | 0.012 | G-36 | 0.016 | G-37 | 0.017 |
| G-38 | 0.031 | G-39 | 0.009 | G-40 | 0.015 |
| G-41 | 0.035 | G-42 | 0.021 | G-43 | 0.033 |
| G-44 | 0.010 | G-48 | 0.028 | G-63 | 0.005 |
| G-65 | 0.017 | G-67 | 0.007 | G-68 | 0.034 |
| G-69 | 0.026 | G-70 | 0.027 | G-71 | 0.027 |
| G-72 | 0.023 | G-73 | 0.015 | G-46 | 0.052 |
| G-47 | 0.160 | G-74 | 0.094 | G-75 | 0.280 |
| G-76 | 0.460 | G-77 | 0.147 | G-78 | 1.418 |
| G-79 | 0.585 | G-80 | 0.145 | G-81 | 0.196 |

TEST EXAMPLE 2

Cell Proliferation Test

The used cell lines Pfeiffer (CRL-2632), suDHL-6 (CRL-2959) and suDHL-10 (CRL-2963) were purchased from American Type Culture Collection (ATCC). All cell lines were cultured in RPMI-1640 medium (Gibco) containing 10% fetal bovine serum (Gibco). The cultured cells were collected by centrifugation and the cell density was measured on a CounterStar counter. Appropriate number of cells were then seeded in a 96-well culture plate and incubated overnight. Compounds to be tested were diluted by 8 gradient points in a ratio of 1:3 and added into the corresponding wells. After continuing to culture for 6 days, the number of viable cells was measured with Cell counting kit-8, and the absorbance value was read on Tecan infinite pro. The IC50 was calculated by fitting a four-parameter model in the XLfit software. The results were shown in Table 2:

TABLE 2

Inhibitory Activity of Compounds against Pfeiffer cells

| compound | Pfeiffer IC$_{50}$(μM) | compound | Pfeiffer IC$_{50}$(μM) | compound | Pfeiffer IC$_{50}$(μM) |
|---|---|---|---|---|---|
| G-2 | 0.236 | G-3 | 0.300 | G-5 | 0.429 |
| G-6 | 0.352 | G-7 | 0.380 | G-8 | 0.327 |
| G-9 | 0.450 | G-12 | 0.485 | G-13 | 0.075 |
| G-14 | 0.027 | G-15 | 0.219 | G-16 | 0.335 |
| G-17 | 0.242 | G-18 | 0.368 | G-20 | 0.012 |
| G-22 | 0.073 | G-23 | 0.048 | G-24 | 0.060 |
| G-26 | 0.072 | G-27 | 0.066 | G-28 | 0.018 |
| G-29 | 0.142 | G-30 | 0.097 | G-31 | 0.180 |
| G-32 | 0.079 | G-33 | 0.177 | G-34 | 0.087 |
| G-35 | 0.262 | G-36 | 0.085 | G-37 | 0.099 |
| G-38 | 0.064 | G-39 | 0.046 | G-40 | 0.130 |
| G-41 | 0.049 | G-42 | 0.027 | G-44 | 0.129 |
| G-48 | 0.211 | G-63 | 0.091 | G-65 | 0.171 |
| G-67 | 0.022 | G-68 | 0.152 | G-70 | 0.200 |

TABLE 2-continued

Inhibitory Activity of Compounds against Pfeiffer cells

| compound | Pfeiffer IC$_{50}$(μM) | compound | Pfeiffer IC$_{50}$(μM) | compound | Pfeiffer IC$_{50}$(μM) |
|---|---|---|---|---|---|
| G-72 | 0.209 | G-73 | 0.065 | G-46 | 0.870 |
| G-47 | 2.042 | G-74 | 1.046 | G-75 | 1.838 |
| G-76 | 2.592 | G-77 | 1.528 | G-78 | 2.517 |
| G-79 | 2.815 | G-80 | 1.650 | G-81 | 3.798 |

It can be seen from Table 1 and Table 2 that the representative compounds of the present disclosure have a high inhibitory activity against EZH2 enzymes and cells, and studies have found that the choice of the parent nucleus benzoheterocycle has a greater effect on the enzyme activity, particularly the inhibitory activity of cells. When the parent nucleus is changed from 1H-Indole to indoline or 1H-indazole (for example, G-75 and G-6, G-77, G-79 and G-2), the inhibitory activity against the enzyme, especially cells, is significantly reduced, and when the hydrogen at 3-position of the 5-membered heterocycle in the parent nucleus is replaced with methyl (for example, G-76 and G-77, G-46 and G-2), the inhibitory activity against enzymes, particularly cells, is significantly increased, and the 3-position substituent is changed from methyl to another substituent such as difluromethyl (for example, G-78 and G-2), the inhibitory activities against enzymes and cells are greatly reduced. In addition, when the parent nucleus is 1H-Indole, the substituents of the sulfuryl (for example, G-80 and G-2, G-81 and G-14) have a great influence on the inhibitory activity of enzymes, especially cells.

All publications mentioned herein are incorporated by reference as if each individual document is cited as a reference, as in the present application. It should also be understood that, after reading the above teachings of the present disclosure, those skilled in the art can make various changes or modifications, equivalents of which fall in the scope of claims as defined in the appended claims.

The invention claimed is:

1. A compound of formula (I), or a pharmaceutically acceptable salt, stereoisomer, solvate or prodrug thereof:

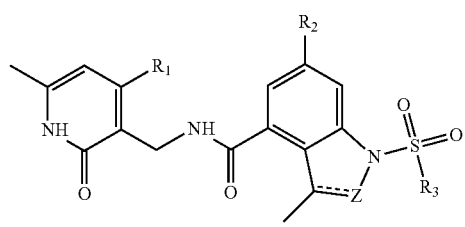

(I)

wherein,

Z is =CH—, —CH$_2$— or =N—;

" ---------- " is a single bond or double bond;

R$_1$ is a halogen, C$_{1-8}$ alkyl, halogenated C$_{1-8}$ alkoxy, C$_{1-8}$ alkoxy, NR$_{a0}$R$_{b0}$;

R$_2$ is a hydrogen, halogen, CN, C$_{6-10}$ aryl, 4 to 6 membered saturated or partially unsaturated single heterocycle, 5 to 6 membered single heteroaryl ring;

R$_3$ is a C$_{1-8}$ alkyl, C$_{2-8}$ alkynyl, C$_{6-10}$ aryl, C$_{3-8}$ cycloalkyl, 4 to 6 membered saturated or partially unsaturated single heterocycle or NR$_{a0}$R$_{b0}$;

the alkyl, cycloalkyl, alkoxy, aryl, 4 to 6 membered saturated or partially unsaturated single heterocycle, 5 to 6 membered single heteroaryl ring is unsubstituted or substituted by 1, 2 or 3 substituents selected from the group consisting of acetyl, hydroxy, hydroxymethyl, hydroxyethyl, carboxyl, —C(O)OC$_{1-6}$ alkyl, CN, 4 to 6 membered saturated single heterocycle, NR$_{a1}$R$_{b1}$, halogen, C$_{1-8}$ alkyl, C$_{1-8}$ alkoxy, halogenated C$_{1-8}$ alkyl, C$_{2-8}$ alkenyl, and —CH$_2$-L$_1$; L$_1$ is 4 to 6 membered saturated single heterocycle or NR$_{a1}$R$_{b1}$;

R$_{a0}$, R$_{b0}$, R$_{a1}$, R$_{b1}$ are each independently hydrogen or C$_{1-8}$ alkyl.

2. The compound of claim 1, or the pharmaceutically acceptable salt, stereoisomer, solvate or prodrug thereof, wherein Z is =CH—; " ---------- " is a double bond.

3. The compound of claim 1, or the pharmaceutically acceptable salt, stereoisomer, solvate or prodrug thereof, wherein Z is —CH$_2$—; " ---------- " is a single bond.

4. The compound of claim 1, or the pharmaceutically acceptable salt, stereoisomer, solvate or prodrug thereof, wherein Z is =N—; " ---------- " is a double bond.

5. The compound of claim 1, or the pharmaceutically acceptable salt, stereoisomer, solvate or prodrug thereof, wherein R$_1$ is fluorine, chlorine, methyl, ethyl, propyl, methoxy, ethoxy, isopropoxy, trifluoro substituted ethoxy, difluoro substituted methoxy, NHCH$_3$.

6. The compound of claim 1, or the pharmaceutically acceptable salt, stereoisomer, solvate or prodrug thereof, wherein R$_2$ is hydrogen, halogen or CN.

7. The compound of claim 1, or the pharmaceutically acceptable salt, stereoisomer, solvate or prodrug thereof, wherein R$_2$ is C$_{6-10}$ aryl; the aryl is unsubstituted or substituted by 1, 2 or 3 groups selected from the group consisting of halogen, CN, C$_{1-3}$ alkyl, halogenated C$_{1-3}$ alkyl, C$_{1-3}$ alkoxy, NR$_{a1}$R$_{b1}$, 4 to 6 membered saturated single heterocycle, —CH$_2$-L$_2$ and —O(CH$_2$)$_n$NR$_{a1}$R$_{b1}$; wherein L$_2$ is 4 to 6 membered saturated single heterocycle or NR$_{a1}$R$_{b1}$; wherein n is 1, 2 or 3;

the 4 to 6 membered saturated single heterocycle is unsubstituted or substituted by 1, 2 or 3 groups selected from the group consisting of halogen, halogenated C$_{1-3}$ alkyl, C$_{1-3}$ alkyl, CN and NR$_{a1}$R$_{b1}$; wherein R$_{a1}$, R$_{b1}$ are each independently hydrogen or C$_{1-3}$ alkyl.

8. The compound of claim 1, or the pharmaceutically acceptable salt, stereoisomer, solvate or prodrug thereof, wherein R$_2$ is 4 to 6 membered saturated or partially unsaturated single heterocycle; the 4 to 6 membered saturated or partially unsaturated single heterocycle is unsubstituted or substituted by 1, 2 or 3 groups selected from the group consisting of halogen, halogenated C$_{1-3}$ alkyl, C$_{1-3}$ alkyl, CN and NR$_{a1}$R$_{b1}$; wherein R$_{a1}$, R$_{b1}$ are each independently hydrogen or C$_{1-3}$ alkyl.

9. The compound of claim 1, or the pharmaceutically acceptable salt, stereoisomer, solvate or prodrug thereof, wherein R$_2$ is 5 to 6 membered single heteroaryl ring; the 5 to 6 membered single heteroaryl ring is unsubstituted or substituted by 1, 2 or 3 groups selected from the group consisting of halogen, C$_{1-3}$ alkyl, CN, halogenated C$_{1-3}$ alkyl, C$_{1-3}$ alkoxy, NR$_{a1}$R$_{b1}$, 4 to 6 membered saturated single heterocycle and —CH$_2$-L$_2$; wherein L$_2$ is 4 to 6 membered saturated single heterocycle or NR$_{a1}$R$_{b1}$; R$_{a1}$, R$_{b1}$ are each independently hydrogen or C$_{1-3}$ alkyl;

the 4 to 6 membered saturated single heterocycle is unsubstituted or substituted by 1, 2 or 3 groups selected from the group consisting of halogen, halogenated C$_{1-3}$ alkyl, C$_{1-3}$ alkyl, CN and NR$_{a1}$R$_{b1}$;

R$_2$ is 5 to 6 membered single heteroaryl ring; the 5 to 6 membered single heteroaryl ring is unsubstituted or substituted by 1, 2 or 3 groups selected from the group consisting of halogen, CN, $C_{1-3}$ alkyl, $NR_{a1}R_{b1}$, 4 to 6 membered saturated single heterocycle and —$CH_2$-$L_2$; wherein $L_2$ is 4 to 6 membered saturated single heterocycle or $NR_{a1}R_{b1}$; $R_{a1}$, $R_{b1}$ are each independently hydrogen or $C_{1-3}$ alkyl;

the 4 to 6 membered saturated single heterocycle is unsubstituted or substituted by 1, 2 or 3 groups selected from the group consisting of halogen, halogenated $C_{1-3}$ alkyl, $C_{1-3}$ alkyl.

10. The compound of claim 1, or the pharmaceutically acceptable salt, stereoisomer, solvate or prodrug thereof, wherein $R_2$ is hydrogen, fluorine, chlorine, bromine, CN; or $R_2$ is the following structure:

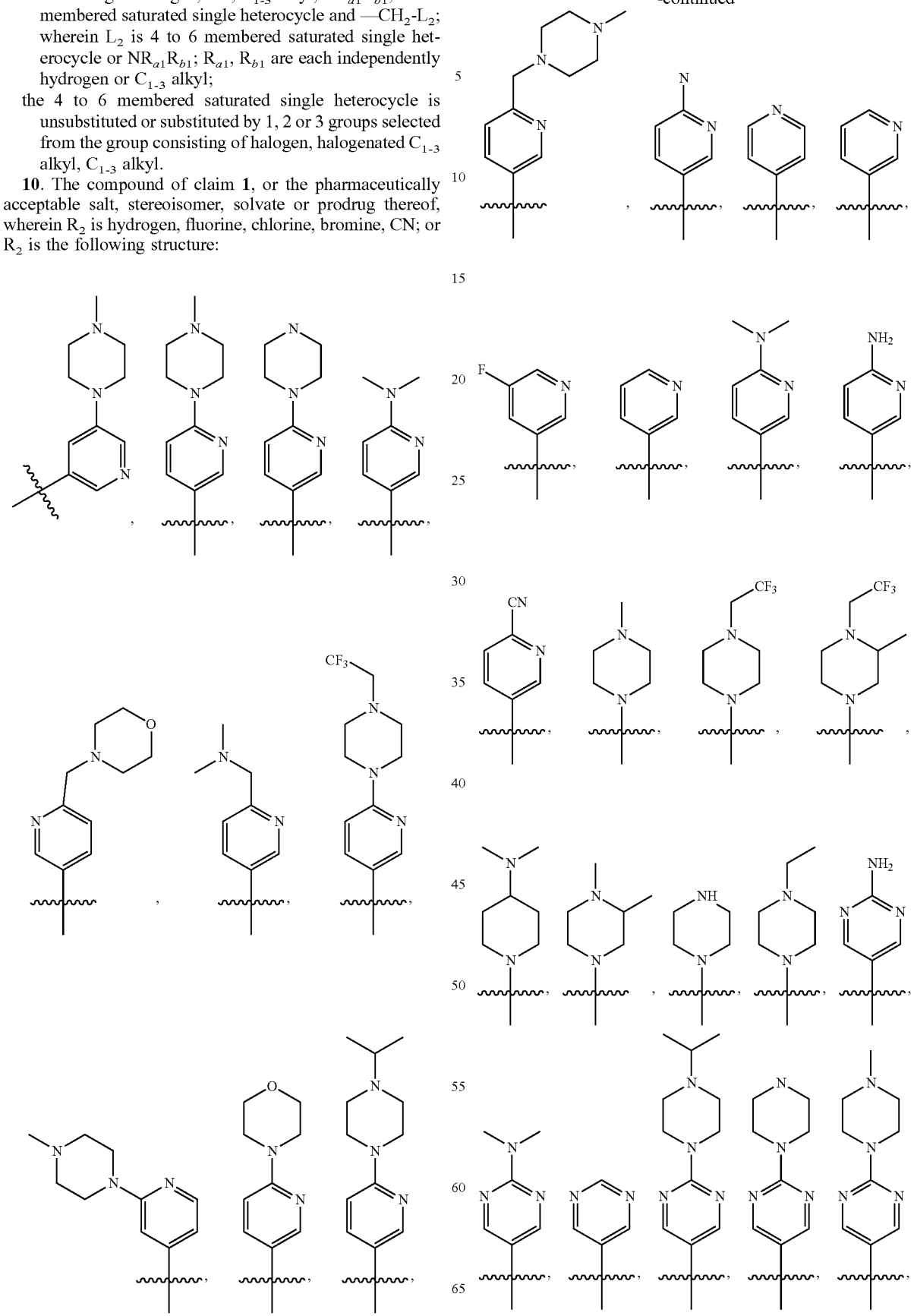

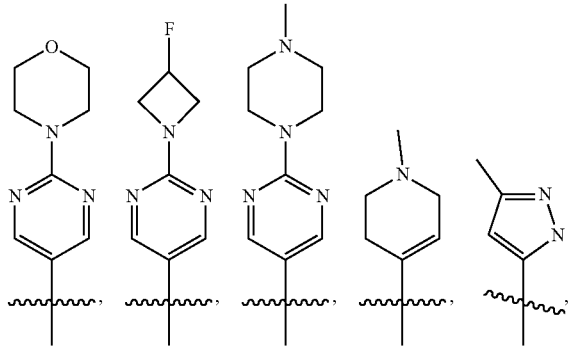
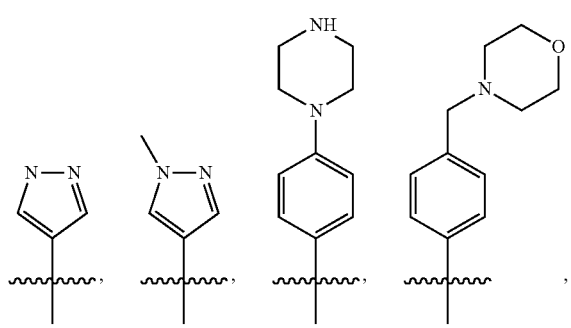
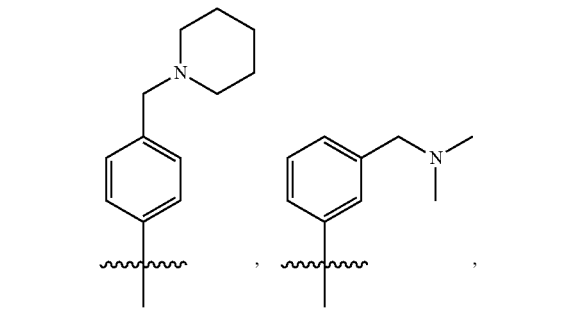
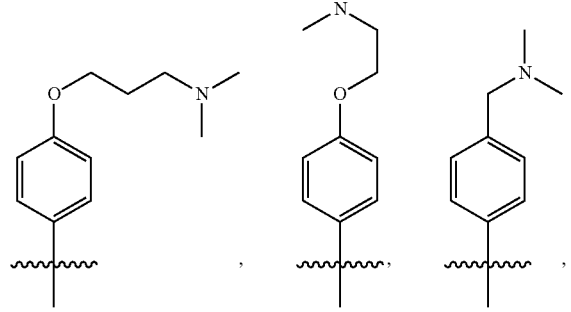
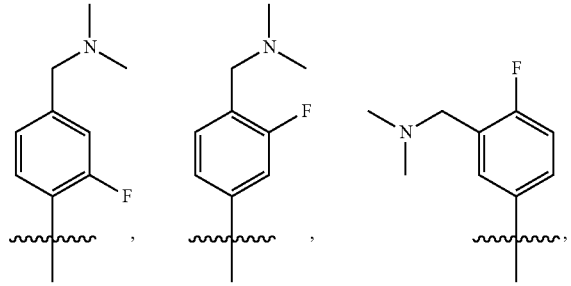

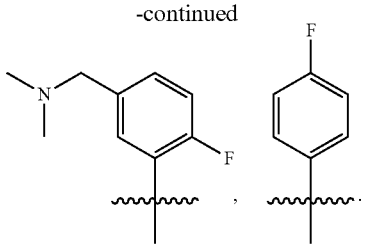

11. The compound of claim 1, or the pharmaceutically acceptable salt, stereoisomer, solvate or prodrug thereof, wherein $R_3$ is $C_{1-8}$ alkyl, $C_{1-8}$ alkyl substituted by $C_{1-8}$ alkoxy, $C_{2-8}$ alkynyl, 4 to 6 membered saturated single heterocycle, phenyl, $C_{3-8}$ cycloalkyl, $NR_{a0}R_{b0}$; wherein $R_{a0}$, $R_{b0}$ are each independently hydrogen or $C_{1-8}$ alkyl;
the phenyl, 4 to 6 membered saturated single heterocycle is unsubstituted or substituted by 1, 2 or 3 groups selected from the group consisting of $C_{1-3}$ alkyl, halogen, CN and —$CH_2$-$L_3$; wherein $L_3$ is 4 to 6 membered saturated single heterocycle.

12. The compound of claim 1, or the pharmaceutically acceptable salt thereof, wherein $R_3$ is $C_{3-8}$ cycloalkyl substituted by $C_{2-8}$ alkenyl.

13. The compound of claim 1, or the pharmaceutically acceptable salt, stereoisomer, solvate or prodrug thereof, wherein the compound of formula (I) is the structure represented by formula (II):

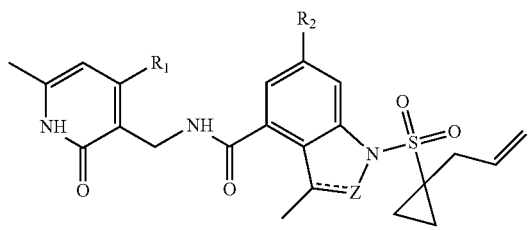

(II)

wherein $R_1$, $R_2$, Z are defined as claim 1.

14. The compound of claim 1, or the pharmaceutically acceptable salt, stereoisomer, solvate or prodrug thereof, wherein Z is =CH—; "---------" is a double bond; $R_1$ is fluorine, chlorine, methyl, methoxy, isopropoxy.

15. The compound of claim 1, or the pharmaceutically acceptable salt, stereoisomer, solvate or prodrug thereof, wherein Z is —$CH_2$—; "---------" is a single bond; $R_1$ is methyl, methoxy.

16. The compound of claim 1, or the pharmaceutically acceptable salt, stereoisomer, solvate or prodrug thereof, wherein the compound is selected from Table A.

17. A pharmaceutical composition comprising the compound of claim 1, or the pharmaceutically acceptable salt, solvate, stereoisomer or prodrug thereof; and a pharmaceutically acceptable carrier.

18. A method of treating a disease or condition mediated by EZH2, wherein the disease or condition mediated by EZH2 is selected from the group consisting of cancer, pulmonary arterial hypertension, myelofibrosis, human immunodeficiency virus (HIV) disease, graft versus host disease (GVHD), Weaver syndrome, psoriasis vulgaris and liver fibrosis, comprising administering to a patient in need thereof a therapeutically effective amount of the compound of claim 1, or the pharmaceutically acceptable salt, solvate, stereoisomer or prodrug thereof.

\* \* \* \* \*